(12) United States Patent
Birarda et al.

(10) Patent No.: US 9,927,352 B2
(45) Date of Patent: Mar. 27, 2018

(54) RAPID AND LABEL-FREE PROCEDURE FOR MICROBIAL COMMUNITY SCREENING AND PROFILING

(71) Applicant: The Regents of the University of California, Oakland, CA (US)

(72) Inventors: Giovanni Birarda, Trieste (IT); Alexander Probst, Koesslam (DE); Hoi-Ying Holman, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/550,904

(22) Filed: Nov. 21, 2014

(65) Prior Publication Data

US 2017/0138845 A1    May 18, 2017

Related U.S. Application Data

(63) Continuation-in-part of application No. 12/672,251, filed on Feb. 4, 2010.

(60) Provisional application No. 61/908,014, filed on Nov. 22, 2013, provisional application No. 60/954,311, filed on Aug. 6, 2007.

(51) Int. Cl.
| | |
|---|---|
| *G01N 21/35* | (2014.01) |
| *G01N 15/06* | (2006.01) |
| *C12Q 1/06* | (2006.01) |
| *G01N 15/14* | (2006.01) |
| *G01N 21/65* | (2006.01) |

(52) U.S. Cl.
CPC ............... *G01N 21/35* (2013.01); *C12Q 1/06* (2013.01); *G01N 15/1463* (2013.01); *G01N 21/65* (2013.01); *G01N 2021/3595* (2013.01)

(58) Field of Classification Search
CPC ........ G01N 21/35; G01N 21/65; G01N 15/06; G01N 15/1463; G01N 2021/3595; G01N 2015/0693; G01N 2201/12; G06F 19/24; G06F 19/26; G06F 19/00; G06F 19/10
See application file for complete search history.

(56) References Cited

U.S. PATENT DOCUMENTS

| | | | | |
|---|---|---|---|---|
| 2011/0317158 | A1* | 12/2011 | Lyng | ..................... G01N 21/65 356/301 |
| 2012/0082362 | A1* | 4/2012 | Diem | .................. A61B 5/0071 382/133 |

OTHER PUBLICATIONS

Gaigneaux, Anthoula et al. "Infrared spectroscopy as a tool for discrimination between sensitive and multiresistant K562 cells." European Journal of Biochemistry (2002) 269 1968-1973.*

(Continued)

*Primary Examiner* — Christopher Adam Hixson
(74) *Attorney, Agent, or Firm* — Michelle Chew Wong; Lawrence Berkeley National Laboratory

(57) ABSTRACT

Methods are described herein and termed Microbial Community Screening and Profiling (MCSP) for multi-dimensional analysis and non-destructive and label-free detection and analysis, which allow for complementary analytical techniques to be performed on the same sample for such multidimensional analysis.

4 Claims, 60 Drawing Sheets

(56) References Cited

OTHER PUBLICATIONS

Helm, D. et al. "Classiification and identification of bacteria by Fourier-transform infrared spectroscopy." Journal of General Microscopy (1991) 137 69-79.*

Yu, Peigiang. "Applications of hierarchical cluster analysis (CLA) and principal component analysis (PCA) in feed structure and feed molecular chemistry research, using synchrotron-based Fourier transform infrared (FTIR) microscopy." Journal of Agricultural and Food Chemistry (2005) 53 7115-7127.*

* cited by examiner

Differentiation of Archaea and Bacteria based on lipid and carbohydrate signatures Archaea Bacteria Note: Methanopyrus kandleri exhibits two types of spectra: (1) M. kandleri covered with whitish extracellular materials, and (2) M. kandleri without the whitish extracellular materials.

FIG. 3
Quantification of Archaea and Bacteria based on lipid and carbohydrate signatures
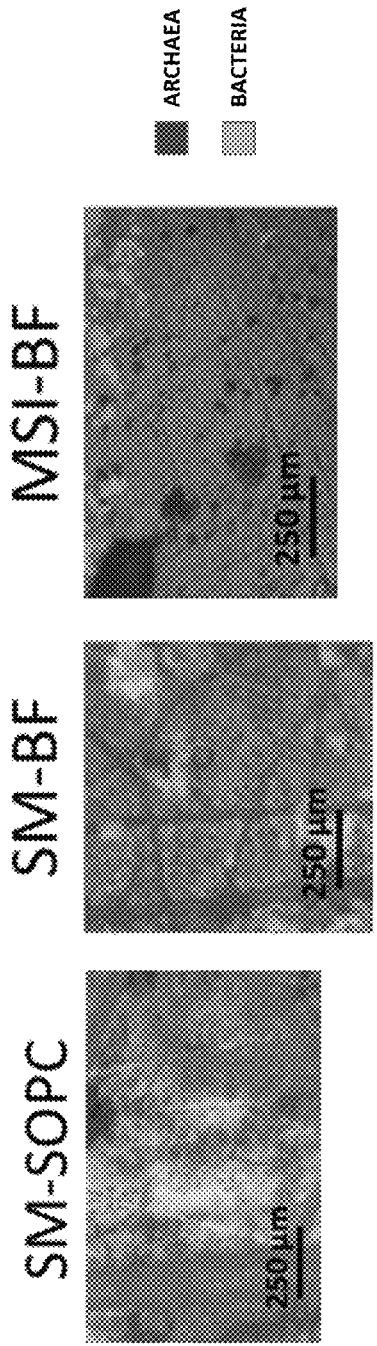
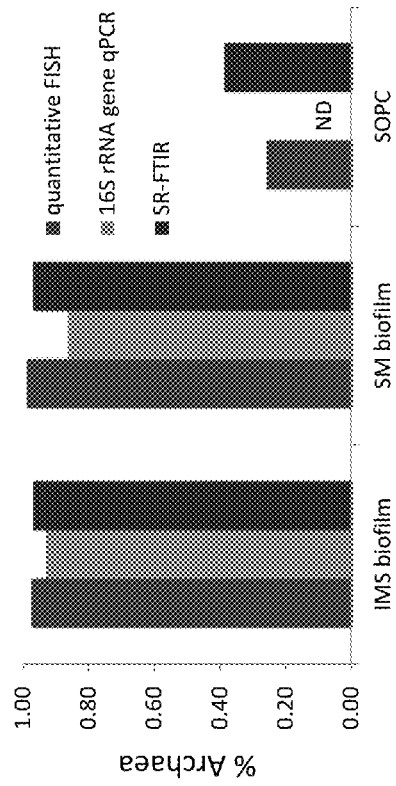

Discriminant analysis of microbiome based on spectral profiling

Fig. 9

| Biofilm replicate | Number of gene copies | | |
|---|---|---|---|
| | Archaeal 16S rRNA | Bacterial 16S rRNA | dsrB |
| 1 | 2.26E+06 | 6.88E+04 | 5.68E+03 |
| 2 | 3.33E+06 | 8.40E+04 | 5.46E+03 |
| 3 | 3.09E+06 | 7.49E+04 | 4.22E+03 |
| Mean | 2.89E+06 | 7.59E+04 | 5.12E+03 |

Abbreviation: dsrB, dissimilatory sulfite reductase subunit B.

Fig. 13C
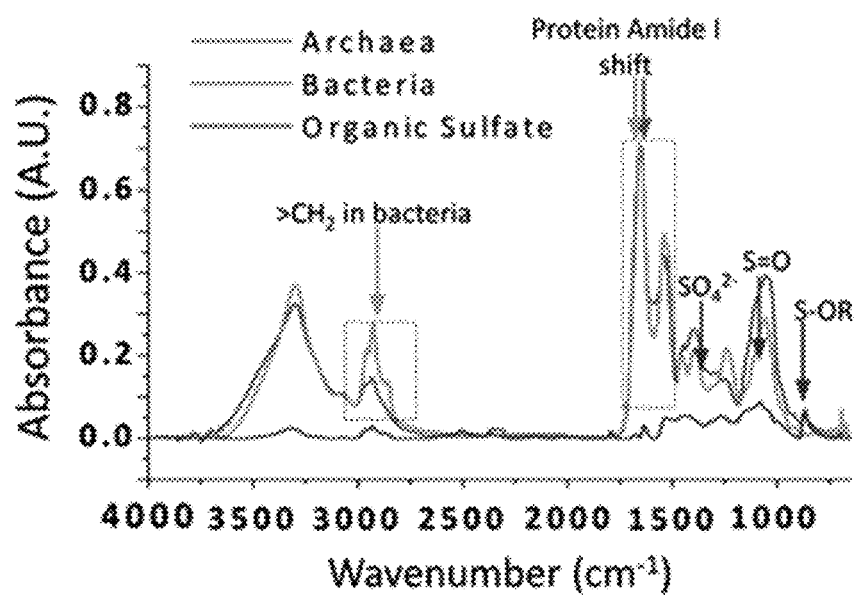
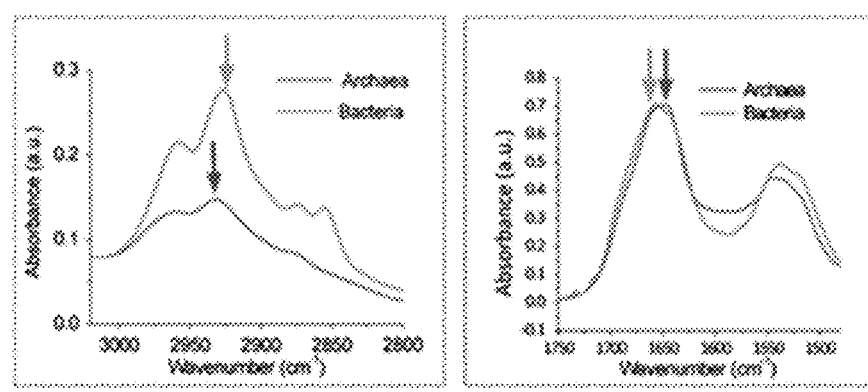

| Image | Channels | Pearson's R | Manders' R | Colocalization M1 | Colocalization M2 |
|---|---|---|---|---|---|
| Merge | FISH: IR | 0.504 | 0.798 | 0.988 | 1.000 |

Fig. 19A

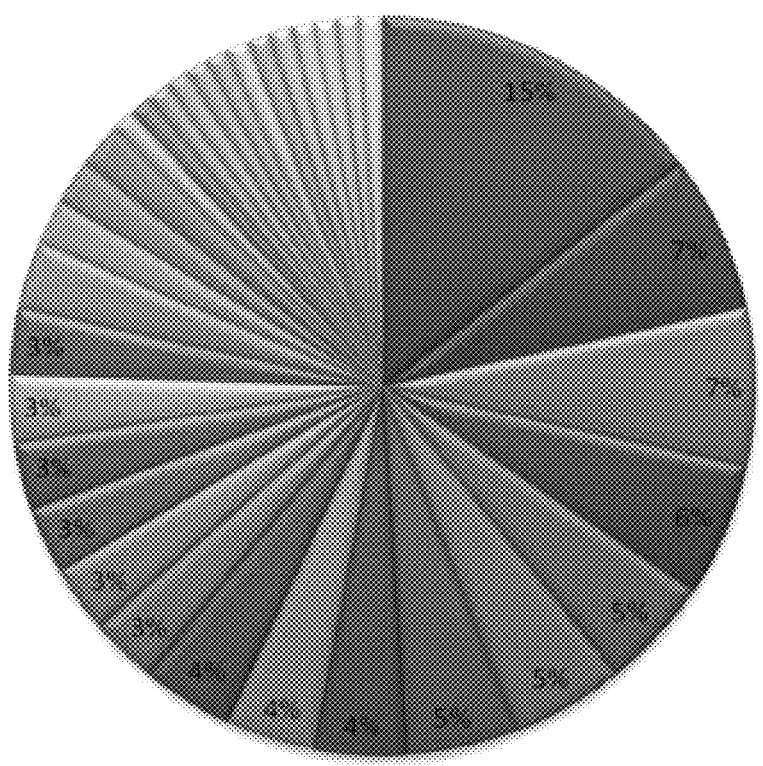

- Deltaproteobacteria
- Firmicutes/Tenericutes
- Bacteroidetes
- Betaproteobacteria
- Gammaproteobacteria
- Chloroflexi
- GN02
- Alphaproteobacteria
- Euryarchaeota
- Elusimicrobia
- Cyanobacteria
- TM6
- ZB2
- Entotheonella
- SHA-95
- WPS-2
- WS6
- OP11
- Planctomycetes
- OP3
- Acidobacteria
- Verrucomicrobia
- ABY1_OD1
- Nitrospirae
- Epsilonproteobacteria
- Chlorobi
- Unclassified
- Spirochaetes
- WS3
- AD3
- NKB19
- TM7
- WS2

Fig. 25

| Name | Primer Sequence 5'->3' | Archaea | | Bacteria | | Reference |
|---|---|---|---|---|---|---|
| Primer | | n | coverage | n | coverage | |
| 344aF | ACGGGGYGCAGCAGGCGCGA | 29314 | 42% | 2 | 0% | Casamayor et al. (2002)* |
| 1406uR | ACGGGCGGTGTGTRCAA | 10107 | 14% | 401702 | 26% | Lane (1991) |
| 4aF | TCCGGTTGATCCTGCCRG | 9923 | 14% | 6 | 0% | Hazen et al. (2010) |
| 1492uR | GGTTACCTTGTTACGACTT | 1312 | 2% | 64553 | 4% | Hazen et al. (2010) |

Fig. 26

| Accession number | Taxonomy (phylum, class, order, family, genus, clone ID) | Originally found in | Proposed role in string-of-pearls community (Moissl et al., 2002; Rudolph et al., 2001) | Detected in (no of times) |
|---|---|---|---|---|
| AJ307946 | Bacteroidetes, Bacteroidetes, Bacteroidales, Porphyromonadaceae, Paludibacter, clone sipK57 | Sippenauer Moor | minor | biofilm (1) |
| AJ307948 | Bacteroidetes, Flavobacteria, Flavobacteriales, Flavobacteriaceae, unclassified, clone sipK12 | Sippenauer Moor | minor | biofilm (2) |
| AJ307949 | Chloroflexi, Anaerolineae, Anaerolineales, Anaerolineaceae, unclassified, clone sipK52 | Sippenauer Moor | minor | biofilm (2) |
| AJ307939 | Proteobacteria, Alphaproteobacteria, Rhizobiales, Bradyrhizobiaceae, Bradyrhizobium, clone sipK8 | Sippenauer Moor | minor | biofilm (1) |
| AJ307937 | Proteobacteria, Alphaproteobacteria, Sphingomonadales, Sphingomonadaceae, Novosphingobium, clone sipK17 | Sippenauer Moor | minor | biofilm (1) |
| AJ307935 | Proteobacteria, Betaproteobacteria, Hydrogenophilales, Hydrogenophilaceae, Thiobacillus, clone sipK89 | Sippenauer Moor | minor | biofilm (1) |
| AJ307944 | Proteobacteria, Deltaproteobacteria, Desulfobacterales, Desulfobulbaceae, Desulfocapsa, clone sipK108 | Sippenauer Moor | minor | biofilm (1), spring water |
| AJ307942 | Proteobacteria, Deltaproteobacteria, Desulfuromonadales, Geobacteraceae, Geobacter, clone sipK44 | Sippenauer Moor | minor | biofilm (1) |
| AJ307940 | Proteobacteria, Epsilonproteobacteria, Campylobacterales, Helicobacteraceae, Sulfuricurvum, clone sipK119 / IMB1 | Sippenauer Moor & Muehlbacher Schwefelquelle | minor (Sippenauer Moor) / key species (Muehlbacher Schwefelquelle) | biofilm (1), spring water |
| AJ307941 | Proteobacteria, Epsilonproteobacteria, Campylobacterales, Helicobacteraceae, Sulfurovum, clone sipK54 | Sippenauer Moor | minor | biofilm (2), spring water |
| AJ307933 | Proteobacteria, Gammaproteobacteria, Thiotrichales, Thiotrichaceae, Thiotrix, clone sipK4 | Sippenauer Moor | key species | biofilm (2) |

Fig. 28A
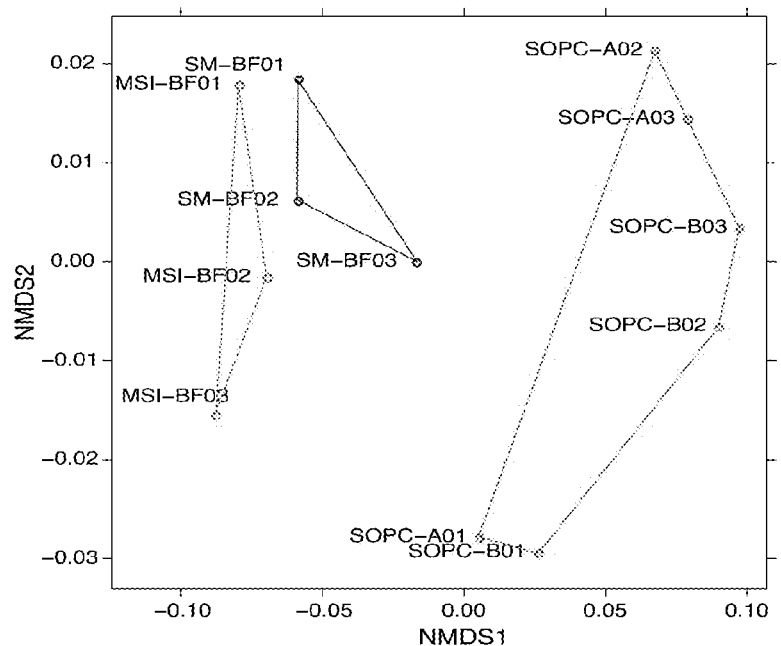
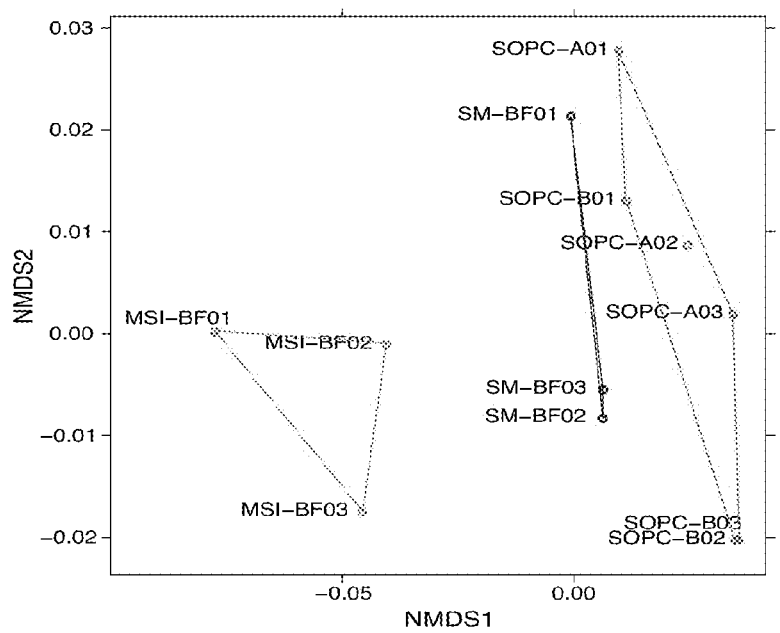

REPLACEMENT DRAWING
MSI  SM
Fig. 29A  Fig. 29B
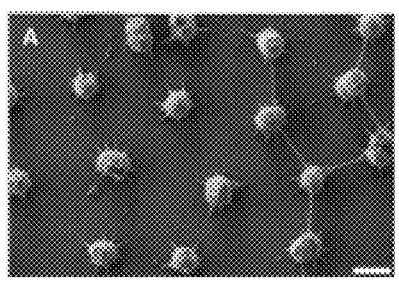 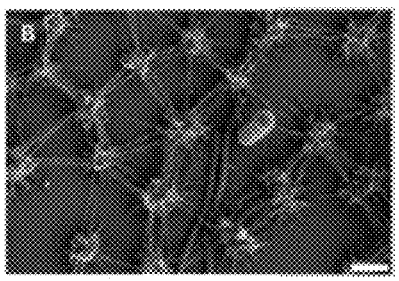
Fig. 29C  Fig. 29D
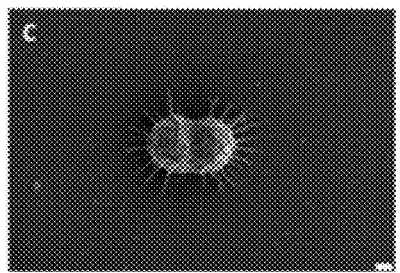 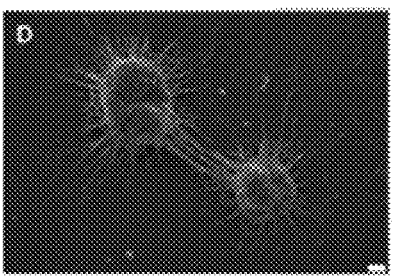
Fig. 29E  Fig. 29F
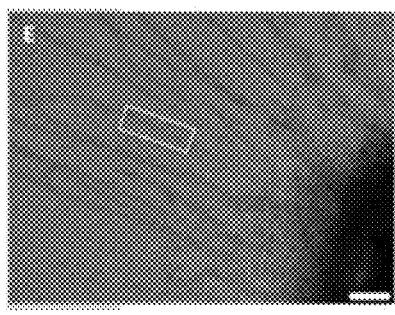 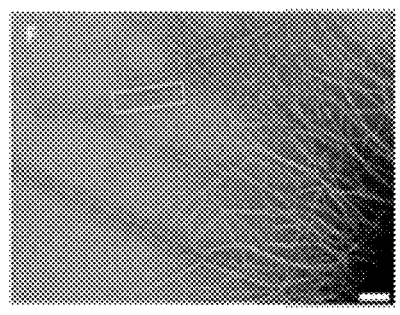

Fig. 31

| Method | Measurand | MSI-BF | SM-BF | SOPC |
|---|---|---|---|---|
| QPCR (per ng DNA) | Archaeal 16S rRNA genes | 2.99E+06 (±5.63E+05)* | 2.09E+06 (±1.09E+06) | 2.03E+05 (±5.48E+04) |
| | Bacterial 16S rRNA genes | 7.48E+04 (±7.65E+03)* | 2.20E+04 (±2.68E+03) | 5.75E+05 (±1.09E+05) |
| | DsrB genes | 5.12E+03 (±7.87E+02)* | 1.97E+03 (±9.82E+02) | 3.46E+03 (±1.25E+02) |
| | Percent Archaea | 97.44%* | 98.96% | 26.09% |
| FISH | Percent archaeal cells | 92.96 (±2.16) | 86.41 (±7.02) | ND |
| | Percent SRB385 stained Bacteria | 85.4 (±4.7)* | 39.32 (±11.61) | ND |
| | Percent DeltaMix stained Bacteria | 89.2 (±0.9)* | 63.87 (±14.70) | ND |
| SR-FTIR | Percent archaeal biomass | 97.0 (±6.0) | 97.1 (±4.4) | 38.7 (±13.8) |

*data from Probst et al., 2013
ND: Not Determined

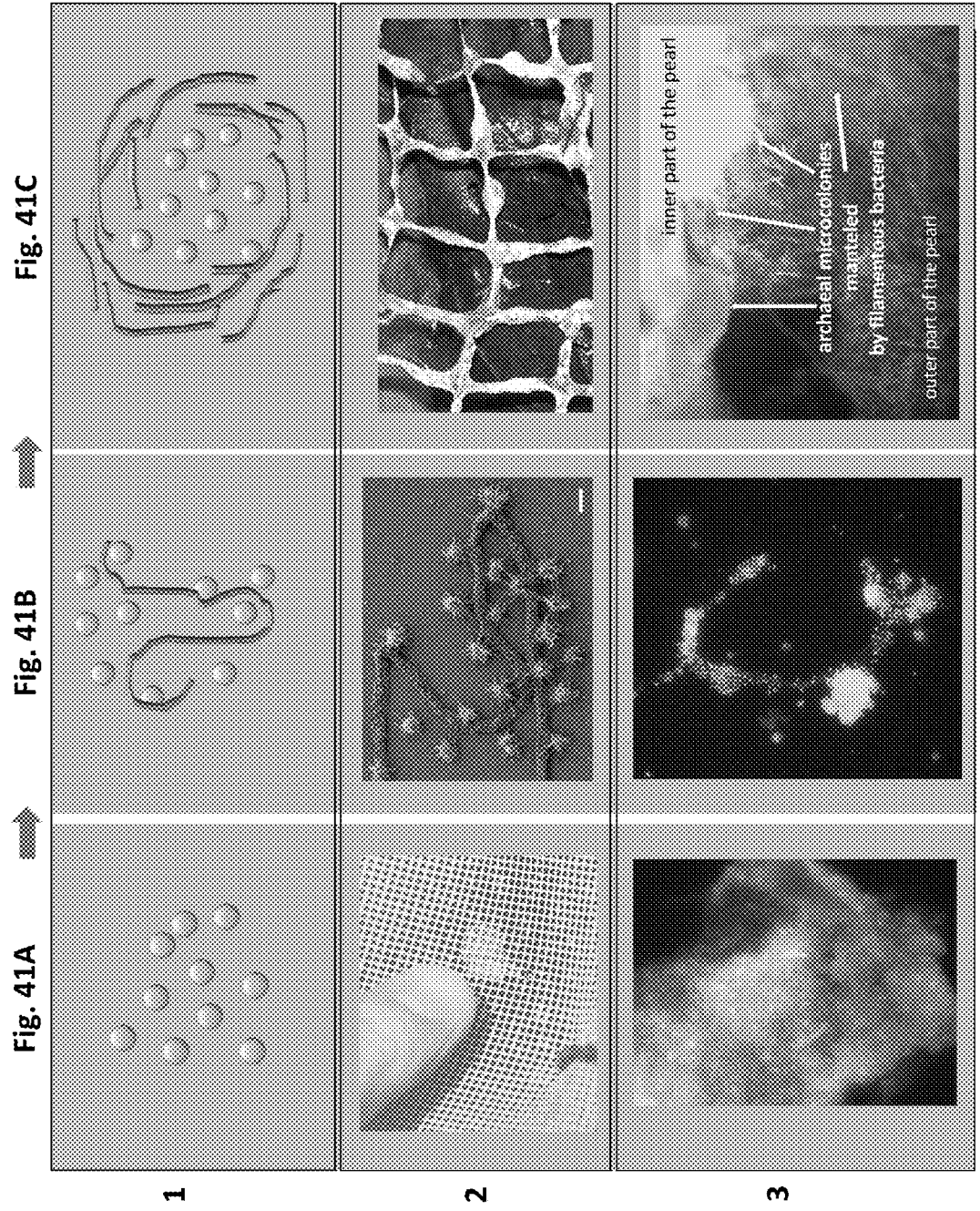

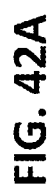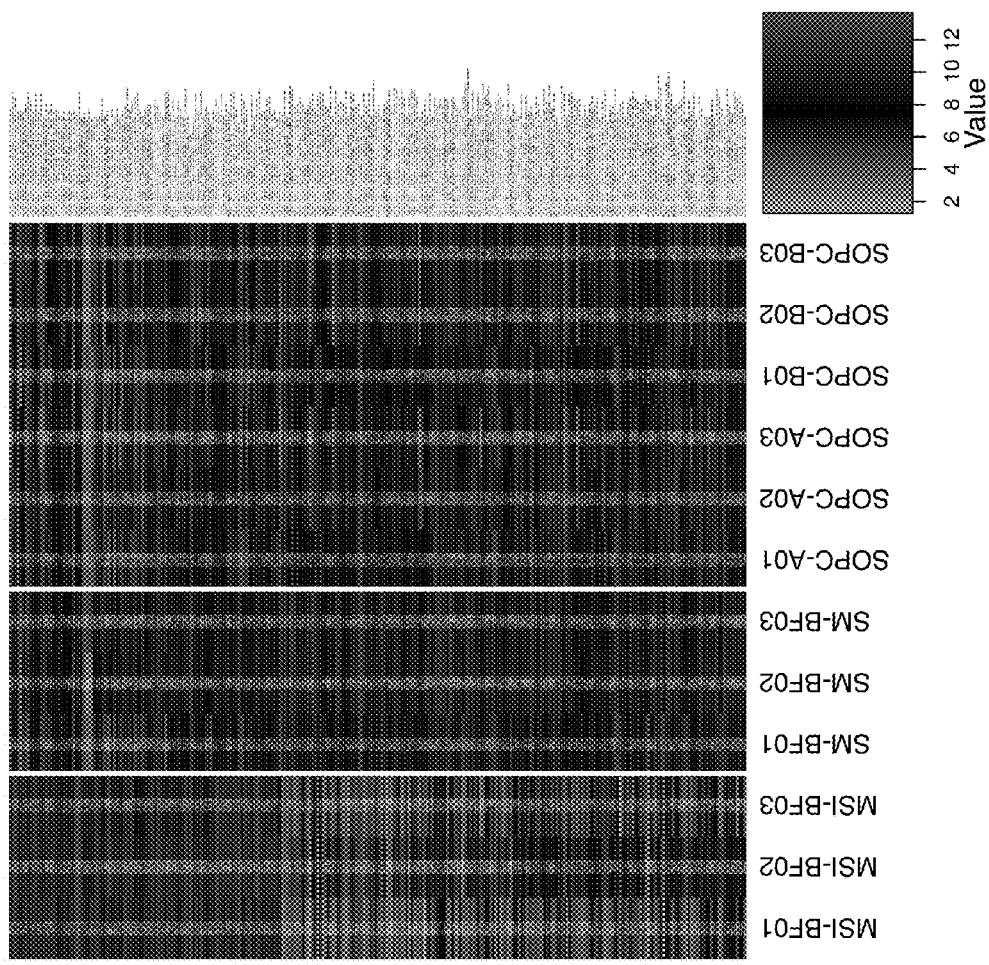
FIG. 42A

RAPID AND LABEL-FREE PROCEDURE FOR MICROBIAL COMMUNITY SCREENING AND PROFILING

CROSS-REFERENCE TO RELATED APPLICATIONS

This application is a non-provisional application of and claims priority to U.S. Provisional Patent Application No. 61/908,014, filed on Nov. 22, 2013, hereby incorporated by reference in its entirety. This application is a continuation-in-part application of and claims priority to U.S. patent application Ser. No. 12/672,251, filed on Feb. 4, 2010, also hereby incorporated by reference in its entirety.

STATEMENT OF GOVERNMENTAL SUPPORT

This invention was made with government support under Contract No. DE-AC02-05CH11231 awarded by the U.S. Department of Energy. The government has certain rights in the invention.

REFERENCE TO A SEQUENCE LISTING APPENDIX

This application also incorporates by reference the sequence listing found in computer-readable form in a *.txt file entitled, "2014-015-02_ST25.txt", created on Jul. 2, 2015.

BACKGROUND OF THE INVENTION

Field of the Invention

The present invention relates to a rapid and direct molecular method for profiling microbial populations and communities using vibrational spectromicroscopy and imaging.

Related Art

Microbes always live in communities. They make up the foundation of the biosphere and sustain all the life forms on earth. They play a key role in the cycling of elements and nutrients, carry out processes that are beneficial to the environment and to human society, yet they remain largely unexplored. Knowledge of the microbial communities, such as the predominant species, their role and interaction, their spatial distribution and variation with time or in response to a natural or man-made disturbance, is essential to understand the planet scale effect of any ecological phenomenon. Currently, scientists in environmental microbiology use amplicon analyses of different marker genes to explore microbiome structures. A commonly used is marker gene 16S rRNA that has already been used for this purpose in thousands of studies. Apart from 16S rRNA gene profiles, there are other methods such as comparative metagenomics and transcriptomics, which mainly focus on functional changes of microbial communities, as well as lipidomics, which permits relative quantification and identification of cellular lipids. However, the aforementioned methods and currently applied methods require complete destruction of the sample in order to extract specific analytes for further analyses. Thus, there is a need for methods which provide the same levels of quantification and identification and community profiling, yet do not destroy samples.

BRIEF SUMMARY OF THE INVENTION

The present invention provides a method for rapid and non-destructive (1) identification, (2) quantification of microorganism abundance (e.g. Archaea versus Bacteria) within microbial communities, and (3) elucidation of entire community functional relationships at a chemical level.

In some embodiments, a method for screening and highlighting the community relationships based on the global chemical compositions of the inspected samples rather than the genetic profile.

In various embodiments, a fast and non-destructive tool for an immediate preliminary screening of the freshly collected biological samples.

In some embodiments, a method to distinguish archaea from bacteria based on the vibrational spectral features (Table 1) in the lipid region (2800-3100 $cm^{-1}$), the carbohydrate region (1000-1280 $cm^{-1}$), or the molecular fingerprint region (1480-650 $cm^{-1}$).

In some embodiments, a method for the quantification of archaeal and bacterial biomass within the same environmental sample using the $CH_3/CH_2$ ratio from the vibrational spectra.

In other embodiments, a method to produce data that can be used for a discriminant analysis of microbiome based on spectral profiling using multivariate statistics including Principal Component Analysis or Principal Component-Linear Discriminant Analysis (PC-LDA).

In other embodiments, a method for preparing or generating data that can be used for microbial community profiling using ordination analyses such as NMDS (Non-metric multidimensional scaling) or PCoA (Principal Coordinate Analysis).

In another embodiment, the methods further comprising supervised and/or unsupervised statistical methods.

BRIEF DESCRIPTION OF THE DRAWINGS

FIG. 1A Archaea: *S. solfataricus* (glycosilated surface layer); *M. kandleri.* (pseudopeptidoglycan and proteinaceous sheath; please note, *M. kandleri* exhibits two types of spectra, depending on the observed accumulation of extracellular material (type 1: with extracellular material, type 2: without extracellular material)). FIG. 1B Bacteria: *E. coli* (Gram-negative cell wall), *B. atrophaeus* (Gram-positive cell all). The numbers of reference spectra per species measured are given (n).

FIG. 3. Binary (green-red two colors) heat maps of biofilms (BFs) and string-of-pearls (SOPCs) from three different sampling sites in Germany: Sippenauer Moor (SM-BF), Sippenauer Moor (SM-SOPC), and Muehlbacher Schwefelquelle, Isling (MSI-BF). The heat maps show the distribution of Archaea and Bacteria within the samples.

FIG. 9. Quantification of archaeal/bacterial 16S rRNA and dsrB gene sequences in 1 ng metagenomic DNA from SM1 Euryarchaeon biofilm samples taken at two different sampling times.

FIG. 13A-D. (6a and 6c) SR-STIR images of Bacteria in the Archaea-dominated biofilm. SR-FTIR images (220 μm by 180 μm) showing the distribution of microorganisms and biogeochemical products in an Archaea-dominated biofilm. (FIG. 13A, 13B) Distribution heatmap (from univariate analysis) of the relative abundance of total proteins (based on the peak area centered at ~1548 $cm^{-1}$), of bacterial lipids (the ratio of the peak area of $CH_2$ centered at ~2852 $cm^{-1}$ to the peak area of $CH_3$ at ~2872 $cm^{-1}$), carbohydrates (the peak area centered at ~1089 $cm^{-1}$), sulfur/carbon biochemical cycling products (S=O from organic sulfate products, centered at ~1240 $cm^{-1}$, S=O of inorganic sulfate centered at ~1130 cm−1 and CO32-groups of carbonate minerals in the 880-840 $cm^{-1}$ region. The OH of clay centered at ~3695 cm−1 is not shown here), The white circles with numbers (1-6) in the bright field and in the SR-FTIR images (FIG. 13B) correspond to the transflectance spectra (FIG. 13A). The circles represent pixels where the spectra were recorded. Note: Filamentous bacterial structures in the biofilm were rarely observed but specifically presented here in order to illustrate the lipid signatures of Bacteria and Archaea (for more samples please see FIGS. 16A-D). Scale bars=25 μm. (FIGS. 13C and 13D) Multivariate curve resolution analysis to differentiate Archaea and Bacteria. (FIG. 13C) Spectra of the three components extracted from the MCR, in red component 1 (Archaea), in green component 2 (Bacteria), in blue component presenting sulfate spectral features, with arrows pinpointing the spectral markers used in the analysis, in the panels below highlighted the spectral region of lipids, important region for the distinction of Bacteria and Archaea since their different membrane composition, and protein region where a shift is observable in Amide I band, index of a different protein content in Bacteria and Archaea (FIG. 13D): Relative concentration images (220 μm by 180 μm) of Archaea (component 1) and Bacteria (component 2) recovered by the MCR analysis and the chemical distribution maps of organic sulfate (C—S=O) in blue. Merging the relative bacterial concentration image (in green color) with the organic sulfate distribution map (in blue) reveals the co-localization of bacteria and organic sulfate. Scale bars=50 μm.

FIG. 14. Tentative band assignments of the fundamental vibrational modes used in SR-FTIR spectromicroscopy.

FIG. 16A: PCA-LDA analysis of spectra extracted from the region of field-collected biofilms that are without mineral particles (n=5, 608). FIG. 16C: PCA-LDA analysis of spectra extracted from the region of field-collected biofilms that are with mineral particles (n=12,439). Spectra in both cases show similar classification patterns along the second PC-LDA factor. Each ellipse covers an area of 95% confidence level. FIGS. 16B and 16D: The 2nd PC-LDA loading spectrum also has two distinct peaks at 2920 cm$^{-1}$ and 2850 cm$^{-1}$ (see arrows) which are associated with C—H2 bond stretching. Notice that the cluster vector spectrum for the complete set of field-collected biofilms (with/without minerals) exhibit little features (relative to those of reference archaea and bacteria), likely due to the spread of the microorganisms across the archaea and bacteria spaces as demonstrated in the corresponding PC-LDA score plots.

FIG. 17A Left: MRC recovered SR-FTIR images of archaea (component 1, red), bacteria (component 2, green), and right: archaea fluorescence in situ hybridization (FISH) stained image (red) of the same biofilm. Scale bars=50 µm.

FIGS. 19A and B. (12a) FIG. 19A shows distribution of subfamilies in higher taxa detected by PhyloChip G3 in the spring water of the Muehlbacher Schwefelquelle.

(FIG. 21A, 14a) CTC staining of the biofilm showed metabolic activity of several cells, also of some SM1 Euryarchaeal cocci. (FIG. 21B, 14b) FISH with Delta495a/b/c probe mix labeled sulfate-reducing bacteria. (FIG. 21C, 14c) DAPI staining. (FIG. 21D, 14d) Overlay of A, B, and C. Based on the fact that there was an overlap of CTC, FISH and DAPI signals it can be concluded that some sulfate-reducing bacteria in the biofilm showed metabolic activity under laboratory conditions after an anaerobic incubation in spring water at 11° C. for 2 hrs. White circles highlight examples of (overlapping) signals from FISH, CTC, and DAPI. Bar=10 µm.

(FIG. 22A, 15a) Bright Field. (FIG. 22B, 15b) Cross-polarized light highlighting minerals. (FIG. 22C, 15c) Natural fluorescence (WU: 330-385 nm excitation, >420 nm emission) highlighting certain mineral and filamentous microorganisms. (FIG. 22D, 15d) Natural fluorescence (WG: 510-550 nm excitation, >590 nm emission) highlighting certain filamentous microbes. Scale bars=50 µm FIG. 23A-C. SR-FTIR images (~220 µm by ~180 µm) from univariate analysis showing the distribution of key biomolecules and sulfur/carbon biogeochemical cycling products in three different biofilms (FIG. 23A, 23B, 23C) from the sulfidic spring Muehlbacher Schwefelquelle. Scale bars=50 µm.

FIG. 25. Comparison of archaeal primer specificity checked via Ribosomal Database Project II (http://rdp.cme.msu.edu; July 2011). Primers of this study are opposed to those used in previous PhyloChip G3 studies (Hazen et al., 2010). n=no. of sequences covered. Coverage=percent of covered sequences compared to total no. of sequences in the database. aF=archaea-directed forward. uR='universal' reverse.

FIG. 26, OTUs corresponding to string-of pearl cor community members detected subsurface biofilm.

The following figures correspond to Figures for Example 2.

Figure 27:
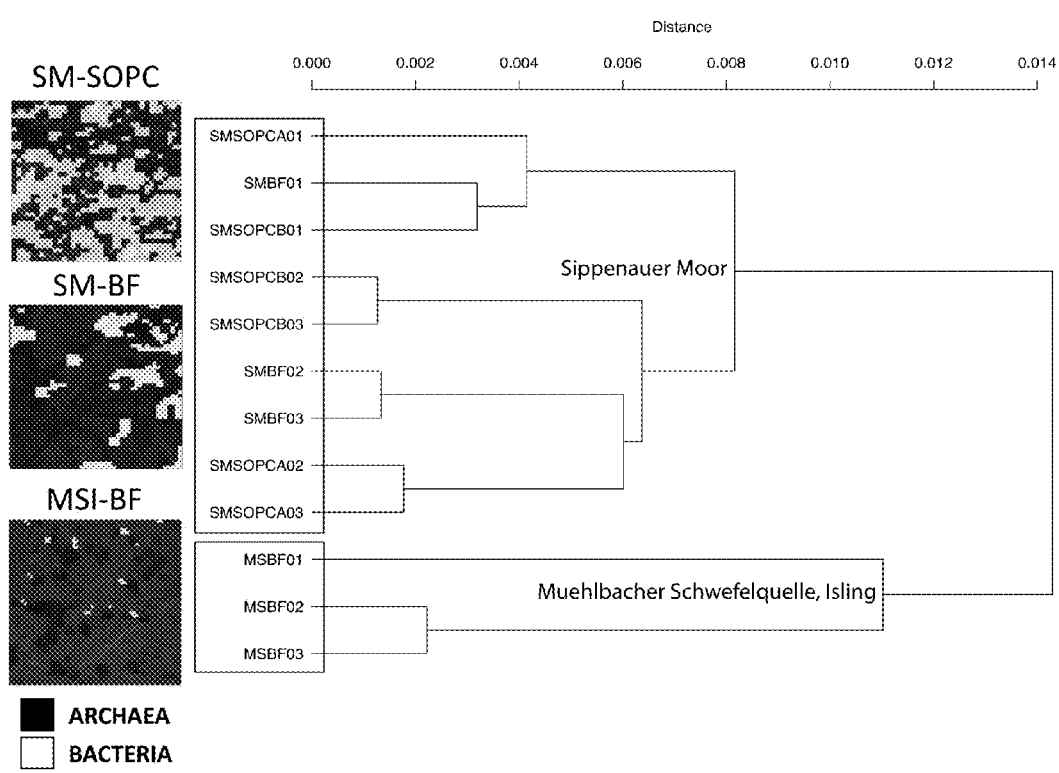

FIG. 27. Abundance of Archaea and Bacteria in samples and the overall community relationship. Small panels present binary images of infrared data collected for three sample types, SM-BF (Sippenauer Moor, biofilm), SM-SOPC (Sippenauer Moor, string-of-pearls community) and MSI-BF (Muehlbacher Schwefelquelle, Isling, biofilm). Infrared maps show the distribution of Archaea and Bacteria in the samples. One pixel corresponds to 2 µm. Hierarchical clustering based weighted UniFrac of abundance values of eOTUs (Bacteria and Archaea). Two different clusters separating the samples based on hydrogeology were observed.

FIG. 28A-D. Detailed community profiling using PhyloChip G3™ and SR-FTIR. (FIG. 28A) Ordination analysis of PhyloChip G3™ data based on weighted UniFrac measure of eOTU abundances followed by non-metric multidimensional scaling (NMDS). Stress for NMDS of archaeal eOTUs (#37): 0.0088. Stress for NMDS of bacterial eOTUs (#1300): 0.0223. (FIG. 28B) Heatmap displaying significantly different families found between the two biofilm types, MSI-BF and SM-BF by PhyloChip G3™ assay. Significance is based on aggregated hybscores of eOTUs on family level followed by a Welch-test. (FIG. 28C) Ordination analysis of SR-FTIR data based on a linear discriminant analysis and principal component analysis (PCA-LDA) in the spectral region of 2800-3100 cm-1 on the archaea spectra extracted from the maps from the three different locations. On the right there is the plot of PC-LDA loadings. PC-LDA1 explains for the 93.4% of the variance, PC-LDA2 for 5.3% and PC-LDA3 for 0.9%. Arrows point to the infrared signals used to explain the difference between the samples: 2975 cm-1, 2965 cm-1, 2924 cm-1 and 2850 cm-1. (FIG. 28D) PCA-LDA in the spectral regions of 900-1280 cm-1 and 2800-3100 cm-1 on SR-FTIR spectra of the bacteria "pixels" from the chemical maps of the samples at the three different locations. On the right there is plot of PC-LDA loadings in the two spectral region of interest. PC-LDA1 explains for the 54.5% of the variance, PC-LDA2 for 28.6% and PC-LDA3 for 7.3%. Arrows point to the main infrared signals used to explain the difference between the samples: $2958$ $cm^{-1}$, $2925$ $cm^{-1}$, $2870$ $cm^{-1}$ and $2850$ $cm^{-1}$, in the second panel $1250$ $cm^{-1}$, $1110$ $cm^{-1}$, $1080$ $cm^{-1}$ and $1045$ $cm^{-1}$.

FIG. 29A-F. Scanning and transmission electron micrographs of biofilms, cells and hami. Left panels: MSI, right panel: SM. (FIG. 29A) Scanning electron micrograph of MSI biofilm, showing SM1 euryarchaeal cells with defined distances and cell-cell connections. Bar: 1 μm. (FIG. 29B) Scanning electron micrograph of SM biofilm, showing SM1 euryarchaeal cells with defined distances and fine-structured cell-cell connections. In-between: Bacterial filamentous and rod-shaped cells. Bar: 1 μm. (FIG. 29C) Scanning electron micrograph of dividing SM1 euryarchaeal cell (MSI) with cell surface appendages. Bar: 200 nm. (FIG. 29D) Scanning electron micrograph of dividing SM1 euryarchaeal cell (SM) with cell surface appendages. Bar: 200 nm. (FIG. 29E) Transmission electron micrograph of cell surface appendages (hami) of SM1 euryarchaeal cells from the MSI biofilm. The hami carry the nano-grappling hooks, but besides that appear bare (square), without prickles (Moissl et al 2005). Bar: 100 nm. (FIG. 29F) Transmission electron micrograph of cell surface appendages and matrix of SM1 euryarchaeal cells from the SM biofilm. The hami reveal the typical ultrastructure, with nano-grappling hooks and barb-wire-like prickle region (square, Moissl et al 2005). Bar: 100 nm.

Figure 30:
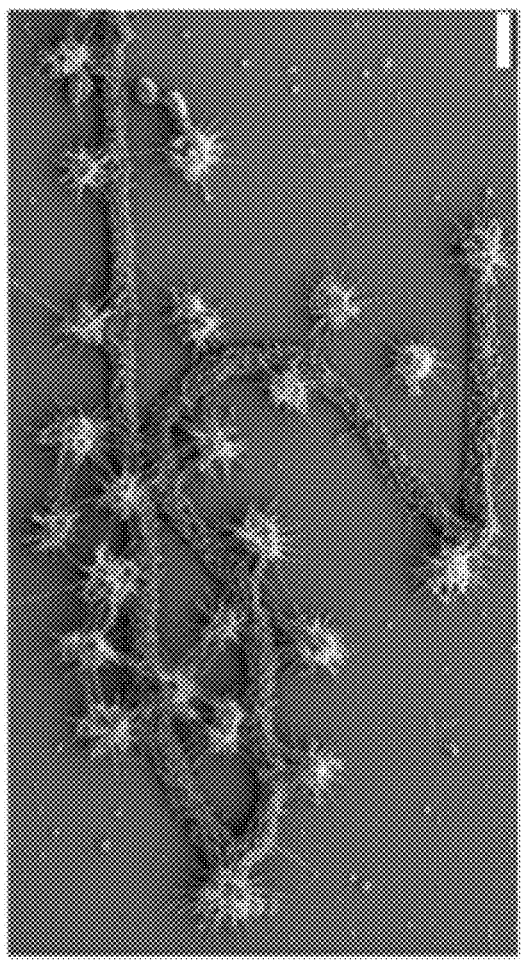

FIG. 30. Scanning electron micrograph of filamentous bacterium and surrounded and cocooned by the SM1 euryarchaeal cells (SM-BF). Bar: 1 μm.

FIG. 31. Quantification of archaeal and bacterial signatures via qPCR, FISH and SR-FTIR (values in brackets give standard deviation).

Figure 32:
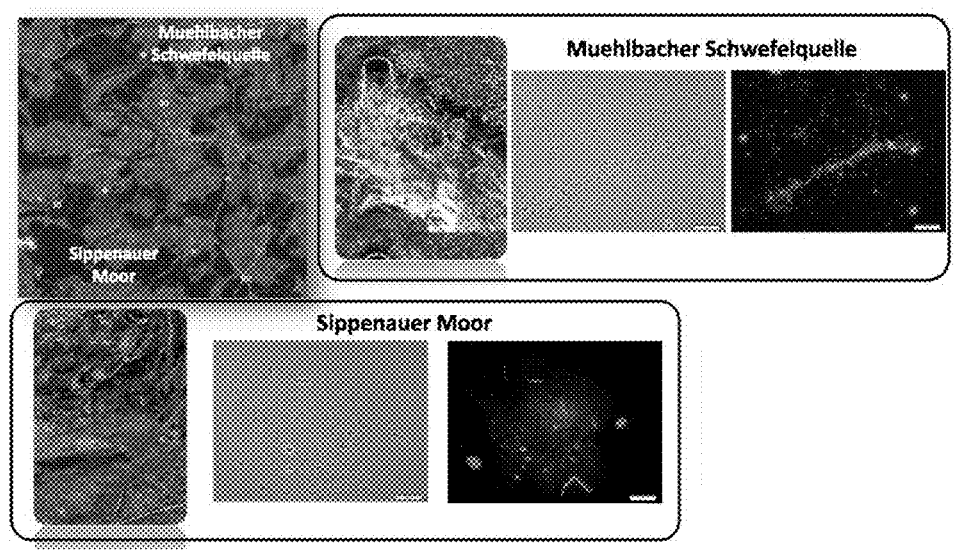

FIG. 32. FISH staining of archaea and bacteria. The SM1-Euryarchaeon has been discovered during the microbial analysis of cold sulfidic springs near Regensburg, Germany. It is a unique model for studying Archaea in a natural biofilm.

Figure 33:
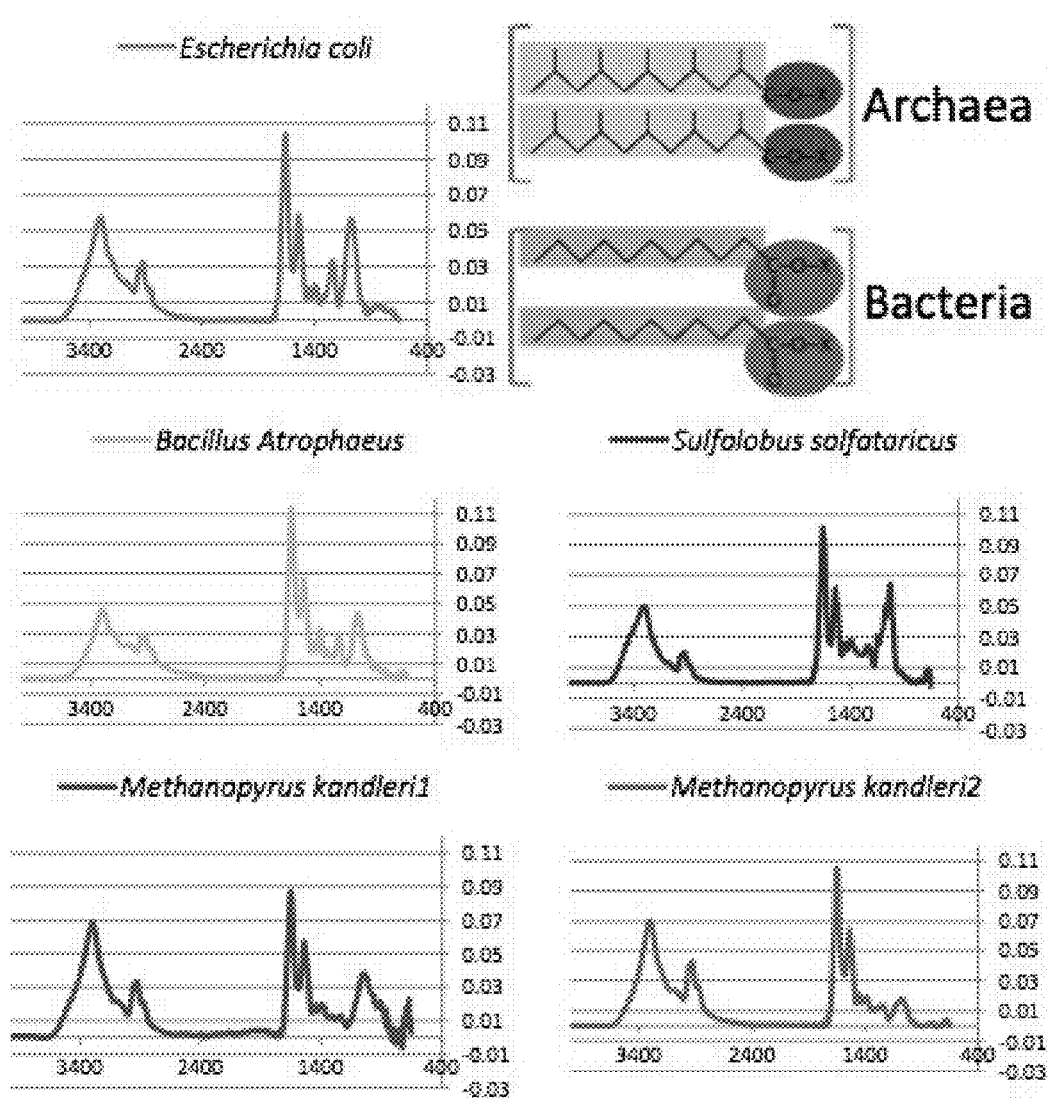

FIG. 33. Reference spectra acquisition and comparison.

Figure 34:
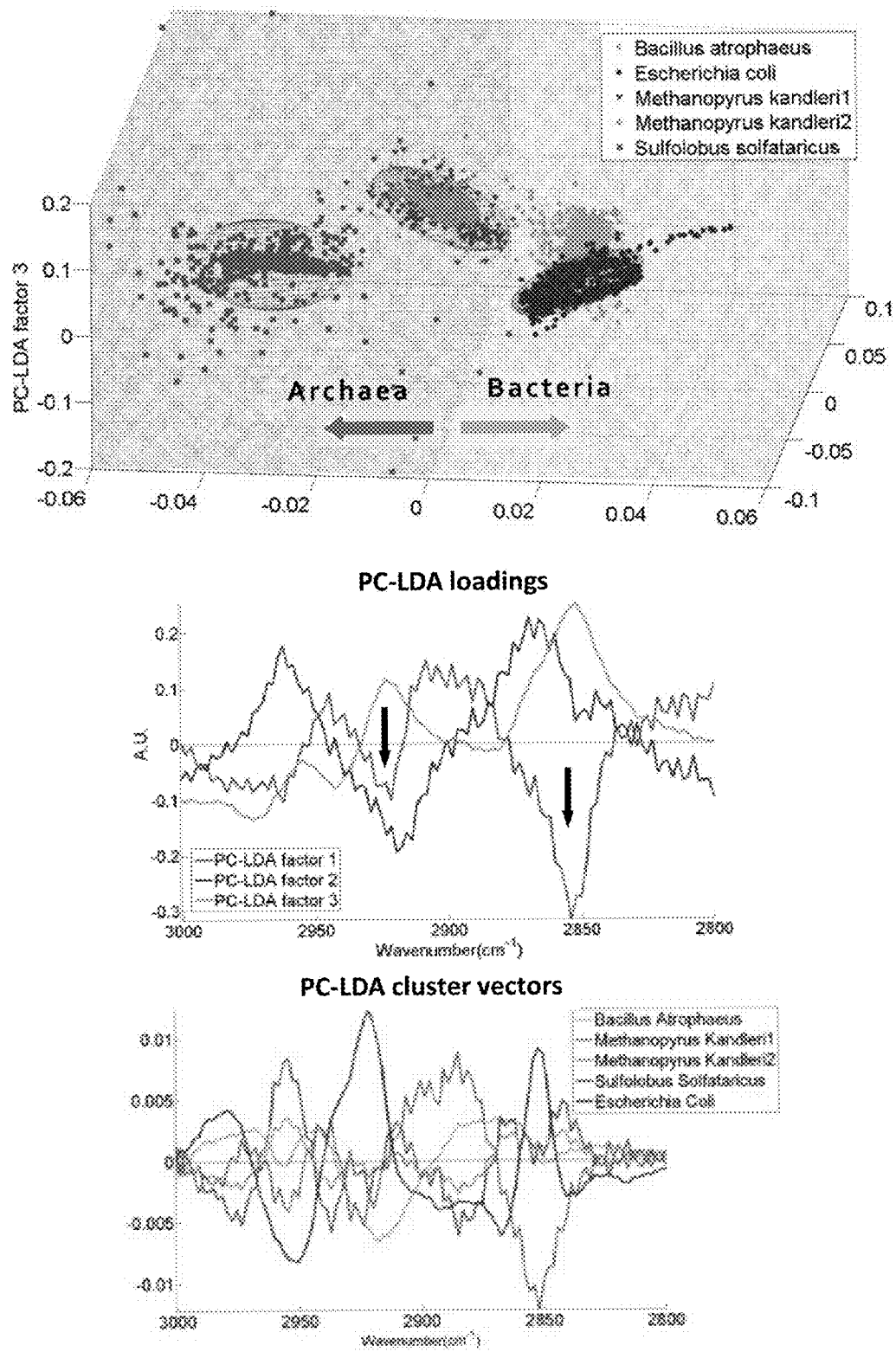
Figure 35:
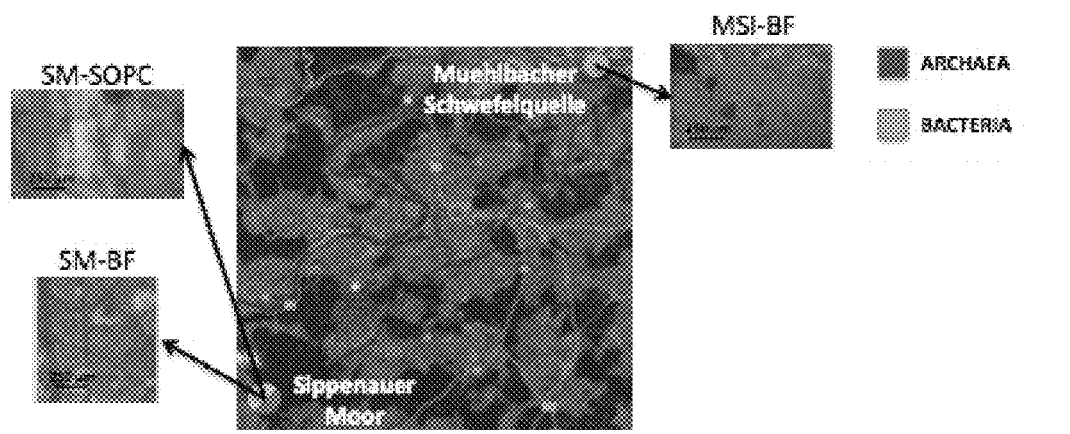

FIG. 34. The PCA-LDA analysis of all the measured reference.

FIG. 35.

Figure 36:
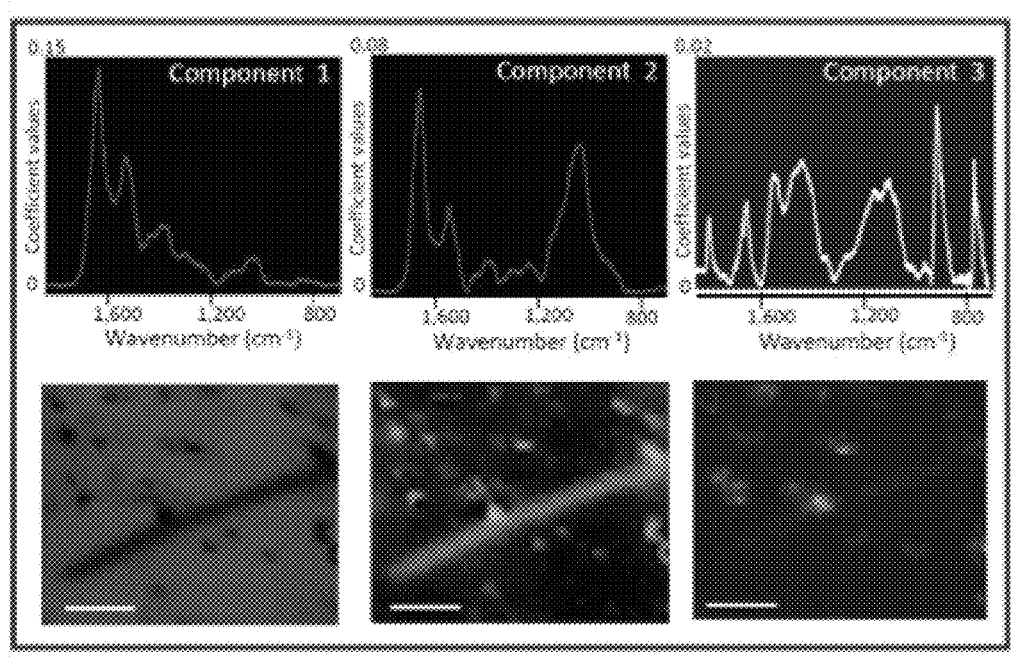
Figure 37:
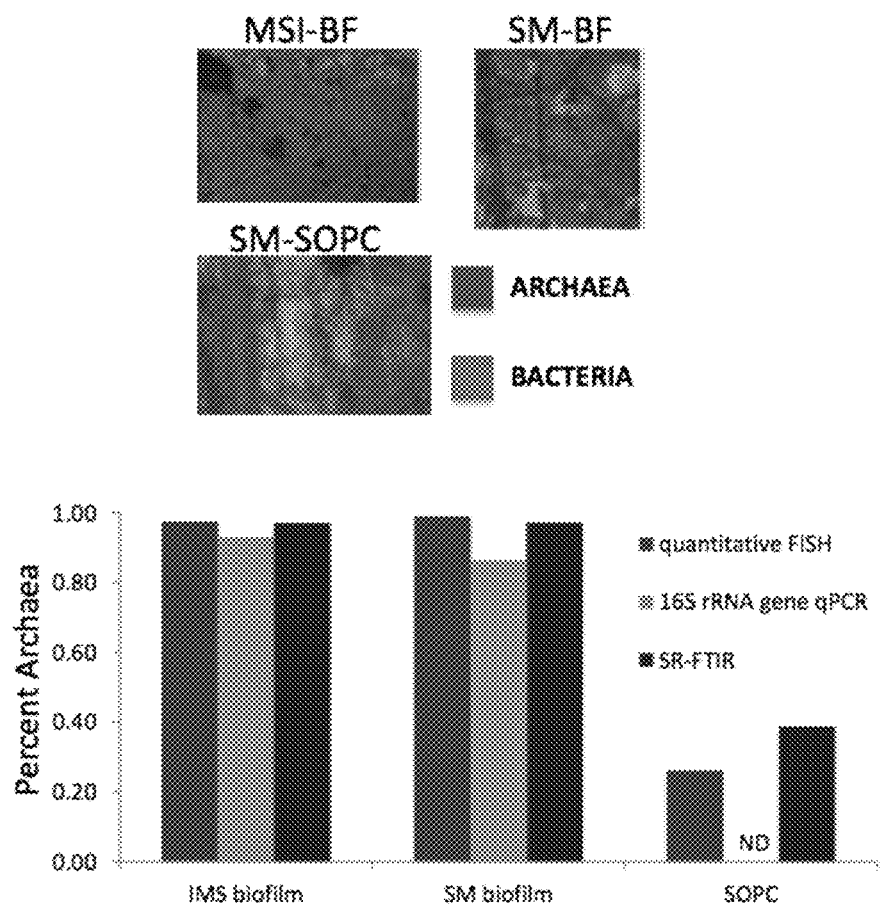
Figure 38A:
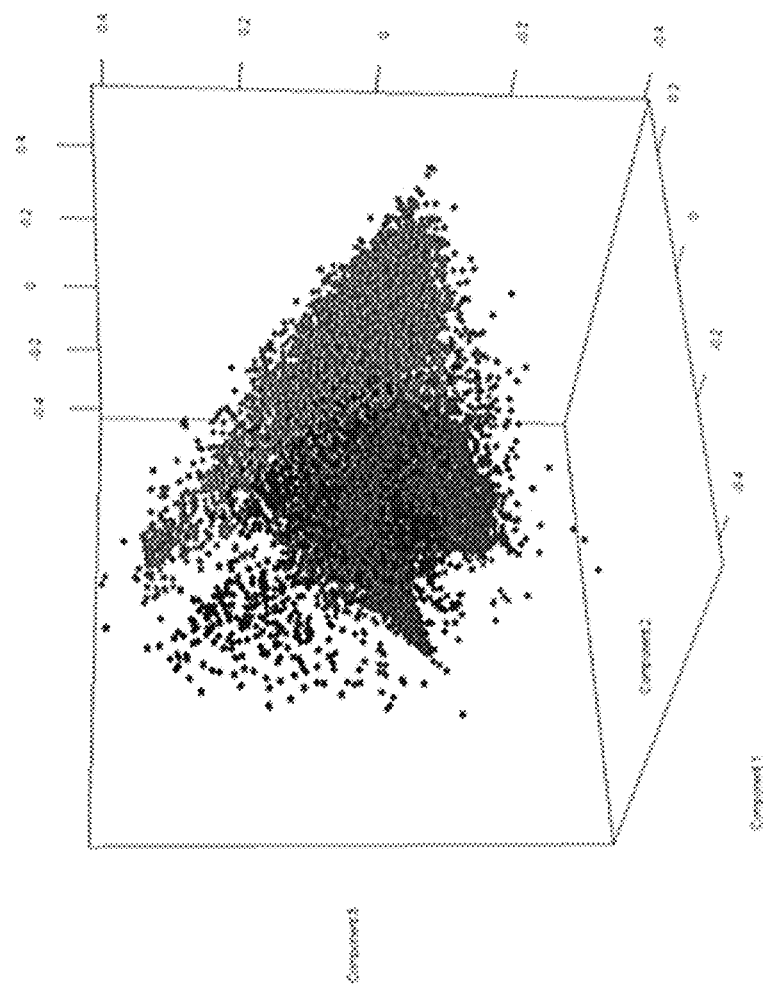
Figure 38B:
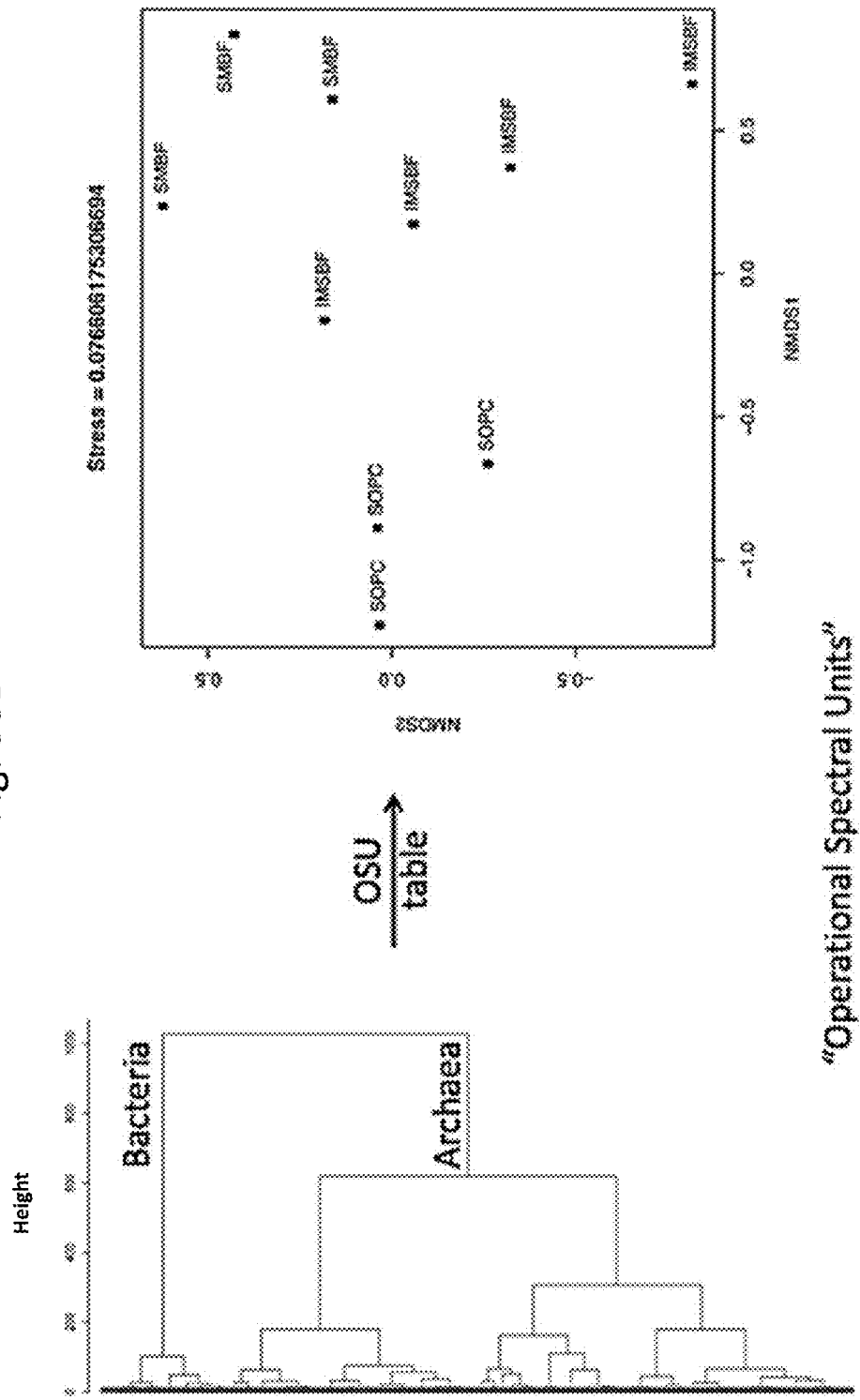

FIG. 36. Synchrotron radiation based Fourier transform infrared spectromicroscopy: Differentiation of Archaea and Bacteria based on lipid and carbohydrate signatures FIG. 37. Synchrotron radiation based Fourier transform infrared spectromicroscopy: Quantification of Archaeal and Bacterial biomass in samples FIGS. 38A and 38B. Microbial community profiling using SR-FTIR spectroscopy 31(a). 31(b).

Figure 39:
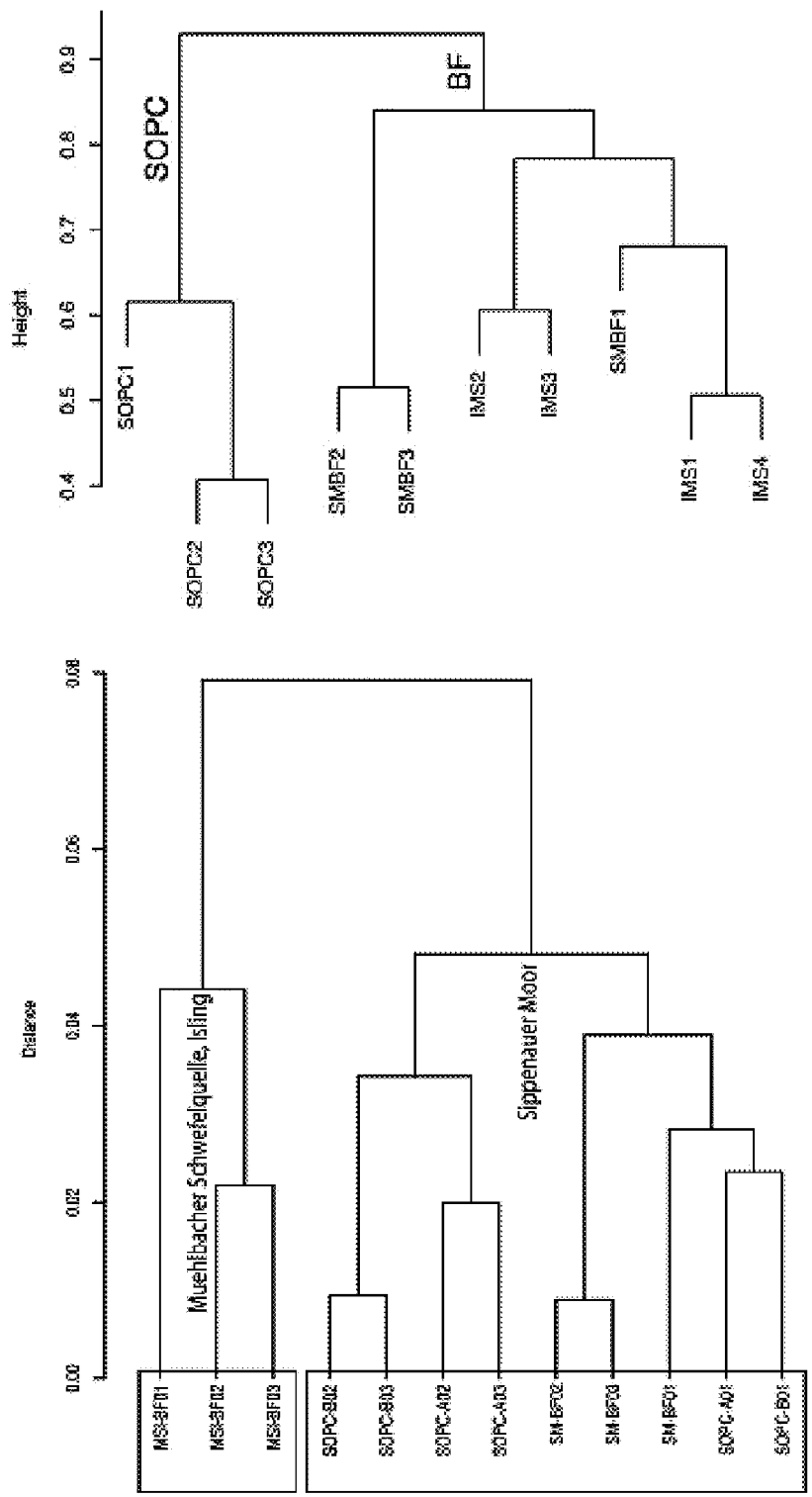

FIG. 39. PhyloChip G3™ versus SR-FTIR spectromicroscopy

Figure 40:
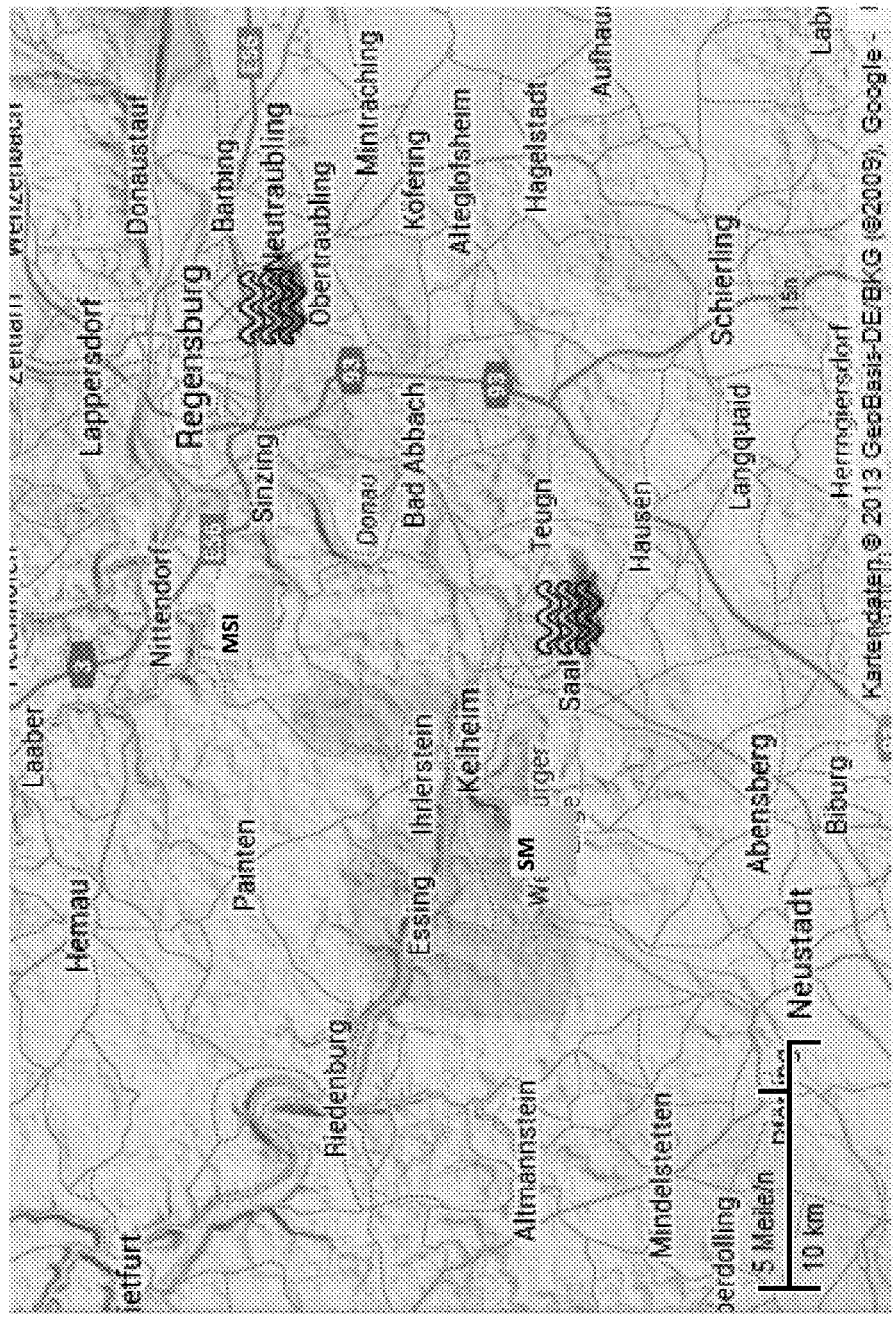

FIG. 40: Geographical map illustrating the sampling locations Sippenauer Moor (SM) and Muehlbacher Schwefelquelle, Isling (MSI) in their relative position to Regensburg and the Danube ("Donau").

FIG. 41A-C shows the conversion of biofilm to string-of-pearls community in the spring subsurface water. A: Biofilm; B: Intermediate; C: String-of-pearls community. Row 1: Schematic drawings. Orange: SM1 euryarchaeal cocci, Green: Filamentous, sulfide-oxidizing bacteria. Row 2: Micrographs and scanning electron micrograph (2B) of different stages. Row 3: FISH images of different stages (for IM samples please see Probst et al., 2013; Archaea orange (CY3), Bacteria green (RG)). A: SM-BF, showing high dominance of Archaea. B: Attachment of archaea to filamentous bacteria. C: String-of-pearls communities with large archaeal colony and bacterial mantle. It is proposed that attachment of SM1 Euryarchaeota to filamentous bacteria (B) mediates the transition from biofilm (A) to the string-of-pearls community (C). Scale bars: A3: 10 μm, B2: 1 μm B3: 10 mm, C3: 25 μm.

Figure 42B:
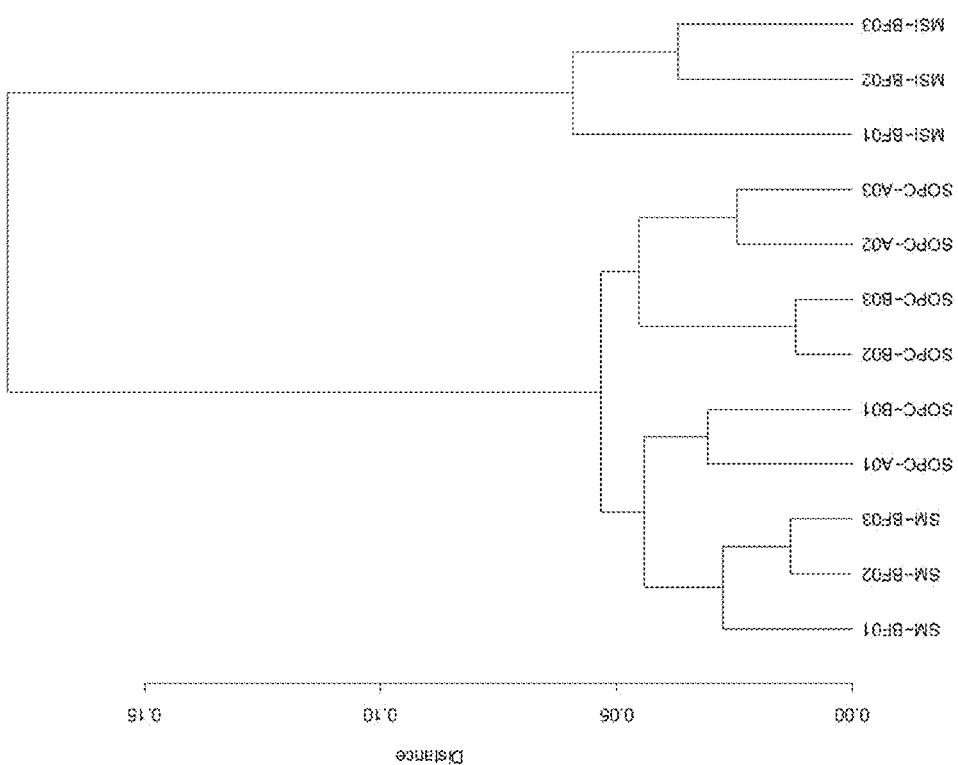

FIGS. 42A and 42B. EOTUs found to be significantly different between the two biofilm samples (#290). FIG. 42A: Heatmap displaying the 290 eOTUs (high resolution can be requested from the corresponding author: christine.moissl-eichinger@uni-r.de). Value=HybScore. FIG. 42B: Hierarchial clustering based on average neighbour (weighted UniFrac of 290 eOTUs) showing a separation of the microbiomes based on geographic location. Interestingly, SOPC samples which were not subject to significance filtering group together with SM-BF samples indicating similar microbiomes.

Figure 43:
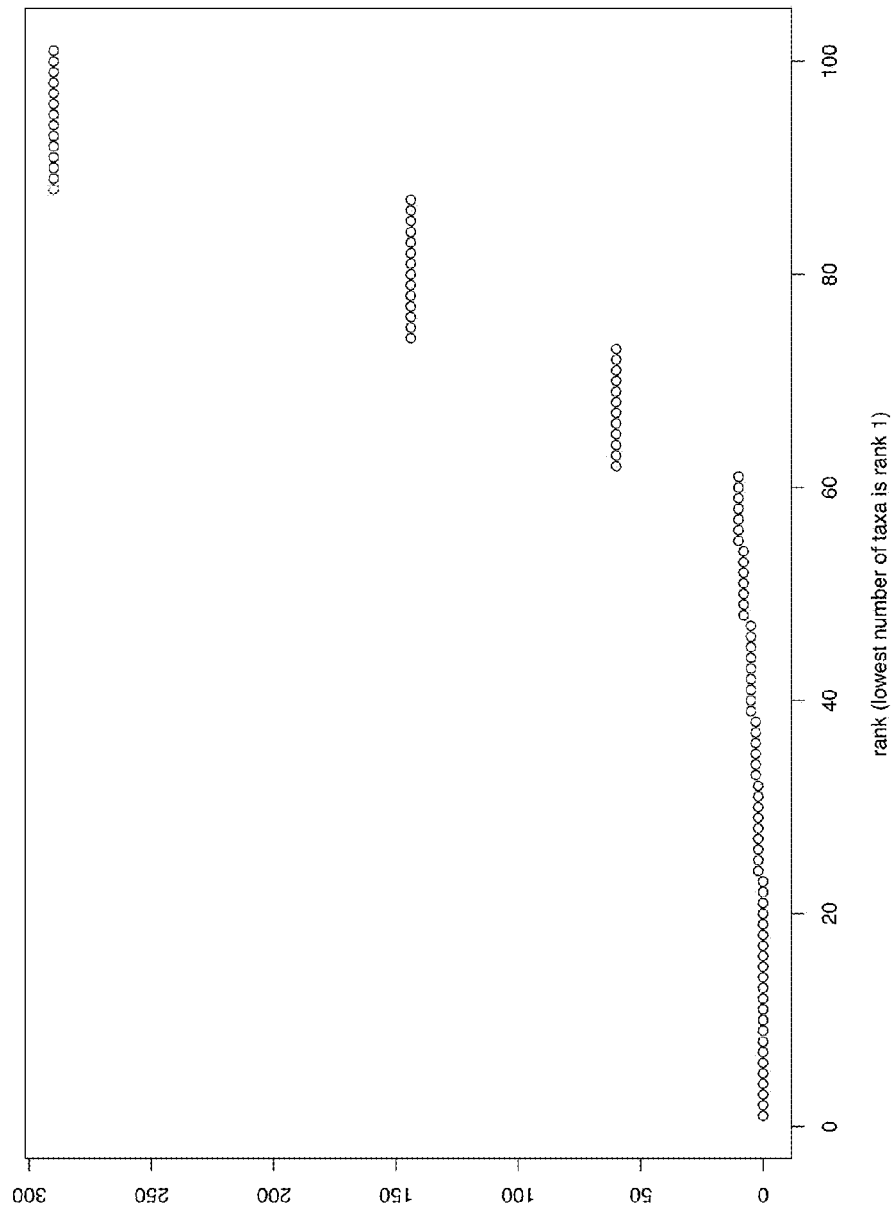

FIG. 43. Testing for false discovery detection of eOTUs. Permutation of sample group assignments for the Welch-test. In 100% of 100 permutations, equal or less than 290 eOTUs were identified. In approximately 20% of all permutations 290 eOTUs were identified. These 20% are expected since the possibility of creating the initial grouping after permutation is 20%. Consequently, the possibility of finding 290 eOTUs is unlikely due to chance. Red=true value. Y-axis displays the number of taxa passing the Welch-test.

Figure 44:
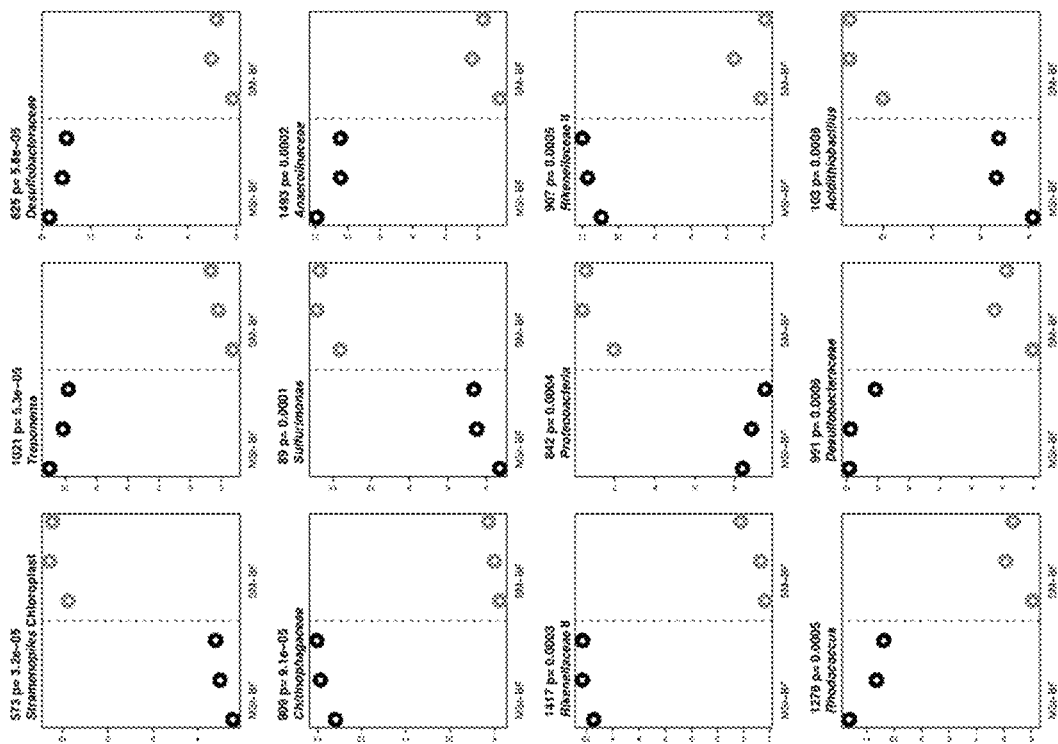

FIG. 44. Differences of the two biofilm-microbiomes: Top 12 of the most significant taxa found between the two biofilm types MSI-BF and SM-BF (Welch test; for details see FIG. 40).

Figure 45:
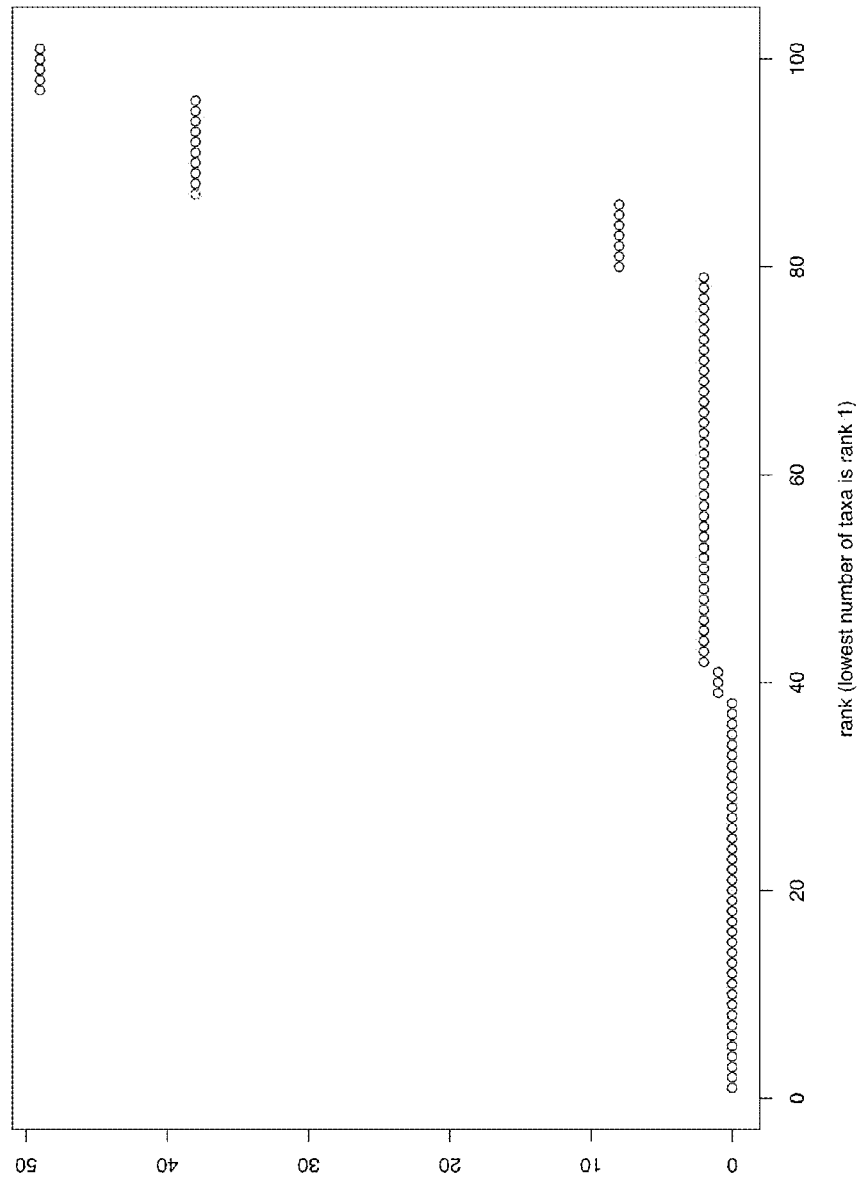

FIG. 45. Testing for false discovery detection of aggregated hybscores of families. Permutation of sample group assignments for the Welch-test. In approximately 5% of 100 permutations, more than 38 families passed the Welch test with a p-value lower than 0.05. Consequently, the possibility of finding 38 families is unlikely due to chance. Red=true value. Y-axis displays the number of taxa passing the Welch-test.

Figure 46:
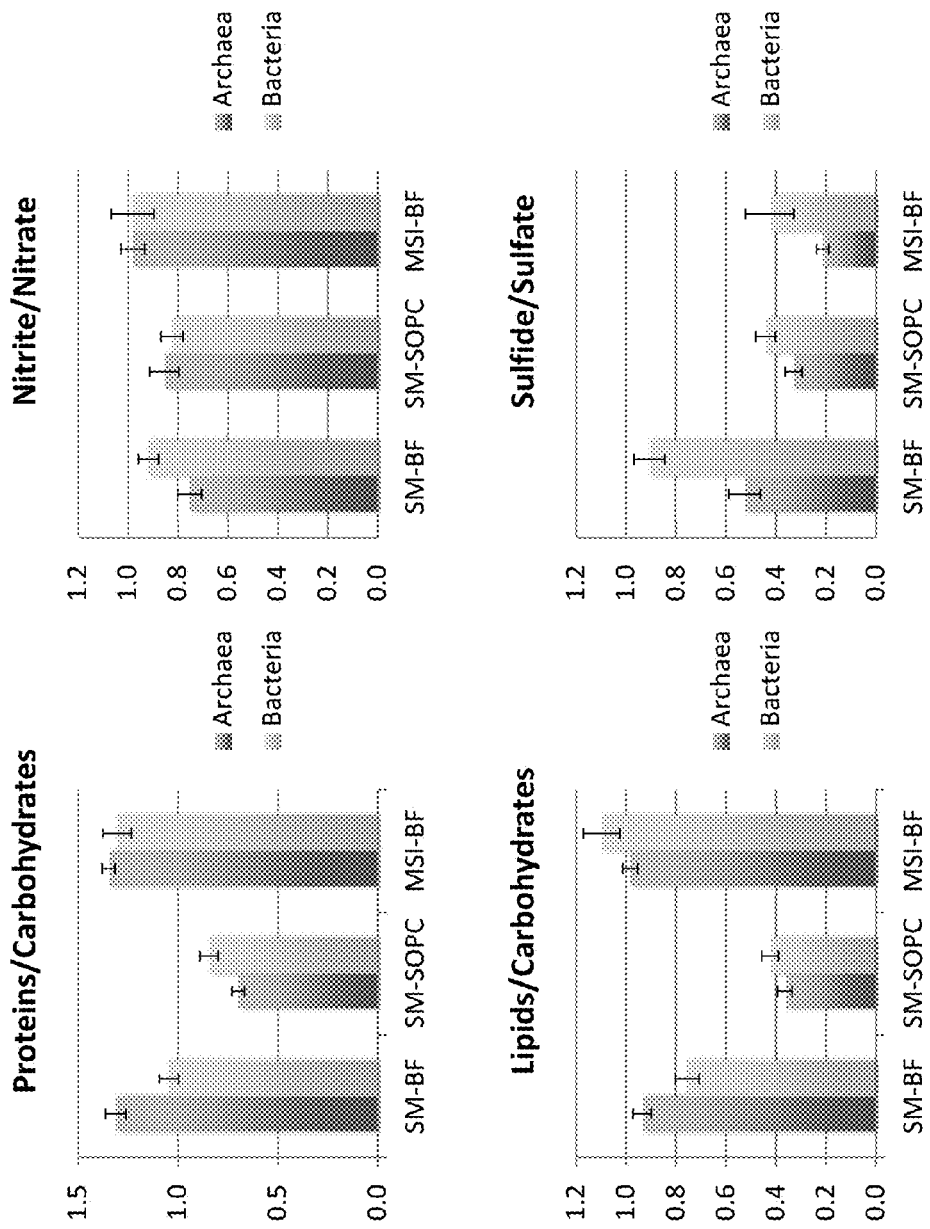

FIG. 46. Univariate analyses of SR-FTIR absorption bands of nitrogen and sulfur compounds shed light on the metabolic imprints in the immediate geochemical surroundings at the time of sampling. A comparison of the ratio of $NO_2^-$ to $NO_3^-$ ($NO_2^-/NO_3^-$) and the ratio of $S^{2-}$ to $SO_4^{2-}$ ($S^{2-}/SO_4^{2-}$) (S-FIG. 6) revealed spatial variations in the microbial reduction/oxidation processes.

Figure 47:
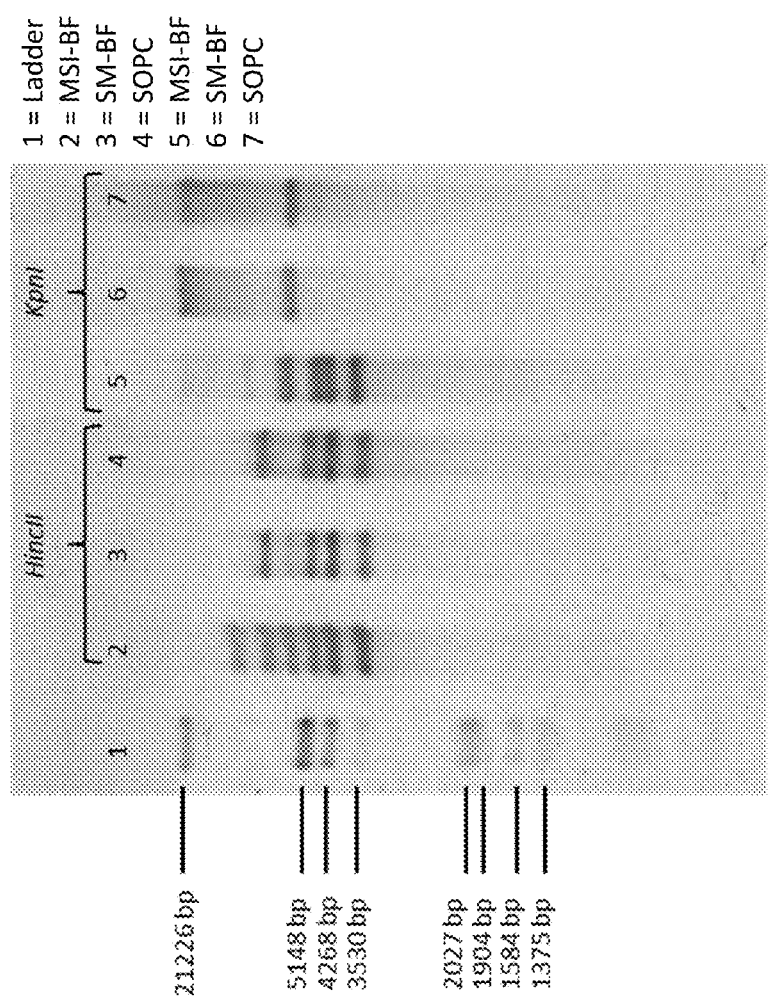

FIG. 47. Southern blotting of metagenomic DNA. Probes targeting the hamus gene were generated via amplification with the pili 1f and pili 2r primers (pili1f: 5'-CAGCAT-CAAAACAGGCGGGTGC-3' (SEQ ID NO: 1), pili2r: 5'-GTTCCTCTGAATTTGTATACGG-3') (SEQ ID NO: 2), and labeled with DIG High Prime as described in the manufacturer's instructions (Roche Diagnostics GmbH, Mannheim). 1 µg of metagenomic DNA of each biofilm type (Muehlbacher Schwefelquelle, Sippenauer Moor) was digested using the enzymes HindII and KpnI, individually, then electrophoresed and blotted on a nylon membrane. After hybridization with the hamus-specific probe, the membrane was blocked in TBST-B-buffer followed by an antibody reaction with Anti-Digoxygenin-AP conjugate (dilution up to 1:10000, Roche Diagnostics GmbH, Mannheim). The blot was washed thoroughly in 2×SSC (saline-sodium citrate buffer)/0.1% SDS at RT followed by a second washing step in 0.5×SSC/0.1% SDS at 68° C. The detection was carried out through NBT/BCIP (nitro blue tetrazolium/5-bromo-4-chloro-3-indolyl-phosphate) reaction.

Figure 48:
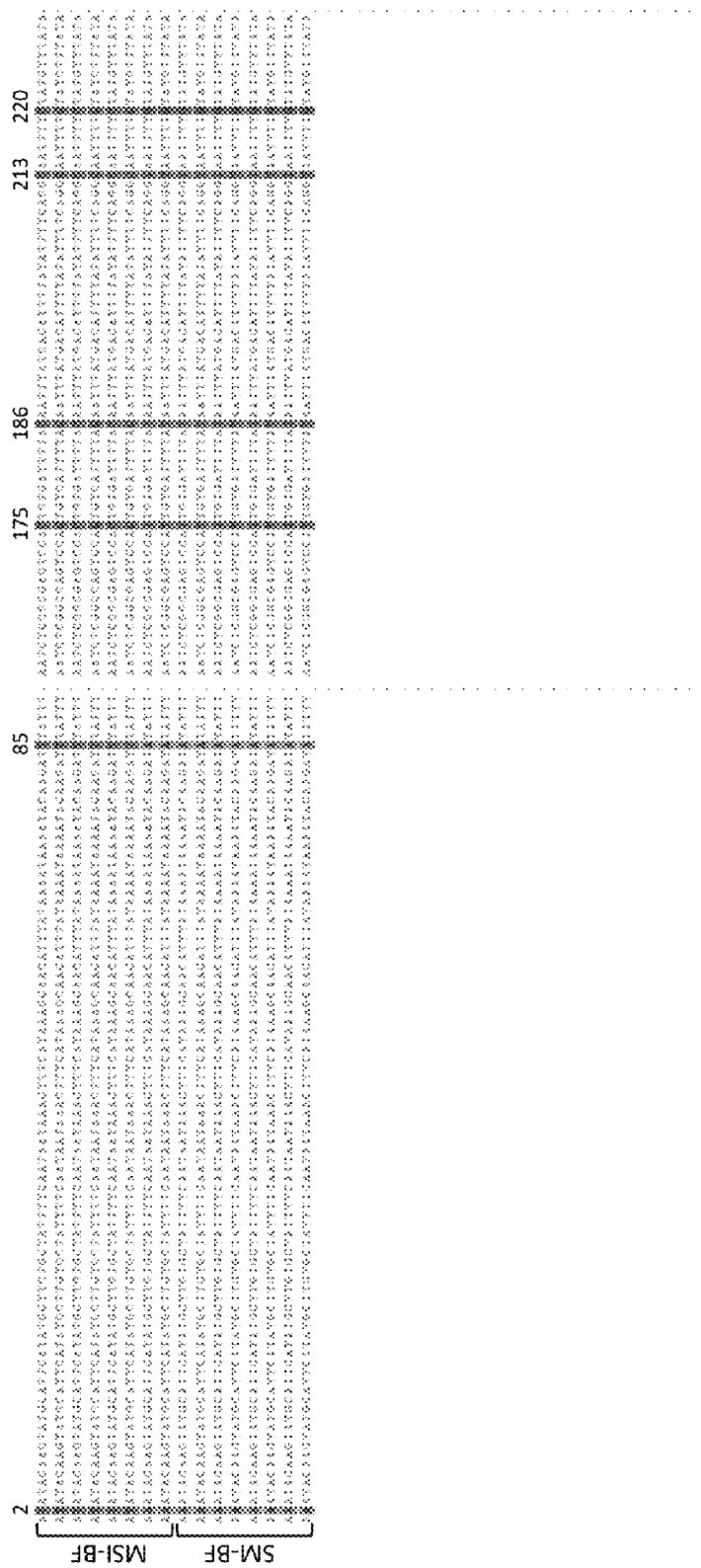

FIG. 48. Alignment of intergenic spacer regions of the SM1 Euryarchaon population from MSI-BF and SM-BF, which occurred at least twice in the analysis. Singletons are omitted, only 8 sequences per samples are given. The majority of MSI-BF sequences showed six SNPs compared to the majority of SM-BF sequences. Numbers give positions in the 375 character alignment.

METHODS

Parts of the archaeal rRNA operon were amplified from metagenomic biofilm DNA samples (MSI-BF and SM-BF) using 165-345af (5'-CGGGGYGCASCAGGCGCGAA-3' (SEQ ID NO: 3), Burggraf et al., 1992) and 23S-64R (5'-GCCNRGGCTTATCGCAGCTT-3' (SEQ ID NO: 4), Summit et al., 2001). Amplicons were cloned in *E. coli* (TOPO TA cloning kit, TOP 10' cells, Invitrogen) and 48 inserts per sample were bi-directionally sequenced (LGC Genomics, Berlin). Reverse sequences were trimmed to 16S rRNA genes and classified using the Naive Bayesian algorithm implemented in mother (Wang et al., 2007, Schloss et al., 2009) against an updated and 98%-clustered GreenGenes database (http://www.secondgenome.com/go/2011-greengenes-taxonomy/, McDonald et al., 2012) supplemented with known archaeal 16S rRNA gene sequences from sulfidic springs. Sequences classified as SM1 Euryarchaeota (Bootstrap >90) were then trimmed to the intergenic spacer region using the full reverse sequence. Multiple sequence alignments were generated using MUSCLE (Edgar et al., 2004).

Table 2. Overview of multivariate statistics performed on the bacterial microbiome and on the archaeal microbiome. Entire Microbiome is used for finding significantly eOTUs between sample groups (Welch-test). "+"=positive, "−" negative.

TABLE 1

Assignment of some bands frequencies in infrared and Raman Spectra

| Groups | Infrared wavenumber | Intensity | Raman shift | Intensity |
|---|---|---|---|---|
| $\upsilon(\equiv C-H))$ | 3300 $cm^{-1}$ | strong | 3300 $cm^{-1}$ | weak |
| $\upsilon(N-H)$ | 3300-3500 $cm^{-1}$ | medium | 3300-3500 $cm^{-1}$ | medium |
| $\upsilon(O-H)$ | 3100-3650 $cm^{-1}$ | strong | 3100-3650 $cm^{-1}$ | weak |
| $\upsilon(=(C-H))$ | 3000-3100 $cm^{-1}$ | medium | 3000-3100 $cm^{-1}$ | strong |
| $\upsilon(C-H)$ | 2800-3000 $cm^{-1}$ | strong | 2800-3000 $cm^{-1}$ | strong |
| $\upsilon(-S-H)$ | 2550-2600 $cm^{-1}$ | weak | 2550-2600 $cm^{-1}$ | strong |
| $\upsilon(C\equiv N)$ | 2210-2260 $cm^{-1}$ | strong | 2220-2255 $cm^{-1}$ | medium |
| $\upsilon(C\equiv C)$ | 2100-2260 $cm^{-1}$ | weak | 2100-2250 $cm^{-1}$ | strong |
| $\upsilon(C=O)$ | 1665-1760 $cm^{-1}$ | strong | 1680-1820 $cm^{-1}$ | medium |
| $\delta(H_2O)$ | 1642 $cm^{-1}$ | strong | 1640 $cm^{-1}$ | weak & broad |
| $\upsilon(-N-C=O)$ | 1480-1700 $cm^{-1}$ | strong | 1210-1300 $cm^{-1}$ | strong |
| $\upsilon(C=N)$ | 1640-1690 $cm^{-1}$ | medium | 1610-1680 $cm^{-1}$ | strong |
| $\upsilon(CC)_{aromatic\ ring\ chain\ vibrations}$ | 1585-1600 $cm^{-1}$ | medium | 1580-1600 $cm^{-1}$ | strong |
| $\upsilon(N=N)_{aliphatic}$ | — | — | 1550-1580 $cm^{-1}$ | medium |
| $\upsilon(C-(NO_2))_{asym}$ | 1475-1550 $cm^{-1}$ | strong | 1530-1590 $cm^{-1}$ | medium |
| $\upsilon(C=C)$ | 1600-1680 $cm^{-1}$ | weak | 1500-1900 $cm^{-1}$ | strong |
| $\upsilon(N=N)_{aromatic}$ | — | — | 1410-1440 $cm^{-1}$ | medium |
| $\delta(CH_2)\delta(CH_3)_{asym}$ | 1450-1470 $cm^{-1}$ | medium | 1400-1470 $cm^{-1}$ | medium |
| $\delta(CH_2)\delta(CH_3)_{asym}$ | 1450-1470 $cm^{-1}$ | medium | 1400-1470 $cm^{-1}$ | medium |
| $\delta(CH_3)$ | 1350-1370 $cm^{-1}$ | strong | 1380 $cm^{-1}$ | medium |
| $\upsilon(C-(NO_2))$ | 1290-1360 $cm^{-1}$ | medium | 1340-1380 $cm^{-1}$ | strong |
| | | | 1000 $cm^{-1}$ | Strong/medium |
| $\upsilon(CC)$ alicyclic, aliphatic chain vibrations | 1610-1680 $cm^{-1}$ | medium | 600-1300 $cm^{-1}$ | medium |
| $\upsilon(O-O)$ | — | — | 845-900 $cm^{-1}$ | strong |
| $\upsilon(C-O-C)$ | 1000-1320 $cm^{-1}$ | weak | 800-970 $cm^{-1}$ | medium |
| $\upsilon(C-O-C)_{asym}$ | 1000-1320 $cm^{-1}$ | strong | 1060-1150 $cm^{-1}$ | weak |
| $\upsilon(C-Cl)$ | 550-850 $cm^{-1}$ | medium | 550-800 $cm^{-1}$ | strong |

BRIEF DESCRIPTION OF THE SEQUENCES

SEQ ID NO: 1 is pili 1f primer sequence for generating probes targeting the hamus gene via amplification.

SEQ ID NO: 2 is pili 2r primer sequence for generating probes targeting the hamus gene via amplification.

SEQ ID NO: 3 is 165-345af primer sequence for amplifying archael rRNA operon from metagenomic biofilm DNA samples.

SEQ ID NO: 4 is 23S-64R primer sequence for amplifying archael rRNA operon from metagenomic biofilm DNA samples.

SEQ ID NO: 5 is 1406ur primer sequence for amplification of archaeal 16S rRNA genes.

SEQ ID NO: 6 is a polynucleotide probe that was identified to match with only seven different archaeal sequences in the database.

DETAILED DESCRIPTION OF THE PREFERRED EMBODIMENT

Introduction

In various embodiments, a method, described herein and termed Microbial Community Screening and Profiling (MCSP), employs multi-dimensional analysis and is enabled by non-destructive and label-free techniques which allow for follow-up complementary analytical techniques to be performed on the same sample for such multidimensional analysis. We link phylogenetic diversity information with the spatial distribution of chemical and metabolic compounds by combining three different state-of-the-art methods: PhyloChip G3 DNA microarray technology, fluorescence in situ hybridization (FISH) and synchrotron radiation-based Fourier transform infrared (SR-FTIR) spectromicroscopy. In the area of microbial community profiling, the results of PhyloChip and FISH technologies provide evidence for selective enrichment of certain microbial members, which can be confirmed by the detection of functional gene expression via quantitative PCR and sequence-based analyses. We further established a differentiation of archaeal and bacterial cells by SR-FTIR based on typical lipid and carbohydrate signatures.

Herein we describe a rapid and non-destructive molecular method capable of obtaining microbial information over the course of various biological stages directly from the sample without any intermediate sample preparation processes such as nucleic acid/protein/lipid extraction and purification. In various embodiments, the methods described herein will enable rapid and non-destructive (1) identification, (2) quantification of microorganism abundance (e.g. Archaea versus Bacteria) within microbial communities, and (3) elucidation of entire community functional relationships at a chemical level.

In various embodiments, the methods comprise steps for chemical and biological analyses and measurements on the same sample utilizing non-invasive and label-free infrared (IR) imaging techniques, this being more productive with respect to the number of analyses performed per sample. Furthermore infrared imaging provides information regarding the spatial and chemical distribution of microorganisms in a microbial or cellular community sample as well as their metabolites and biogeochemial components.

DESCRIPTIONS OF THE EMBODIMENTS

Figure 6:
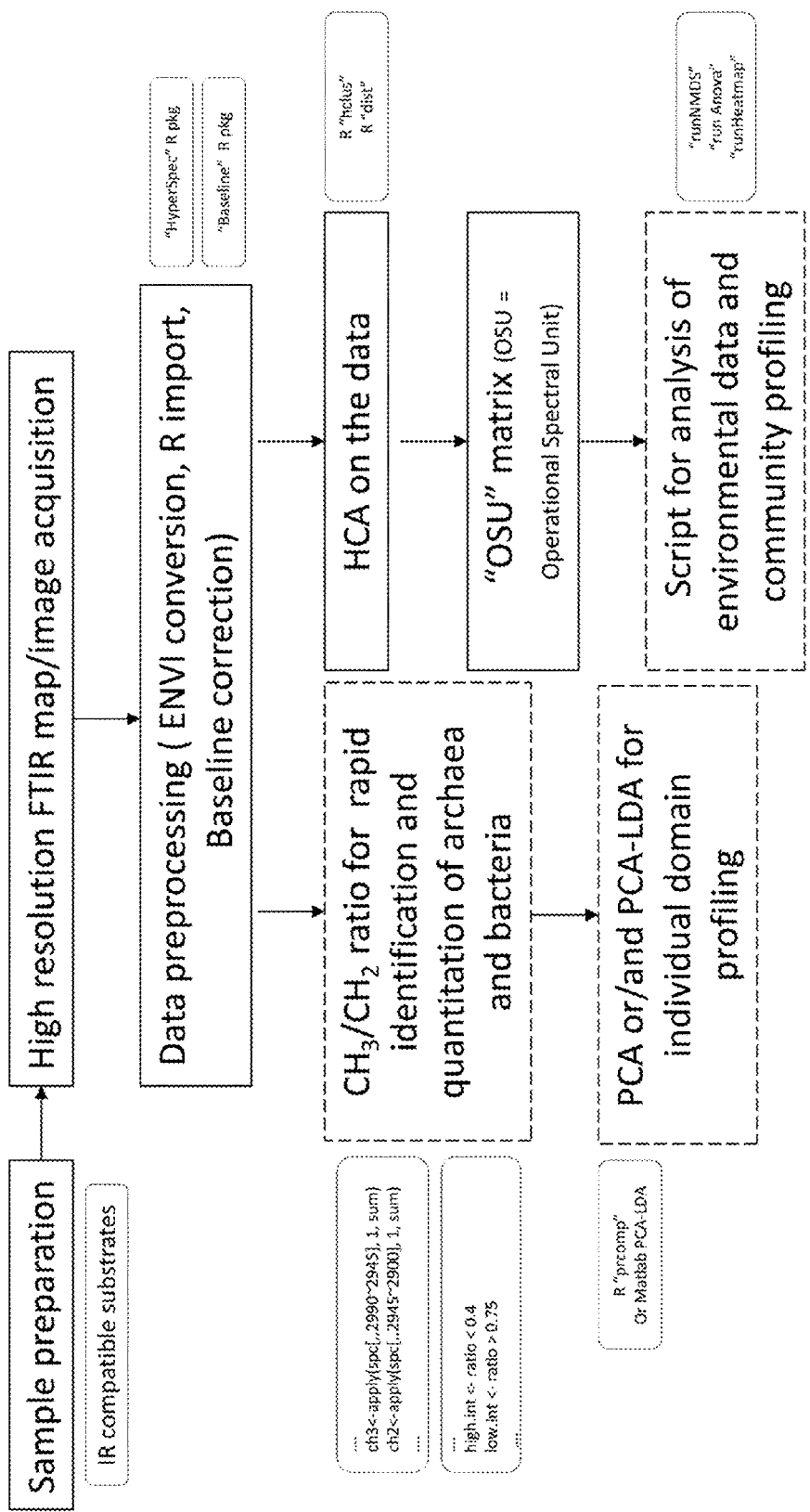
FIG. 6. A schematic diagram of the invention. The procedure of the invention has three main steps as indicated by "dashed" boxes.

In various embodiments, a method comprising the steps as depicted in the flow chart of FIG. 6. A biological sample is prepared and provided on an IR compatible substrate for sample image and detection acquisition using an IR spectromicrosopy system. A high resolution infrared map and image is acquired. The data from the infrared map and image are stored and undergo preprocessing using statistical tools in the art including but not limited, ENVI conversion, R import or baseline correction or their equivalents. Then spectral analysis and the biological analyses are conducted, concurrently, in parallel or sequentially. Spectral analysis is conducted on the processed spectral data. The sample then goes on to undergo other biological analyses including but not limited to, genomic sequencing, probe hybridization, phylogenetic analysis, mass spectrometry, etc.

In various embodiments, the sample may be a heterogeneous or homogeneous mixture of cell types from any source including but not limited to, microbial community sample, a biofilm, organism, tissue, biomass, biological fluid sample, environmental samples, etc. In various embodiments, analysis of vibrational spectra with this method can be used to profile community relationships within environmental samples containing, but not limited to, bacteria, archaea, fungi, spores, algae and plant cells.

In one embodiment, this method can be used to profile and characterize micro-biome harvested from hosts belonging to the Animalia Kingdom, including but not limited sample coming from human gut, intestines, airway, mouth, skin or other human body cavity or bodily fluid including but not limited to skin, blood, sputum, or fecal samples.

In other embodiments, the IR compatible substrate is either coated or comprised of an IR compatible material such as a metal or semiconductor material. In one embodiment, the substrate is coated with an IR-reflective coating such as a gold coating. The coating, when needed, is preferably a thin layer. In one embodiment, the coating is about 50-1000 Å thick. In another embodiment, the reflective surface is infrared transparent or semi-transparent material, such diamond or ZnSe. The substrate may be any shape or configuration that is compatible with the IR microscopy system. In another embodiment, the substrate may be a grid, e.g., a Cryo-EM or cryo-TEM grid.

The infrared sources can be thermal emission sources, laser sources, sun, or accelerator-based sources (including synchrotrons). In some embodiments, broad-band synchrotron infrared spectroscopic measurement to evaluate the heterogeneity of the microbial communities. In other embodiments, benchtop infrared spectral imagers may be suitable. In some embodiments the infrared measurements are fully automated.

The UV/VIS sources for Raman spectral imaging can be monochromatic laser sources, sun, or accelerator-based sources (free electron lasers). In some embodiments, plasmonic enhancement, pattern or nearfield techniques are envisioned for high spatial resolution measurement to evaluate the heterogeneity of the microbial communities. In some embodiments the Raman measurements are fully automated.

In various embodiments, the two supervised parameters used for the analytical procedure are the spectral regions of interest (sROI) and the threshold for $CH_3/CH_2$ ratio. The selected sROI are, but not limited to, in the lipid region (2800-3100 $cm^{-1}$), the carbohydrate region (1000-1280 $cm^{-1}$), or the molecular fingerprint region (1480-650 $cm^{-1}$).

In some embodiments, the data are infrared spectra collected via transmission mode or transflectance mode (also called reflectance mode, or double-pass transmittance mode). In another embodiments, the data are Raman spectra. They will require data preprocessing to correct the baseline and to remove measurement artifacts such as resonance Mie scattering, electronic field standing waves and fringing effects for infrared spectra, and autofluorescence for Raman spectra.

In one specific embodiment, the data will be analyzed in a supervised manner and a threshold value of $CH_3/CH_2$ or $CH_2/CH_3$ will be selected to quantify the relative abundance of archaeal and bacterial communities inside a sample. In some embodiments, the threshold value is 0.72 to 0.8 for $CH_3/CH_2$, and 1.38 to 1.25 for $CH_2/CH_3$.

In another embodiment, the data will be analyzed in an unsupervised manner. This procedure produces data that can be used for a discriminant analysis of microbiome based on spectral profiling in the pre-selected sROI using multivariate statistics including Principal Component Analysis (PCA) or Principal Component-Linear Discriminant Analysis (PC-LDA).

In some embodiments, the preprocessed data will be analyzed using unsupervised similarity analysis using hierarchical clustering first based on Euclidean distances, then grouped the distances using the Ward minimum variance methods. Then using the cluster "membership", the correlation matrix containing all the Operational Spectral Units (OSUs) was generated. This matrix was subjected to ordination analyses such as NMDS (Non-metric multidimensional scaling) or PCoA (Principal Coordinate Analysis). Statistical significance of the results will be tested using ADONIS.

Spectral Analysis using IR Spectromicroscopy

IR spectromicroscopy and/or visible microscopy is conducted on the sample area. Infrared spectromicroscopy is a non-invasive and label-free chemical imaging technology that provides molecular information at micrometer spatial resolution (Carr et al., 1995; Dumas et al., 2009). Infrared spectromicroscopy of live microbial cells takes advantage of the well-known sensitivity of the mid-infrared spectroscopy to chemical functional groups in molecules and their conformations, and the convenience of a microscope to locate areas for molecular and composition analysis. Any infrared photon source can be used in conjunction with the present apparatus, including a broad band synchrotron light source, a single or multi wavelength source.

In various embodiments, IR reflectance spectroscopy can be carried out using Synchotron Radiation-based Fourier Transform Infrared Microscopy (SR-FTIR) as described in Probst A J, Holman H Y, DeSantis T Z, Andersen G L, Birarda G, Bechtel H A, Piceno Y M, Sonnleitner M, Venkateswaran K, Moissl-Eichinger C., "Tackling the minority: sulfate-reducing bacteria in an archaea-dominated subsurface biofilm," *ISME J.* 2013 March; 7(3):635-51doi: 10.1038/ismej.2012.133. Epub 2012 Nov. 22; Holman H Y, Bechtel H A, Hao Z, Martin M C, "Synchrotron IR spectromicroscopy: chemistry of living cells," *Anal Chem.* 2010 Nov. 1; 82(21):8757-65. doi: 10.1021/ac100991d. Epub 2010 Sep. 14; Chen L, Holman H Y, Hao Z, Bechtel H A, Martin M C, Wu C, Chu S, "Synchrotron infrared measurements of protein phosphorylation in living single PC12 cells during neuronal differentiation," *Anal Chem.* 2012 May 1; 84(9):4118-25. doi: 10.1021/ac300308x. Epub 2012 Apr. 18, all of which are hereby incorporated by reference in their entirety. SR-FT LR takes advantage of three technologies: (i) the well-known sensitivity of infrared spectroscopy to the bond vibration frequencies in a molecule for determining molecular functional groups, (ii) the convenience of a light microscope to locate areas for molecular and composition analysis, and (iii) the 100- to 1000-fold increase in signal-to-noise provided by a bright SR-based infrared light source. Using photons in the mid-infrared region (~2.5 to ~15.5 μm wavelength, or ~4000 to ~650 wavenumber in cm−1), SR-FTIR spectromicroscopy has been successfully used to characterize microbial activities in geological materials and in both hydrated and dried biofilms (Holman et al., 2009; Hazen et al., 2010; Holman et al., 2010), in spite of the limitation that some signals may be ambiguous.

The detailed spectrum of a microbial cell is analyzed by combination of conventional interpretations of measured Fourier transform infrared (FTIR) spectra with modern chemometrics (i.e., the application of machine learning as well as statistical and other mathematical techniques to analytical chemical data). In addition to detecting the biochemical groups within cellular components, one can also reliably identify and discriminate bacteria strains in a sample within the same genus. Other successful applications of infrared spectroscopy with chemometrics include but are not limited to, monitoring the population dynamics of microorganisms, characterizing microbial heterogeneity inside a biofilm, determining quantitatively the biodegradable polymer poly(b-hydroxybutyrate) inside bacteria, following structural changes inside bacterial cells, and footprinting metabolites.

In a preferred embodiment, a system is equipped with a Fourier transform infrared (FTIR) spectrometer, an infrared microscope, and a microscope stage incubator to maintain the physiological state of microbial cells. Since the infrared beam does not induce any detectable side-effects in live cells, it allows one to probe chemical and structural changes, and the intermediates along the reaction pathway of processes in their natural state. For example, the technique enables the simultaneous real-time observation of chemical and conformational changes in biologically important molecules such as DNA, lipids, proteins and carbohydrates in living bacterial cells during a stress-response event, or in environmentally important molecules such as chromates during bioremediation. See methods described in Holman, H.-Y. N., et al., *Real-time characterization of biogeochemical reduction of Cr(VI) on basalt surfaces by SR-FTIR imaging*. Geomicrobiology Journal, 1999. 16(4): p. 307-324, and U.S. Pat. Pub. No. 2011-0223654, both of which are hereby incorporated by reference.

The fundamental measurement detected by a detector (e.g., mercury-cadmium-telluride detector), is a spectrum of infrared absorbance in the sample as a function of the wavelength of infrared light (typically expressed in units of wavenumbers, $cm^{-1}$). Atoms inside the sample vibrate with characteristic frequencies governed by their chemical bonding environment; the measured frequencies of these vibrations (the sample absorbs infrared light when the frequency of the light exactly matches the frequency of the vibration) are unique for every molecular configuration. Thus each mid-infrared spectrum of a biological sample represents a "fingerprint" for the presence of chemical functional groups in a molecule within biological samples. See Table 1 showing the fingerprint spectral regions and the spectral shifts that are observed that represent fingerprint regions. Infrared spectra can be collected over a wide wavenumber range such as from 4000 to 650 $cm^{-1}$. The spectrum for each sampling location at each time point will contain at least 8480 data points, each representing an absorbance value at a particular wavelength Methods for maintenance and for carrying monitoring of live cells using infrared spectroscopy is described in the following references, which are hereby incorporated by reference: Holman, H-Y. N., and M. C. Martin. *Synchrotron radiation infrared spectromicroscopy: a non-invasive molecular probe for biogeochemical processes*. Advances in Agronomy, 90: 79-127, 2006; Holman, H. Y. N., et al., *Catalysis of PAH biodegradation by humic acid shown in synchrotron infrared studies*. Environmental Science & Technology, 2002. 36(6): p. 1276-1280; Holman, H.-Y. N., et al., *Low-dose responses to 2,3,7,8-tetrachlorodibenzo-p-dioxin in single living human cells measured by synchrotron infrared spectromicroscopy*. Environmental Science and Technology, 2000. 34(12): p. 2513-2517; and Holman, H.-Y. N., et al., *Real-time characterization of biogeochemical reduction of Cr(VI) on basalt surfaces by SR-FTIR imaging*. Geomicrobiology Journal, 1999. 16(4): p. 307-324.

A computer and software are provided to perform a Fourier transform on the measured interferogram to obtain an infrared spectrum for each sample location and removal of the characteristic $CO_2$ peaks at 683 to 656 and 2403 to 2272 $cm^{-1}$, and the water vapor fingerprints from the spectra. These data can be imported into spectral analysis programs such as the Chemometrics Toolbox in MATLAB for chemometric analysis. The resulting reflectance spectra can be analyzed and the fingerprint spectra can be compared to that of a control. Changes in the spectra can be used to detect the presence or effect of various experimental or environmental conditions on live cells, microorganisms, biomolecules and other biological systems.

In various embodiments, the $CH_3/CH_2$ ratio for rapid identification and quantitation of archaea and bacteria is determined and the results for the sample cells are compared. The two infrared parameters used for the analytical procedure are the spectral regions of interest (sROI) and the threshold for $CH_3/CH_2$ ratio. The selected sROI were the lipid region (2800-3100 $cm^{-1}$) and the carbohydrate region (1000-1280 $cm^{-1}$). In some embodiments, to distinguish bacteria from archaea, spectral features of their lipids in the C—H region due to differences in cell envelope compositions are compared (See FIGS. 1 and 2). The methods were also described in *ISME Journal* 7, 635-651 (March 2013) doi:10.1038/ismej.2012.133. Epub 2012 Nov. 22, hereby incorporated by reference in its entirety. Reference spectra from pure model archaea and bacteria are collected and analyzed using Principal Component Analysis (PCA) or Principal Component—Linear Discriminant Analysis (PC-LDA) (FIG. 2A).

In various embodiments, freshly harvested samples are gently air dried onto gold-coated copper disks. Although drying affects the three-dimensional structure of the biofilms, prior microscopy experiments with other biofilms suggest that the two-dimensional structure is largely unaffected. Therefore, the measured spatial distribution of Bacteria, Archaea and the biogeochemical features could represent their native two-dimensional distribution within the biofilm. All IR spectromicroscopy measurements are performed in transflectance mode. In some embodiments, the beam can be transmitted through the sample, reflected off the gold-coated upper surface and then transmitted through the sample a second time before striking the detector. It is recommended that multiple scans are conducted for each spectrum such that each spectrum is an average of multiple (e.g., 4-8) scans at a particular spectral resolution. Background spectra should be obtained on the cell-free area of the substrate.

For each IR imaging measurement, the micron field-of-view for the sample can be divided into equal-sized area pixels before raster scanning. The resulting data cube, which consists of position-associated FTIR spectra, is subjected to data preprocessing and processing calculations, including spectrum baseline removal, for example, using computer-implemented data processing software and environments such as Thermo Scientific Omnic version 7.3 (Thermo Scientific, Madison, Wis., USA) and Matlab (MathWorks, Nattick, Mass., USA), and major packages and commands used in the R programming environment.

The absorption spectra are then subjected to univariate and unsupervised multiple curve resolution (MCR) image analyses. The univariate approach, which integrates infrared absorbance of an individual peak of interest, relates the absorbance intensity to the relative concentration of a particular chemical component through the Beer-Lambert law. The unsupervised MCR approach, on the other hand, is based on the Principal Component Analysis (PCA) of the entire fingerprint region (1800-700 $cm^{-1}$) and of the C—H region (3100-2800 $cm^{-1}$) instead of individual peaks. MCR analysis of SR-FTIR spectra is applied to reveal the distributions of Archaea, Bacteria and chemical variations in the biofilms, which are hidden in the univariate approach. In some embodiments, the unsupervised MCR analysis is performed with non-negative constraints on both concentration and spectral values (Budevska et al., 2003).

In various embodiments, several components are selected based on the 95% percentage of variance explained and on the spectral features of the loading plot. LDA can be then applied to maximize the 'inter-class' variance over the 'intra-class' variance of the factors, Visualization of the multivariate analysis results in the form of score plots and cluster vector plots (See FIGS. 2A and 2B). In the Examples, score plots were three-dimensional plots where the first three PC-LDA components were the x-, y- and z-axes; the nearness between classes (clusters) indicates the similarity, whereas the distance between classes implies dissimilarity.

Detailed analyses (FIGS. 2A and 2B) revealed that, in spite of the significant variations in the cell envelope (including cell wall) compositions, Bacteria can be distinguished from Archaea solely by comparing spectral features of their lipids in the C—H regions (3100-2800 $cm^{-1}$). As expected, bacterial membrane lipids consist of fatty acids with long alkylic (—CH2-) chains which have only one to two terminal methyl (CH3-) groups. In contrast, archaeal membrane lipids generally consist of branched and saturated hydrocarbon isoprene, and therefore relatively less CH2- and more CH3- groups (Mancuso et al., 1986). Our earlier study showed that the SM1 Euryarchaeon possesses a typical CH3-rich lipid (archaeol, Rudolph, 2003). In this context, the ratio of CH2 to CH3 could be used to detect Bacteria in an Archaea-dominated biofilm (FIGS. 9a and 9b).

In some embodiments, the univariate spectral analysis of the membrane methyl (—$CH_3$) to the methylene (—$CH_2$) absorbance ratio is used to designate the spectral fingerprints of archaeal or bacterial members of the sample. Such methods are also described in Example 2.

Further Compatible Biological Analysis

The abundance of archaea and bacteria within microbial communities from each environmental biotope obtained via vibrational spectromicroscopy can be confirmed by cell counting after Fluorescence In-Situ Hybridization (FISH) staining, PhyloChip G3 analysis and qPCR analyses (FIG. 3).

In some embodiments, further analysis of microbial community members may be carried out using FISH to detect genomic markers. For example, one can create probes that hybridize to the known gene regions in various members. Probes can be created by methods known in the art based upon the sequences of genes. For example, 500 Kbp contiguous spanning regions of high level amplification at a particular chromosomal region in an organism that are most strongly associated with specific functions can be detected, avoiding regions of the genome that harbor low level repeats that may not be fully blocked during hybridization content thereby giving false positive hybridization signals. DNA from the probe generated can be produced and labeled with known fluorescent dyes, such as Spectrum Orange, Spectrum Green and Spectrum Aqua (Vysis, Inc.) to produce hybridization probes for detection of amplification at the test loci. In another embodiment, the in situ hybridization methods of identifying probes described in U.S. Pat. No. 6,268, 184, which is hereby incorporated by reference, is used. Methods of preparing probes are well known to those of skill in the art (see, e.g. Sambrook et al., Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)).

In another embodiment, the method further comprises using an array to determine or detect presence of microbial communities. An array approach using an array such as the PhyloChip microarray to source identification relies on the presence of dozens or hundreds of taxa, rather than one or a few taxa, to determine the occurrence of various microbial sources. In some embodiments, the array analysis uses commercially available microarrays such as the PhyloChip G3 (Second Genome, S. San Francisco, Calif.) and its analysis, see U.S. Pat. Pub. No. US20120165215, hereby incorporated by reference in their entirety. The PhyloChip is a DNA microarray unique in its ability to identify multiple bacterial species and organisms from complex microbial samples and relies on detection of unique taxa in the 16S rRNA gene region among other genes. 16S rRNA gene composition is strongly source-specific and can be used to differentiate between or among various microbial communities. The use of an oligonucleotide microarray that targets the 16S rRNA gene pool of the bacterial community can serve as a rapid method for identifying the members of the microbial community in the sample.

Briefly, sample PCR products are prepared and hybridized to the microarray as recommended by the manufacturer's instructions or using methods known in the art. Hybridization is detected, in some embodiments, by fluorescence detection. Analysis procedures for fluorescent image files is carried out. For example, PhyloChip analysis is described in detail in the supplemental material of Hazen et al., Deep-Sea Oil Plume Enriches Indigenous Oil-Degrading Bacteria. *Science* 2010, 330, (6001), 204-208. Briefly, each individual array feature occupied approximately 8×8 pixels in the image file corresponding to a single probe 25mer on the surface. Probe intensities were background-subtracted and scaled to quantitative standards (non-16S rRNA gene spike-ins) as previously described in DeSantis, T. Z.; Brodie, E. L.; Moberg, J. P.; Zubieta, I. X.; Piceno, Y. M.; Andersen, G. L., High-density universal 16S rRNA microarray analysis reveals broader diversity than typical clone library when sampling the environment. *Microbial Ecology* 2007, 53, 371-383. Presence/absence calling of each microbial taxon (operational taxonomic unit—OTU) is based on positive hybridization of multiple probes that correspond to an OTU (average of 37 probes/OTU). Differences in mean hybridization intensity (fluorescence) of an OTU probe set among different PhyloChips reflected differences in the relative abundance of the OTU (DeSantis, T. Z.; Brodie, E. L.; Moberg, J. P.; Zubieta, I. X.; Piceno, Y. M.; Andersen, G. L., High-density universal 16S rRNA microarray analysis reveals broader diversity than typical clone library when sampling the environment. *Microbial Ecology* 2007, 53, 371-383). PhyloChip results are output as lists of detected OTUs and their hybridization scores, with associated taxonomic information and references to represented sequences in public 16S rRNA gene repositories (greengenes.lbl.gov). Hybridization results are reduced to a community profile from each PhyloChip assay to a format useful for multivariate statistics consisting of log transformed hybridization intensity values for all detected OTUs. Inter-profile dissimilarity is calculated, e.g., with the Bray-Curtis metric, and the resulting distance matrix can be analyzed with hierarchical cluster analysis and non-metric multidimensional scaling (NMDS) ordination using known statistical methods, e.g., the Primer v.6.1.13 statistical package. Analysis of Similarity (ANOSIM) can be used to test the significance of differences in community composition among sample groups.

In other embodiments, the detection of the microbial community members present can be carried out by any number of array hybridization systems, bead multiplex systems, PCR, or any other known detection system. Other embodiments provide a method for selecting and/or utilizing a set of oligonucleotide probes for use in an analysis system or bead multiplex system for simultaneously detecting a plurality of organisms and taxa in a sample and determining a bacteria and/or archaea profile of the sample. Oligonucleotide probes can typically each be from about 5 bp to about 100 bp, preferably from about 10 bp to about 50 bp, more preferably from about 15 bp to about 35 bp, even more preferably from about 20 bp to about 30 bp.

In some embodiments, selected oligonucleotide probes are synthesized by any relevant method known in the art. Some examples of suitable methods include printing with fine-pointed pins onto glass slides, photolithography using pre-made masks, photolithography using dynamic micromirror devices, ink-jet printing, or electrochemistry. In one example, a photolithographic method can be used to directly synthesize the chosen oligonucleotide probes onto a surface. Suitable examples for the surface include glass, plastic, silicon and any other surface available in the art. In certain examples, the oligonucleotide probes can be synthesized on a glass surface at an approximate density from about 1,000 probes per $\mu m^2$ to about 100,000 probes per $\mu m^2$, preferably from about 2000 probes per $\mu m^2$ to about 50,000 probes per $\mu m^2$, more preferably from about 5000 probes per $\mu m^2$ to about 20,000 probes per $\mu m^2$. In one example, the density of the probes is about 10,000 probes per $\mu m^2$. The number of probes on the array can be quite large e.g., at least $10^5$, $10^6$, $10^7$, $10^8$ or $10^9$ probes per array.

Arrays and methods of making and using phylogenetic arrays, resequencing arrays and preparing samples are known in the art and are also described in U.S. Pat. Nos. 7,623,997; 7,668,664; 7,961,323; 7,979,446; U.S. Application Publication No. 20070212718 and 20110039710, and International Patent Pub. WO/2012/027302, all of which are hereby incorporated by reference in their entireties for all purposes, and also described in Wang, Z., Daum, L. T., Vora, G. J., Metzgar, D., Walter, E. A., Canas, L. C., Malanoski, A. P., Lin, B. and Stenger, D. A. (2006) Identifying Influenza Viruses with Resequencing Microarrays. Emerg Infect Dis, 12, 638-646. A complete description of the PhyloChip design and analysis is available in the supplementary methods of Hazen et al., Deep-Sea Oil Plume Enriches Indigenous Oil-Degrading Bacteria. *Science* 2010, 330, (6001), 204-208, hereby incorporated by reference. The PhyloChip (Second Genome, San Bruno, Calif.) was designed to detect most 16S rRNA gene sequences that identify bacteria and archaea. The PhyloChip probes for 59,959 different bacterial and archaeal taxa that represent 147 phyla, 1,123 classes, 1,219 orders and 1,464 families according to the placement of its member organisms in the taxonomic outline as maintained by Philip Hugenholtz. See Hugenholtz, P., Exploring prokaryotic diversity in the genomic era. *Genome Biology* 2002, 3, 1-8. The microarray includes 1,016,064 probe features, the majority of which target 16S rRNA gene sequences that are useful for differentiating taxa. Additional probes are for quality management, processing controls, image orientation, and normalization controls (Hazen, T. C., et al., Deep-Sea Oil Plume Enriches Indigenous Oil-Degrading Bacteria. *Science* 2010, 330, (6001), 204-208).

In another embodiment, microbiome and community metagenomic sequencing is used as is conventionally carried out in the art. See Tal Navvy, Microbial Sequencing at Nature Methods, Methagora Blog Post, *Nature Methods,* 29 Sep. 2014, which cites various reference describing tools, sequencing methods and challenges in metagenomic sequencing including Mavromatis, K. et al, Use of Simulate Data Sets to Evaluate the Fidelity of Metagonimc Processing Methods, *Nature Methods*—4, 495-500 (2007), all of which are hereby incorporated by reference.

In another embodiment, genomic presence and gene expression is detected using quantitative PCR. Primers can be created using the sequences of genes identified as unique regions to identify presence of microbial species and/or expression of any particular gene of interest. As is known in the art, primers or oligonucleotides are generally 15-40 bp in length, and usually flank unique sequence that can be amplified by methods such as polymerase chain reaction (PCR) or reverse transcriptase PCR (RT-PCR, also known as real-time PCR). Methods for qPCR, RT-PCR and its optimization are known in the art. Various chemistries as is known in the art allow detection of PCR products, some via the generation of a fluorescent signal.

In another embodiment, electron microscopy is carried on the sample.

Procedure development and demonstrations: An example of a MCSP procedure application for detecting the dominant species in a biofilm is illustrated in FIG. 3. Referring to FIG. 6, the pre-processed data went through a "loop cycle" computing for each spectrum the $CH_3/CH_2$ ratio, and assigning the membership to the spectrum as archaea if the value of the $CH_3/CH_2$ ratio was within the range of 0.40 and 0.75, and as bacteria if the value was within the range of 0.75 and 2.0. A bar graph (FIG. 3, lower panel) compares the results from our spectroscopy-based MCSP procedure against those from the current widely used genetic-based procedures such as FISH and qPCR analyses.

Figure 4:
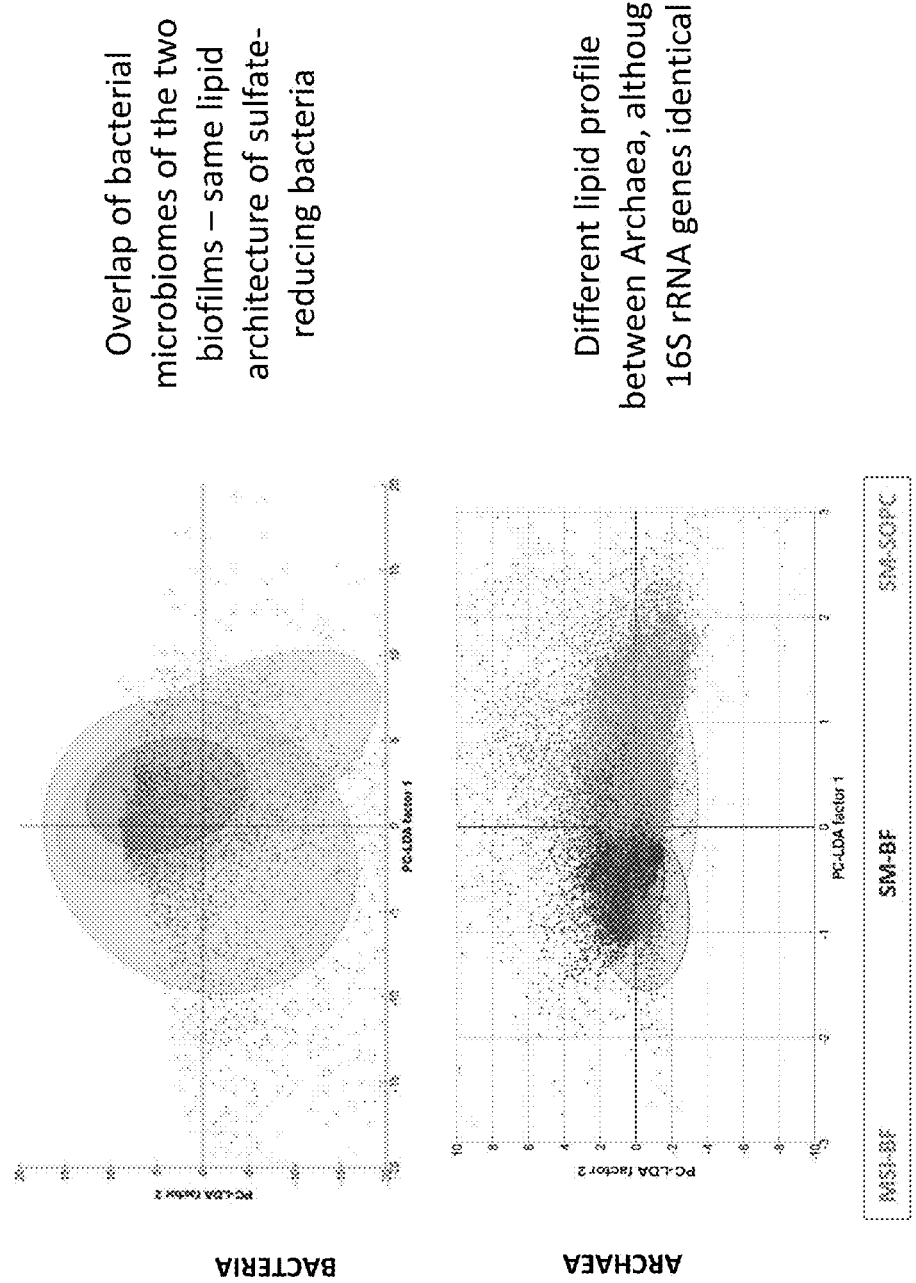
FIG. 4. PC-LDA 2-D plots for archaea (upper panel) and bacteria (lower panel) from the three sampling sites in Germany.

Another example of a MCSP procedure application was for differentiating SM1 Euroarchaeon down to strain levels within a biofilm as illustrated in FIG. 4. Referring to FIG. 6, spectra belonging to the archaeal group (see 00027) were analyzed using PC-LDA in the lipid sROI. The analyses demonstrated great variations in archaeal membrane composition suggesting different SM1 euryarchaeotal strains at both aquifer outlets.

Figure 5:
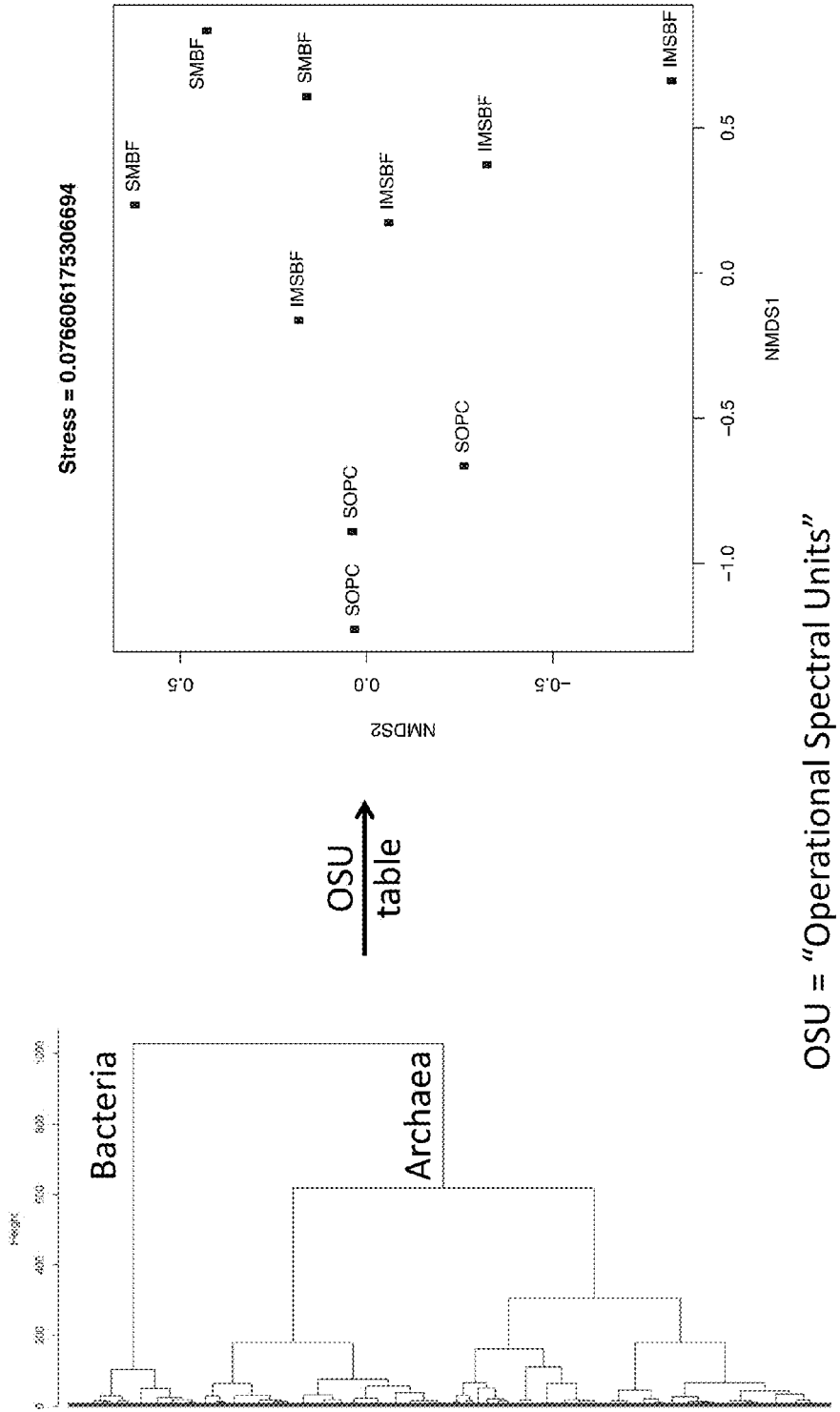
FIG. 5. Nonmetric multidimensional scaling Ordination analysis of all spectra based on hierarchical cluster analysis.

Another example of a MCSP procedure application was for profiling the whole biofilm community as illustrated in FIG. 5. Referring to FIG. 6, 2000 spectra were selected randomly from each of the three data sets from SM-BF. Each spectrum is a vector containing 1608 absorbance data points. These 6000 spectra were grouped into a 6,000×1608 matrix called SM1-BF. The same procedure was repeated for MSI-BF and for SM-SOPC samples. The matrices were merged and analyzed using HCA in the lipid sROI region. Then a correlation matrix containing the cluster "membership" and sample locations was generated. The values within the correlation matrix were called the Operational Spectral Units (OSUs). This matrix was subjected to ordination analyses such as NMDS (Non-metric multidimensional scaling) or PCoA (Principal Coordinate Analysis). Statistical significance of the results will be tested using ADONIS.

Figure 7:
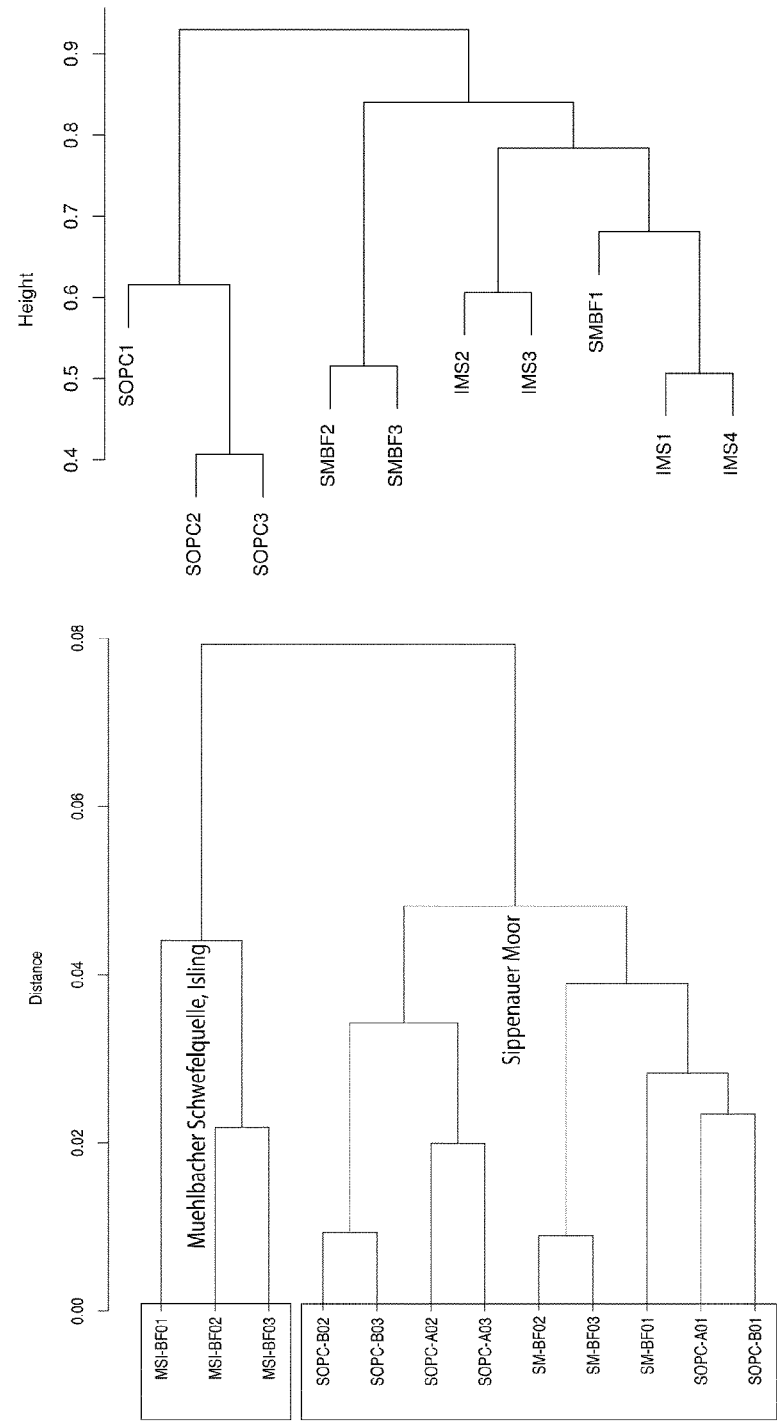
FIG. 7. Beyond 16S rRNA genes: Microbial community profiling using SR-FTIR spectroscopy. PhyloChip G3 versus SR-FTIR spectromicroscopy FIG. 8. Synchrotron radiation based Fourier transform infrared spectromicroscopy: Complementing PhyloChip analysis.
Figure 8:
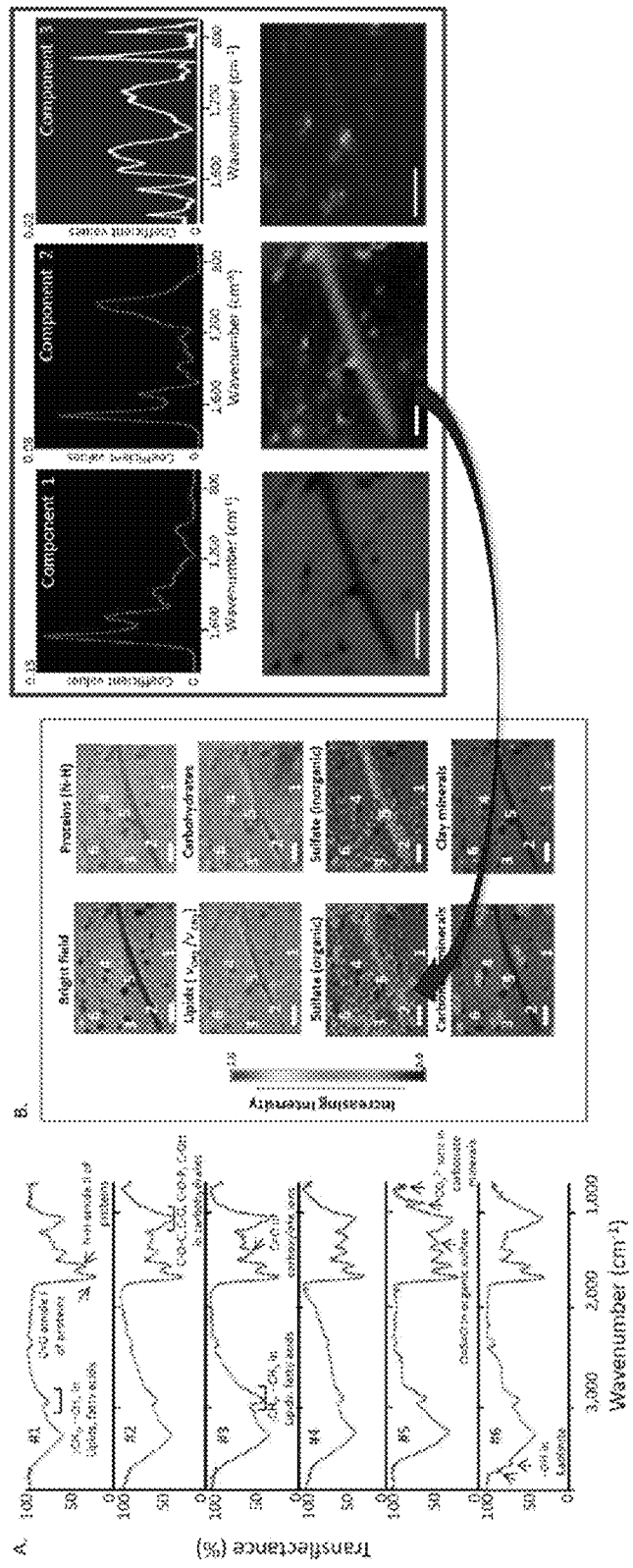

Another example (FIG. 7) compares MCSP procedure application results with those from PhyloChip analysis of how the microbial community structure and relationship change with hydrogeological locations. Referring to FIG. 6, 2000 spectra were selected randomly from each of the three data sets from SM-BF. Each spectrum is a vector containing 1608 absorbance data points. These 6000 spectra were grouped into a 6,000×1608 matrix called SM1-BF. The same procedure was repeated for MSI-BF and for SM-SOPC samples. The matrices were merged and analyzed using HCA in the lipid sROI region. Then a correlation matrix containing the cluster "membership" and sample locations was generated. The values within the correlation matrix were called the Operational Spectral Units (OSUs). This matrix was subjected to HCA based on Euclidean dissimilarity to form a dendogram. The phylochip dendrogram was obtained using HCA based on UniFrac of abundance values of empirical OTUs (operational taxonomic units). Direct comparisons of the two dendrograms suggest that the Phylochip results emphasize geographical effects on microbial community structures, whereas the spectra-based MCSP is sensitive not only to geographical effects but also community chemical and biological composition.

Towards large scale research and industrial applications: Since MCP is non-destructive and allows for label-free multilevel profiling, it can be used to screen biological samples at a chemical level before starting the resource-consuming "omics" analyses. Consequently, this can emerge as one of the primary screening methods in an analytical pipeline for microbial community profiling.

In another embodiment, more sophisticated mathematical and statistical methods such as UniFrac methods for calculating the distance measured between microorganisms within the microbial communities are also incorporated.

Example 1: Sulfate-Reducing Bacteria in an Archaea-Dominated Subsurface Biofilm

Archaea are usually minor components of a microbial community and dominated by a large and diverse bacterial population. In contrast, the SM1 Euryarchaeon dominates a sulfidic aquifer by forming subsurface biofilms that contain a very minor bacterial fraction (5%). These unique biofilms are delivered in high biomass to the spring outflow that provides an outstanding window to the subsurface. Despite previous attempts to understand its natural role, the metabolic capacities of the SM1 Euryarchaeon remain mysterious to date. In this study, we focused on the minor bacterial fraction order to obtain insights into the ecological function of the biofilm. We link phylogenetic diversity information with the spatial distribution of chemical and metabolic compounds by combining three different state-of-the-art methods: PhyloChip G3 DNA microarray technoloay, fluorescence in situ hybridization (FISH) and synchrotron radiation-based Fourier transform infrared (SR-FTIR) spectromicroscopy. The results of PhyloChip and FISH technologies provide evidence for selective enrichment of sulfate-reducing bacteria, which was confirmed by the detection of bacterial dissimilatory sulfite reductase subunit B (dsrB) genes via quantitative PCR and sequence-based analyses. We further established a differentiation of archaeal and bacterial cells by SR-FTIR based on typical lipid and carbohydrate signatures, which demonstrated a co-localization of organic sulfate, carbonated mineral and bacterial signatures in the biofilm. All these results strongly indicate an involvement of the SM1 euryarchaeal biofilm in the global cycles of sulfur and carbon and support the hypothesis that sulfidic springs are important habitats for Earth's energy cycles. Moreover, these investigations of a bacterial minority in an Archaea-dominated environment are a remarkable example of the great power of combining highly sensitive microarrays with label-free infrared imaging.

Introduction. Although the Archaea-scientific community is evolving fast, the lack of knowledge with respect to mesophilic and cold-loving archaea is still enormous. The recent cultivation success of thaumarchaeal representatives is revealing novel and fascinating information, as are alternative procedures that allow in situ studies of archaea in their natural environment or in microcosm experiments (Hatzenpichler et al., 2008; Dekas et al., 2009; Walker et al., 2010; Tourna et al., 2011). One major challenge in understanding the ecological role of archaea is that they are underrepresented in most natural systems, typically accounting for much less than 50% of the microbial cells present. Although some reports have revealed a predominance of (cren-) archaeal cells in marine water columns, reaching numbers of up to 90% Archaea versus Bacteria (Kamer et al., 2001), the archaeal part is composed of a broad diversity in these settings (DeLong, 1998). Natural environments that are predominated by one single species of Archaea are rare; the most famous are the anaerobic methane-oxidizing (AMO) consortium (Orphan et al., 2001) and the 'string-of-pearls community' (Rudolph et al., 2001). Both of these consortia seem to be based on syntrophy, in which both partners are mutually dependent on each other for nutrient exchange (Moissl-Eichinger and Huber, 2011). The AMO consortium has been the subject of numerous analyses and is currently fairly understood but the string-of-pearls community, and in particular the archaeal partner therein (SM1 Euryarchaeon), is still mysterious in many aspects.

The SM1 Euryarchaeon is found in sulfide-containing fresh and marine waters all over Europe (Rudolph et al., 2004), but only two sites (close to Regensburg, Bavaria, Germany) were studied extensively during the past 10 years: The Sippenauer Moor and the Muehlbacher Schwefelquelle ("Winger Muehlbach"; Henneberger et al., 2006). Both of these sites are characterized by a main, sulfidic spring, emanating into a streamlet where whitish mats of sulfide-oxidizing bacteria cover the submerged surfaces. These aquifers are very similar to sulfidic cave springs that are rich in sulfide, ammonia and sulfate (Engel et at, 2004) but poor in dissolved organic carbon, suggesting that the major microbial community of the biotopes are chemolithoautotrophs (Engel et al., 2003; Kodama and Watanabe, 2004). Although, sulfidic springs represent <10% of terrestrial fresh water springs (Palmer, 1991), they are believed to have an important role in global sulfur-cycling (Engel et al., 2003), as they can spawn huge amounts of microbial biomass mainly consisting of sulfur-oxidizing bacteria such as Thiothrix, Beggiatoa and Sulfuricuvum. These filamentous bacteria live as microbial mats or streamers in fluctuating gradients of sulfide and oxygen, and may also be responsible for the environmental success of the SM1 Euryarchaeon under oxygen-rich conditions (Moissl et al., 2002; Rudolph et al., 2004). Surrounding the archaeal colony, Thiothrix (Sippenauer Moor) and *Sulfuricurvum* (Muehlbacher Schwefelquelle) form the string-of-pearls community and possibly interact with the archaeon through an inter-species sulfur cycle (Moissl et al., 2002). In these communities, the bacterial partner and the SM1 Euryarchaeon are present in almost equal abundance, pointing at a 'real' partnership and possibly at a symbiotic/syntrophic relation. The proposed sulfur cycle suggests the SM1 Euryarchaeon being an anaerobic sulfate reducer surrounded by sulfur-oxidizing bacteria. The latter metabolize products from sulfate reduction (H2S), and provide simultaneously the educts (sulfate) for the SM1 Euryarchaeon. In addition, the sulfur-oxidizing bacteria protect the SM1 Euryarchaeon from oxygen exposure by respiration (Moissl et al., 2002).

In contrast to other sulfidic springs that have been microbiologically studied, samples at the Muehlbacher Schwefelquelle can also be taken from ~1 m below the water table, where the upwelling water is not yet mixed with atmospheric oxygen. By placing an in situ trapping system in this subsurface setting, slime-like biofilm structures consisting almost exclusively of SM1 euryarchaeal cells can be caught from the water stream, in stark contrast to the abovementioned string-of-pearls community (Henneberger et al., 2006). This second life-style of the SM1 Euryarchaeon differs also from other described microbial systems, in which archaea are involved in biofilm formation (Lapaglia and Hartzell, 1997; Tyson et al., 2004; Frois et al., 2008): first, the SM1 euryarchaeal biofilm represents the only known naturally occurring Archaea-dominated biafilm, revealing a purity of up to 95% based on microscopic counts (Henneberger et al., 2006). Second, the small archaeal cocci form porous colonies with defined distances between the single cells mediated by their unique cell surface appendages (Moissl et al., 2005; Henneberger et al., 2006). Third, bacteria in the biofilm are either randomly distributed or form dense microcolonies, and their varied morphological appearance hints at a broader genetic diversity, Lastly, no other archaea have been detected within the biofilm, using fluorescence in situ hybridization (FISH) or conventional cloning strategies, suggesting that the SM1 euryarchaeai biofilm is a natural 'archaeal monospecies biofilm' (Henneberger et al., 2006). The Muehlbacher Schwefelquelle spring therefore represents an extraordinary window to an anoxic subsurface biotope of an unusual archaeon.

Using basic biochemical analyses, the water content of the SM1 Euryarchaeon biofilm has been determined to be extraordinary high (99.6%; Amann T et al., unpublished data) and the composition of the extracellular polymeric substance has been shown to have a high ratio of protein versus carbohydrates (1.5:1). No nucleic acids, however, were found in the matrix surrounding the SM1 Euryarchaeon cells (Henneberger et al., 2006). The protein content is mainly owing to its extraordinary cell surface structures, called hami, which are highly-complex, filamentous attachment tools with a nano-sized grappling hook at their end (Moissl et al., 2005).

The biochemical analyses performed to date have been based on protocols that necessitate a complete extraction of chemical compounds from the biofilm and do not allow the assignment of organic and inorganic compounds to the different microbes in the biofilm (for example, to Bacteria or Archaea). Moreover, for the underrepresented bacteria in the biofilm neither their metabolic role nor their (possible metabolic) interaction with the archaea are defined or have been subject to deeper studies besides FISH (Henneberger et al., 2006). Hence, it is uncertain, whether bacterial key species coexist with the SM1 Euryarchaeon, or the detected bacterial diversity is randomly attached to the biofilm.

In order to understand the bacterial (and archaeal) diversity in the biofilm and a possible occurrence of certain key species therein, we have conducted highly sensitive PhyloChip analyses based on the 16S rRNA gene pool of the biofilm. In addition, we used synchrotron radiation-based Fourier transform infrared (SR-FTIR) spectromicroscopy to provide a nucleic-acid independent method to link the phylogenetic diversity information with the spatial distribution of the chemical composition and metabolic activity of the bacterial and archaeal cells within the biofilm. SR-FTIR is a non-invasive and label-free molecular imaging technique capable of micrometer spatial resolution (Holman et al., 2010). In this study, the capability of SR-FTIR to differentiate Bacteria from archaeal cells has been evaluated.

Material and Methods

Sampling Site and Physical Characteristics.

Biofilm samples were collected from the cold (~10.5° C.), sulfidic spring Muehlbacher Schwefelquelle. Its physical characteristics (pH and water composition) have already been described previously (Rudolph et al., 2004; Henneberger et al., 2006), and are found to be very constant over several years of measurement (including sulfate 16 mg 1-1, thiosulfate 14 mg 1-1, ammonia 0.33 mg 1-1). Oxygen concentrations at different locations of the spring and the stream were re-measured using a highly sensitive oxygen dipping probe (PSt6) coupled with temperature measurement (Fibox 3, LCD trace; PreSens, Regensburg, Germany).

Sample Collection.

An in situ biofilm trapping system was used to catch biofilm pieces washed up from the deeper subsurface. The nets were incubated for 3 days as deep as possible in the spring bore. Sampling was performed as described earlier (Henneberger et al., 2006). Samples for FISH analysis were incubated in phosphate-buffered saline-containing paraformaldehyde (final concentration 3% (wt/vol)) for 1 h. at room temperature (22° C.±2° C.); samples for PhyloChip G3 assays were frozen at −20° C. and samples for SR-FTIR spectromicroscopy necessitated air-drying of the biofilm on gold screens (G225G1, Plano GMBH, Wetzlar, Germany). In addition, 25 ml of spring water were collected as a field control for PhyloChip experiments. Anaerobic sampling for incubation experiments was performed as follows: a double-opened Schott flask was placed on a funnel letting almost all water of the spring pass through. The flask had several layers of polyethylene nets to filter the spring water and catch biofilm fragments. After an incubation of 4 days the bottle was closed with rubber stoppers under water (oxygen-free conditions). All samples were kept on ice during the transport from the site to the laboratory.

Metagenomic DNA Extraction.

A measure of 250 µl of each biofilm sample were used for individual extraction procedures. Spring water was concentrated via a Millipore amicon 50 kDa cutoff centrifugal filter (Millipore, Billerica, Mass., USA), according to manufacturer's specifications before undergoing DNA extraction as described previously (Tillett and Neilan, 2000; Moissl-Eichinger, 2011). Concentrations of double-stranded DNA in the samples were determined using Qubit Quantitation Platform (Invitrogen, Carlsbad, Calif., USA).

Quantitative PCR and Cloning of dsrB Genes.

Quantitative PCR (qPCR) was carried out in triplicates with 1 µl of metagenomic DNA as described previously (Moissl-Eichinger, 2011), and the following primer sets were used. Archaeal 16S rRNA genes: 345aF-517uR (Lane, 1991; Burggraf et al., 1992; Moissl-Eichinger, 2011); bacterial 16S rRNA genes: 338bF-517uR (Lane, 1991); dissimilatory sulfite reductase subunit B (dsrB) genes: DSRp2060F (Geets et al., 2006) and DSR4R (Wagner et al., 1998). 16S rRNA gene standards were developed from PCR products of *Methanococcus aeolicus* (DSM 17 508) and *Bacillus safensis* (DSM 19 292), dsrB gene standard was generated from an environmental biofilm sample. After PCR-amplification of dsrB genes with the abovementioned primers the amplicons were cloned into pCR2.1-Togo vector. Fifty-two clones were randomly picked and inserts were sequenced using M13F and M13R primers. Forty-eight clones revealed high quality and were vector-trimmed, clustalW aligned and grouped into operational taxonomic units (OTU) at a 0.01 hard cutoff (Schloss et al., 2009). One representative sequence of each OTU was submitted to GenBank (Acc. no. JX515394-7); a representative clone of the dominant OTU (JX515394) was used for generating a qPCR standard (PCR amplicon generated with M13 primers). The coverage of the library was calculating according to Good (1953), 16S rRNA Gene Amplification.

The template concentration for PCR was set to 3 ng for biofilm samples but DNA isolated from spring water revealed no measurable concentrations (<0.05 ng) due to low biomass. Consequently, 1 ρl of template was used for single PCR; the same settings were also applied for the extraction blank (see below). Bacterial 16S rRNA genes were amplified in a gradient PCR using primers B27f and 1492r as described elsewhere (Hazen et al., 2010), and 30 cycles were run. For amplification of archaeal 16S rRNA genes the degenerated primer pair 345af (5'-CG-GGGYG-CASCAGGCGCGAA-3' (SEQ ID NO: 3) Burggraf et al., 1992)) and 1406ur (5'-ACGGGCGGTGTGTRCAA-3' (SEQ ID NO: 5) (Lane, 1991)) with an annealing temperature of 60° C. were chosen. Running only 25 PCR cycles and an evaluation of the primers via RDP II (Cole et al., 2009) in comparison to previous Archaea-directed primers (Hazen et al., 2010) promised an increase of the detectable archaeal biodiversity (coverage of these and previous primers evaluated via RDP II, FIG. 25). PCR products were gel-purified prior to cloning or microarray analysis (QIAquick Gel Extraction Kit, Qiagen, Germany).

Arehaeal Done Library.

The PCR products of one biofilm sample were used to generate an archaeal 16S rRNA gene clone library by using the TOPO TA cloning kit with TOP 10' cells (In vitrogen), Colonies were manually picked and inserts were amplified using the abovementioned archaeal primer pair. For screening, restriction-fragment-length polymorphisms were performed using two restriction enzymes (HaeIII and HinfI, Promega, Madison, Wis., USA (Vaneechoutte et al., 1992; Moissl-Eichinger, 2011)). Plasmids of clones with unique sequences were purified (Plasmid Mini DNA Purification Kit, Invitrogen) and bi-directionally sequenced using M13 primers (University of California, DNA Sequencing Facility, Berkeley, USA). After chimera check via Bellerophon (version 3 (http://greengenes.lbl.gov/)) and Pintail (Ashelford et al., 2005) sequences were compared with publicly available sequences and among each other using BLAST (http://blast.ncbi.nlm.nih.gov; Altschul et al., 1990).

16S rRNA Gene Microarray (PhyloChip G3) Analysis.

The PhyloChip G3 design, performance and analysis were already described (Hazen et al., 2010). Here, 500 ng of bacterial and 100 ng of archaeal. 16S rRNA gene amplicons were used for PhyloChip analysis of biofilm samples. Hence, only 100 ng of bacterial PCR amplicons and 10 µl of archaeal amplicons (below detection limit) were hybridized on the chip for the background water sample. DNA extraction blanks yielded no quantifiable amounts and 14.5 µl of bacterial and 10.0 µl of archaeal post-PCR were used for PhyloChip assay. After combining amplicons, they were spiked with known amounts of non-16S rRNA genes (total 202 ng), Fluorescence intensities of these positive controls were used to normalize total array intensities among samples. Target fragmentation, biotin labeling, PhyloChip hybridization, scanning and staining, as well as background subtraction, noise calculation, detection and quantification criteria were performed as reported (Hazen et al., 2010).

PhyloChip Data Processing.

Stage 1 and 2 analysis were performed as described elsewhere (Hazen et al., 2010) and thus, the threshold for identifying a bacterial OTU in a sample was set to a minimum of 18 perfect match probes. Quartiles of the ranked r-scores (response score to determine the potential of a probe pair responding to a target and not to the background) had to meet the following criteria: rQ1 0.70, rQ2 0.95, rQ3 0.98. In addition, subfamilies that had an rxQ3 value (cross-hybridization adjusted response score) of 0.48, were considered as present but also requirement for the OTUs within this subfamily to be present.

Figure 15A:
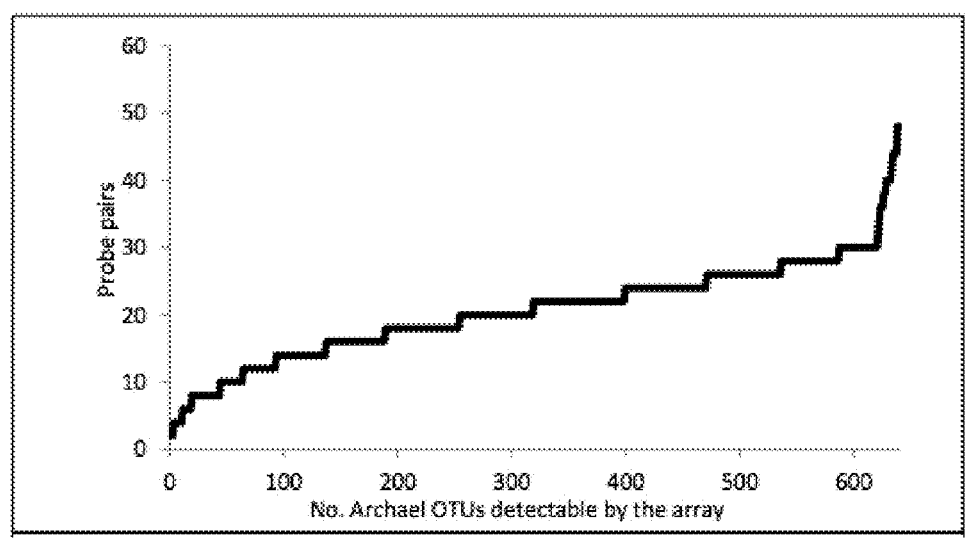
FIG. 15A. Diagram showing the number of archaeal OTUs on the microarray plotted against the number of probe pairs (25-mers) that can be targeted for each OTU by amplicons generated from our archaeal primer set (345aF and 1406uR). As settings demand a probe score of at least 14 pairs to call an OTU present (see Material and Methods) the number of OTUs detectable by the Chip was consequently decreased from 639 to 547.

For analysis of the archaeal OTUs the aforementioned parameters were adjusted to the smaller ~1000 bp 16S rRNA gene amplicons. As shown in FIG. 15A, the number of probe pairs that could possibly be scored with these amplicons, varied among the archaeal OTUs on the chip. Hence, the criterion to call an archaeal OTU present was adjusted to a probe pair score of 14. Consequently, 92/639 of the archaeal OTUs present on the PhyloChip could not be included in the analysis (FIG. 15A); however, these OTUs were not restricted to one specific phylum and spread within the domain of the Archaea.

Subfamily based analysis was done by picking one representative sequence within an OTU per subfamily that was detected at least in ⅔ of the biofilm samples or in the background water. These OTUs were classified to family level using the Greengenes (DeSantis et al., 2006) database in combination with SILVA (Pruesse et al., 2007) and RDP II (Cole et al., 2009). Trees based on multiple sequence alignments were generated by retrieving 70 000 character alignments from SILVA database and the neighbor joining method (MEGA 4, (Tamura et al., 2007)). Trees with heatmaps were rendered in iTOL (Letunic and Bork, 2007).

Identification of Significantly Enriched OTUs in the Biofilm.

Figure 15B:
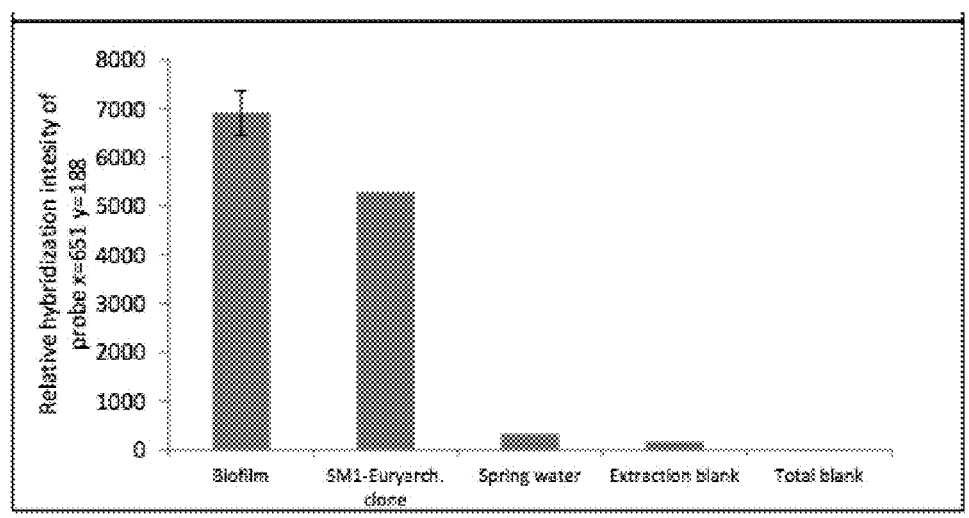
(FIG. 15B) Response of the SM1-Euryarchaeon specific probe (x=651, y=188, oligonucleotide sequences ©2011 Second Genome, Inc.) to different samples. Biofilm represents an average of the three biofilm samples, error-bar gives minimal and maximal values of replicates, SM1-Euryarchaeon clone is an array run with 50 ng of the 'dominant' SM1-Euryarchaeon clone IM-A1 (JN861739), Spring water is a water sample of the sampling site, Extraction blank is the DNA extraction control and Total blank is a total array blank. For more details see Material and Methods section.

As the full 16S rRNA sequence of the SM1 Euryarchaeon is still not publicly available (Rudolph et al., 2001), this Euryarchaeon had not been included in the PhyloChip G3 design (Hazen et al., 2010). In order to track the abundance of the SM1 Euryarchaeon in samples analyzed with PhyloChip G3, the 1019 bp-long sequence of the dominant SM1 Euryarchaeon clone (IM-A1, JN861739) was bioinformatically broken up into 995 25-mers and compared with all probes present on the PhyloChip. Nine different probes were identified to perfectly match with the A1 clone sequence but only one of them revealed high specificity. By using RDP II probe match (Cole et al., 2009) the probe 5'-TGTG-CAAGGAGCGGGGACATATTCA-3' (SEQ ID NO: 6) on the microarray (x=651, y=188; oligonucleotide sequences © 2011 Second Genome Inc) was identified to match with only seven different archaeal sequences in the database, three of them belonging to SM1 euryarchaeal sequences. The relative hybridization intensities of this probe for biofilm, and water samples as well as positive and negative controls are given in FIG. 15B. As a matter of fact, the biofilm showed higher relative hybridization intensities (100 ng of archaeal PCR product) than the positive control (50 ng of purified PCR product of clone A1), reflecting the high abundance of the SM1 Euryarchaeon in the biofilm. The negative control and the extraction blank (see below) revealed very low intensities. Furthermore, the background water sample from the spring showed a very weak, relative hybridization intensity of 324 compared with an average value of 6913 retrieved from biofilm samples indicating a latent presence of the SM1 Euryarchaeon in the spring water (FIG. 15B).

Molecular Analysis Controls.

Controls were included in each step mentioned above. For DNA extraction, a negative control performed with PCR grade water was used. The same control was then included in archaeal and bacterial 16S rRNA gene amplification and in PhyloChip analysis. Probes with positive response were masked in PhyloChip analysis of the actual samples in order to avoid false positives. In addition, a negative control of the PhyloChip analysis was performed that included nuclease- and nucleic-acid-free water as well as the spike genes only. However, no OTUs met the threshold requirement neither in the extraction blank nor in the negative control. As a positive control, 50 ng of SM1-Euryarcheon clone IM-A1 (JN861739) was run in microarray analysis in order to see probe responses to the SM1-Euryarchaeon amplicon in comparison to environmental samples, which detected also no other OTUs.

FISH and Fluorescence Microscopy.

Whole-cell hybridizations were performed as mentioned elsewhere (Rudolph et al., 2001), using domain- and species-directed probes (Bacteria: EUB338 (Amann et al., 19901)), Archaea: ARCHmix (Moissl. et al., 2002; Henneberger et al., 2006), SM1 Euryarchaeon: SMARCH714 (Moissl et al., 2003). For the detection of bacteria involved in sulfate reduction, the sulfate-reducing bacteria (SRB) 385 probe (Amann et al., 1990a) and the Delta495a/b/c probe mix was applied (Loy et al., 2002). Probes were labeled with Rhodamine Green (RG), Cy3 and Texas Red. Specimens were afterwards analyzed using either confocal laser scanning microscopy (CLSM, LSM 510 Meta, Zeiss, Oberkochen, Germany; exc, 488 and 543/em. LP 505 and LP 585; multi-track for RG and Cy3) or epifluorescence microscopy (Olympus BX-60, Hamburg, Germany). For controls, a fluorescent dye-labeled nonsense probe (NONEUB338) were applied to the samples, and separate bacterial controls were also included (*Bacillus atrophaeus* DSM7264, *Escherichia coli* K12 DSM30083). Theoretical coverage of FISH probes and representative sequences of PhyloChip OTUs (in silica FISH) was assessed using the ARB software package (Ludwig et al., 2004).

CTC-FISH to Measure Activity of Specific Microorganisms.

Biofilm samples were sampled anaerobically as described above and handled in an anaerobic glove box (Coy, Grass Lake, Mich., USA), Biofilms were supplemented with 100 μl spring water and 10 μl 50 mM CTC (5-cyano-2,3-ditoryl tetrazolium chloride; Stellmach, 1984; Stellmach and Severin, 1986; Yoshida and Hiraishi, 2004), which was prepared under anaerobic conditions (N2 gas phase). After an anaerobic incubation of 2 h at 11° C. in a waterbath, the biofilms were removed and underwent fixation, FISH in suspension (Delta495a/b/c mix, RG, performed similar to Walther et al., 1993) and subsequent DAPI (4',6-diamidino-2-phenylindole) staining.

SR-FTIR Spectromicroscopy Imaging and Data Analysis.

SR-FTIR spectromicroscopy is a non-invasive and label-free chemical imaging technology that provides molecular information at micrometer spatial resolution (Carr et al., 1995; Dumas et at, 2009). SR-FTIR takes advantage of three technologies: (i) the well-known sensitivity of infrared spectroscopy to the bond vibration frequencies in a molecule for determining molecular functional groups, (ii) the convenience of a light microscope to locate areas for molecular and composition analysis, and (iii) the 100- to 1000-fold increase in signal-to-noise provided by a bright SR-based infrared light source. Using photons in the mid-infrared region (~2.5 to ~15.5 μm wavelength, or ~4000 to ~650 wavenumber in cm−1), SR-FTIR spectromicroscopy has been successfully used to characterize microbial activities in geological materials and in both hydrated and dried biofilms (Holman et al., 2009; Hazen et at, 2010; Holman et al., 2010), in spite of the limitation that some signals may be ambiguous.

Freshly harvested samples (four replicates) were gently air dried onto gold-coated copper disks. Although drying affects the three-dimensional structure of the biofilms, prior microscopy experiments with other biofilms suggest that the two-dimensional structure is largely unaffected. Therefore, the measured spatial distribution of Bacteria, Archaea and the biogeochemical features could represent their native two-dimensional distribution within the biofilm. All SR-FTIR spectromicroscopy measurements were performed in the transflectance mode at the infrared beamline of the Advanced Light Source (http://infrared.als.lbl.gov/), where mid-infrared photons emitted from the synchrotron are focused with a 0.65 numerical aperture objective in a Nicolet Nic-Plan infrared microscope. In transflectance mode, the beam is transmitted through the sample, reflected off the gold-coated copper surface and then transmitted through the sample a second time before striking the mercury cadmium telluride detector. Each spectrum is an average of eight scans at a spectral resolution of 4 cm−1. Background spectra were obtained on the cell-free area of the discs.

For each SR-FTIR imaging measurement, the 200 μm×150 μm field-of-view for the biofilm was divided into equal-sized 2 μm×2 μm pixels before raster scanning. The resulting data cube, which consists of position-associated FTIR spectra, was subjected to data preprocessing and processing calculations, including spectrum baseline removal, using both Thermo Scientific Omnic version 7.3 (Thermo Scientific, Madison, Wis., USA) and Matlab (MathWorks, Nattick, Mass., USA). The absorption spectra were then subjected to univariate and unsupervised multiple curve resolution (MCR) image analyses. The univariate approach, which integrates infrared absorbance of an individual peak of interest, relates the absorbance intensity to the relative concentration of a particular chemical component through the Beer-Lambert law. The unsupervised MCR approach, on the other hand, is based on the principal component analysis (PCA) of the entire fingerprint region (1800-700 cm−1) and of the C—H region (3100-2800 cm−1) instead of individual peaks. MCR analysis of SR-FTIR spectra was applied to reveal the distributions of Archaea, Bacteria and chemical variations in the biofilms, which were hidden in the univariate approach. In this study, the unsupervised MCR analysis was performed with non-negative constraints on both concentration and spectral values (Budevska et al., 2003).

Validation of SR-FTIR for Differentiating Archaea and Bacteria in Biofilms.

Our SR-FTIR approach assumed that Bacteria can be distinguished from Archaea by comparing spectral features of their lipids in the C—H region due to differences in cell envelope compositions. To confirm this, we performed validation experiments using the following four strains of archaea and bacteria: the archaeon *Sulfolobus solfataiicus* DSMZ 1616T (grown at 80° C. in 0.25×SME medium) with glycosylated surface layer protein on its surface, the archaeon *Methanopyrus kandleri* DSMZ 6324T (98° C., in SME medium) with a pseudopeptidoglycan-containing cell wall covered by a proteinaceous layer, the Gram-negative bacterium *E. coli* K12 DSMZ 30 083T (37° C., in LB medium) with a comparably less amount of peptidoglycan but large amount of lipopolysaccharides in its cell envelope, and the Gram-positive bacterium *B. atrophaeus* DSMZ 7264T (32° C., in TSB (tryptic soy broth) medium) with a high amount of peptidoglycan in its cell wall. We first made SR-FTIR measurements on the four archaea and bacteria strains, and results were compared and summarized in FIG. 1.

Baseline corrected and vector-normalized spectra in the C—H region between 3000 and 2800 cm−1 were then subjected to the multivariate PCA and then linear discriminant analysis (LDA) using MathLab (7.0). PCA and LDA were used to generate new variables (factors) that were linear combinations (that is, weighted sum) of the original variables (wavenumbers). PCA was first applied to the spectra to reduce the hundreds of absorbance intensities at different wavenumbers to just a few factors that could capture more than 95% of the variance. We typically selected seven components based on the 95% percentage of variance explained and on the spectral features of the loading plot, LDA was then applied to maximize the 'inter-class' variance over the 'intra-class' variance of the factors. We visualized the multivariate analysis results in the form of score plots (FIG. 2A) and cluster vector plots (FIG. 2B), In this study, score plots were three-dimensional plots where the first three PC-LDA components were the x-, y- and z-axes; the nearness between classes (clusters) indicates the similarity, whereas the distance between classes implies dissimilarity.

Figure 16A:
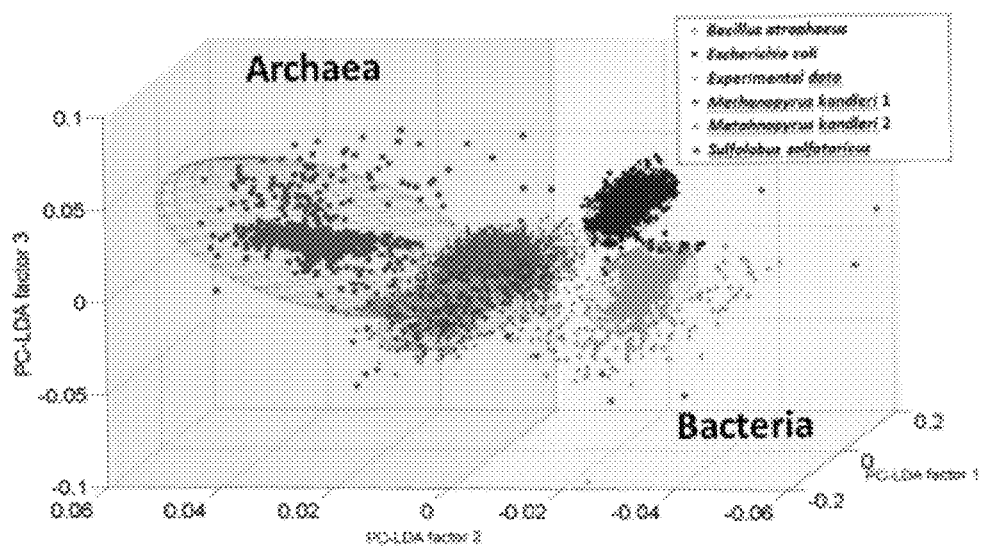
FIG. 16A-D. SR-FTIR Validation experiments. A comparison of field biofilms (experimental) with the reference samples (see FIGS. 2A and 2B).
Figure 16B:
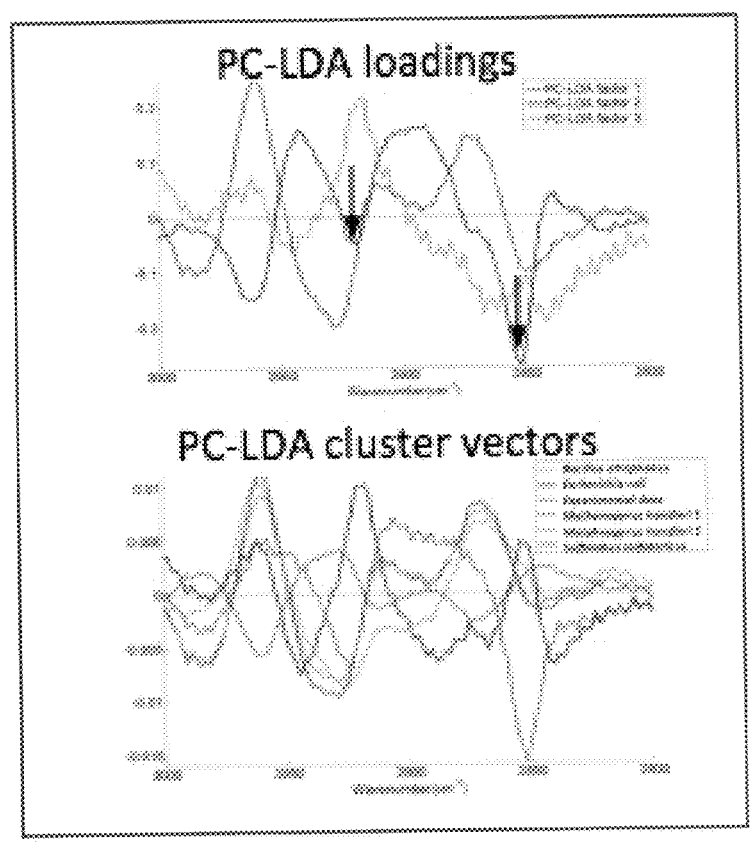
Figure 16C:
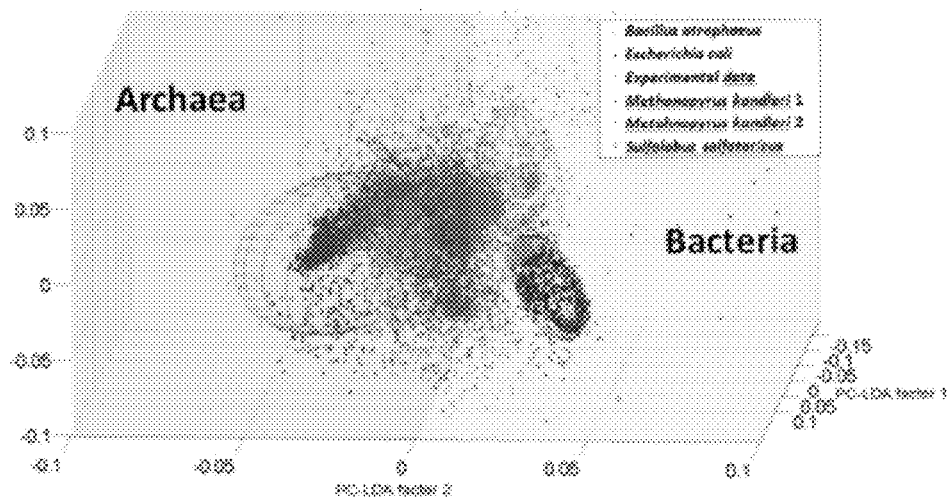
Figure 16D:
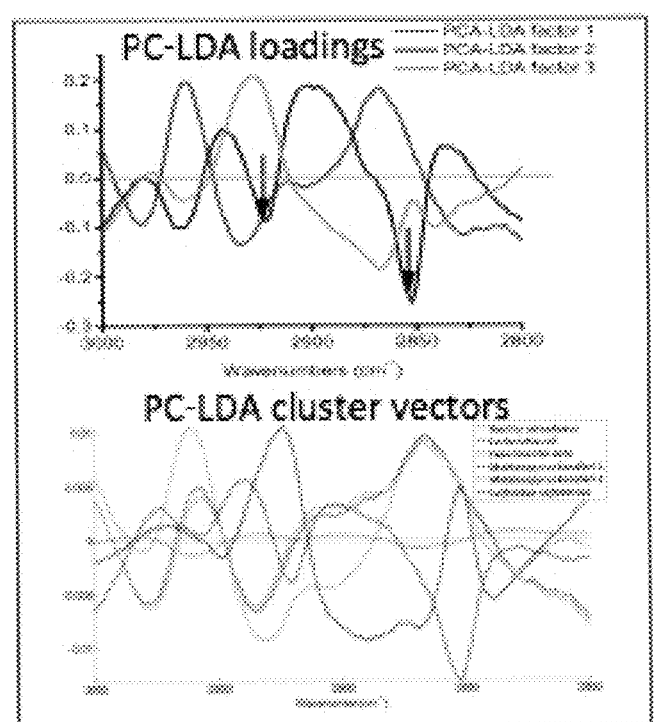

Detailed analyses (FIGS. 2A and 2B) revealed that, in spite of the significant variations in the cell envelope (including cell wall) compositions. Bacteria can be distinguished from Archaea solely by comparing spectral features of their lipids in the C—H regions (3100-2800 cm$^{-1}$). As expected, bacterial membrane lipids consist of fatty acids with long alkylic (—CH2-) chains which have only one to two terminal methyl (CH3-) groups. In contrast, archaeal membrane lipids generally consist of branched and saturated hydrocarbon isoprene, and therefore relatively less CH2- and more CH3- groups (Mancuso et al., 1986). Our earlier study showed that the SM1 Euryarchaeon possesses a typical CH3-rich lipid (archaeol, Rudolph, 2003). In this context, the ratio of CH2 to CH3 could be used to detect Bacteria in an Archaea-dominated biofilm (FIGS. 16A and 16B).

Figure 17A:
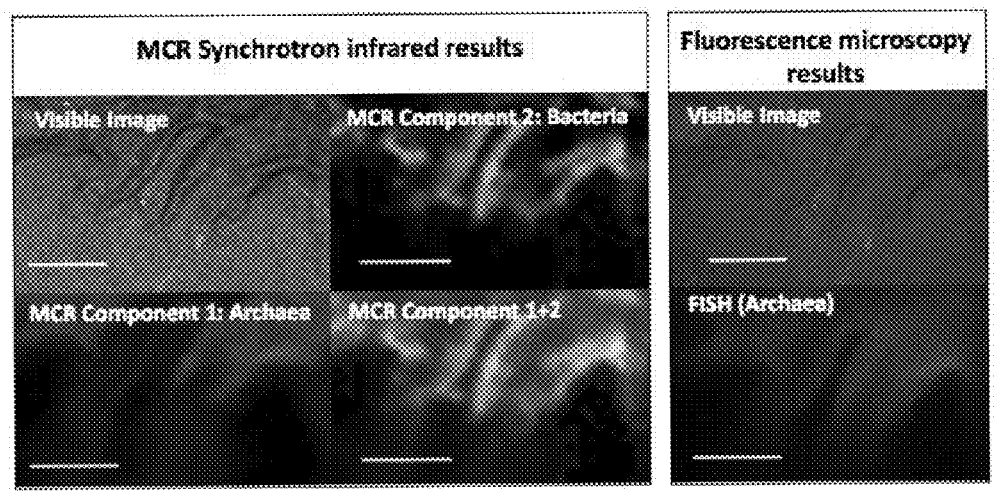
FIGS. 17A and B. SR-FTIR Validation experiments: Correlation and colocalization analysis of images.
Figure 17B:
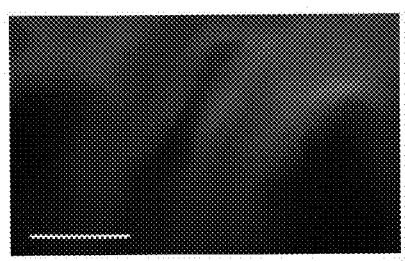
In FIG. 17B, the red (Archaea recovered from MCR component 1) and green (Archaea FISH stained image) images of the same biofilm but different effective spatial resolution (microns for infrared and hundreds of nanometers for fluorescence microscopy). Nevertheless, its Pearson's coefficient, which was strongly influenced by the ratio of the light intensity at each pixel, was 0.504; Manders' overlap coefficient, which was sensitive to the absolute light intensity, was 0.798. The colocalization coefficients M1 (=0.988) and M2 (=1.000), which were normalized against total "pixel" intensity, had a value of 0.988 and 1.00 respectively (Manders et al., 1993).

To confirm this observation further, we made measurements and performed spatial correlation analysis on FISH and MCR SR-FTIR images (FIGS. 17A and 17B) using the image processing software ImageJ) http://www.macbiophotonics.ca/imagej/) and Manders approach of interpretation (Manders et al., 1993). Field-collected biofilm samples were labeled with Archaea-directed probes (ARCHmix; Moissl et al., 2002; Henneberger et al., 2006). The samples fluorescence and the corresponding MCR SR-FTIR images were acquired by means of a Nicolet Continuum XL infrared microscope equipped with a fluorescence attachment and a WG fluorescence cube. Although the MCR recovered image and the fluorescence image have different 'brightness', 'intensity' and effective spatial resolution (microns for infrared and hundreds of nanometers for fluorescence microscopy), Pearson's coefficient was 0.504, Manders' overlap coefficient 0.798, the co-localization coefficient M1 was 0.988 and M2 was 1.000 (Manders et al., 1993). This demonstrated that the two images were quite similar (Manders et al., 1993).

Results

Using an in situ trapping system (Henneberger et al., 2006), fragments of the SM1-Euryarchaeon biofilm from the subsurface were collected for an in-depth characterization of the unique subsurface biotope that can be accessed through the Muelabacher Schwefelquelle.

Oxygen Concentration in the Spring Area Revisited.

Figure 18:
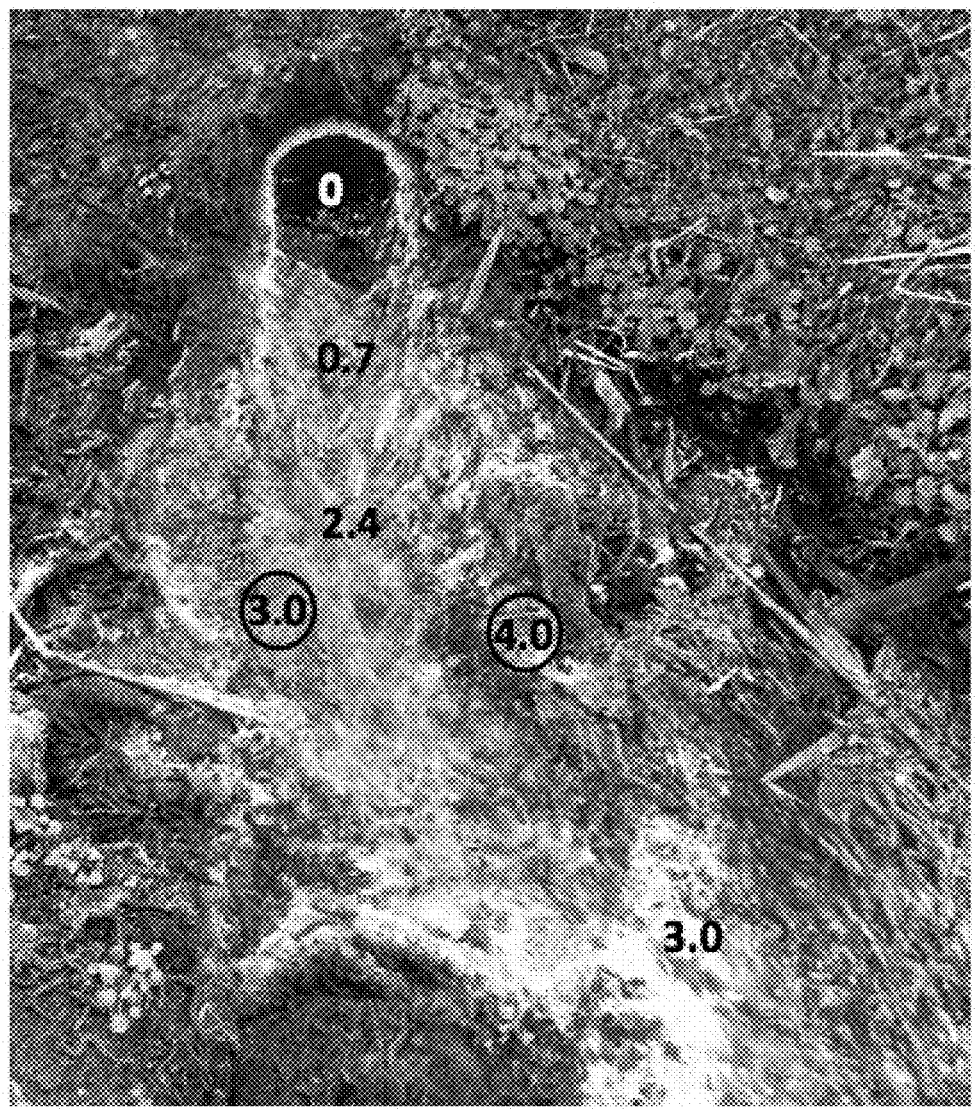
FIG. 18. Oxygen concentrations (µmol/l) at certain locations of the Muehlbacher Schwefelquelle. The subsurface water was determined oxygen-free at a depth of 6 cm from the surface or below. Oxygen concentrations in circles are usual sites for sampling the string-of-pearls community of SM1 Euryarchaeon and *Sulfuricurvum* (IMB1-Epsilonproteobacterium, Rudolph et al., 2004). The temperature was constant at 10.5° C. at all locations.

Using a highly sensitive oxygen probe, a chemocline could be detected with decreasing oxygen concentrations towards the spring (FIG. 18). No oxygen could be measured in the subsurface water before mixing with the atmosphere in the streamlet, indicating a complete oxygen-free environment in the subsurface. These on-site measurements are in contrast to previous investigations that reported low amounts of oxygen in the spring water (Rudolph et al., 2004; Henneberger et al., 2006).

Dominance of the SM1 Euryarchaeon in the Subsurface Biofilm.

FISH with Archaea-directed and SM1 Euryarchaeon-specific probes confirmed previous results showing the archaeal dominance within the biofilm. The predominance of the SM1 Euryarchaeon was additionally confirmed by using domain-specific qPCR. The ratio of archaeal and bacterial 1.6S rRNA gene copy numbers was 97:3 (FIG. 9), which is similar to previously reported ratio of Archaea: Bacteria being 95:5 (Henneberger et al., 2006). A newly constructed clone library of archaeal 16S rRNA gene sequences generated from biofilm samples resulted in four different restriction-fragment-length polymorphism patterns after analyzing 48 clones. The dominant clone sequence (88% of all clones, IM-A1, JN861739) and two others (2%, IM-C8, JN861741; 2% IM-4-1, JN861742) showed high similarity to publicly available 16S rRNA gene sequences of the SM1 Euryarchaeon and among each other (>99%), One clone sequence (8%, 1M-C4, JN861740) was closely related to the environmental clone sequence SMK5 (Rudolph et al., 2004), which was retrieved from Sippenauer Moor string-of-pearls community in 2005 (99% similarity) but shows a genetic distance of 20% to the SM1 Euryarchaeon sequence.

The currently most sensitive method available (PhyloChip G3 16S rRNA gene microarray technology, detection limit 2 µM of 165 rRNA PCR product; (Hazen et al., 2010)) was used for characterizing the archaeal and bacterial composition in the biofilm and the spring water itself based on 16S rRNA gene analysis. Besides a comprehensive detection of Bacteria, the setup of the PhyloChip (33 technology was geared towards the identification of (also underrepresented) archaeal signatures. To avoid primer mismatches of typical, Archaea-directed primers binding to the front region of the 16S rRNA gene (Rudolph et al., 2001), a different primer set for amplification of (SM1 eury-) archaeal 16S rRNA genes was used and an adjusted bioinformatical approach for the shorter PCR amplicons was necessary. Although the SM1 Euryarchaeon was originally not included in PhyloChip (33 design (Hazen et al., 2010), we developed a method to track its abundance in our samples based on the hybridization intensity of a specific probe on the microarray. With the aid of PhyloChip technology, the SM1 Euryarchaeon was detected highly enriched in the biofilm samples (~2130% increase in abundance) compared with the spring water.

Microbial Diversity in Spring Water and Biofilm.

Figure 10:
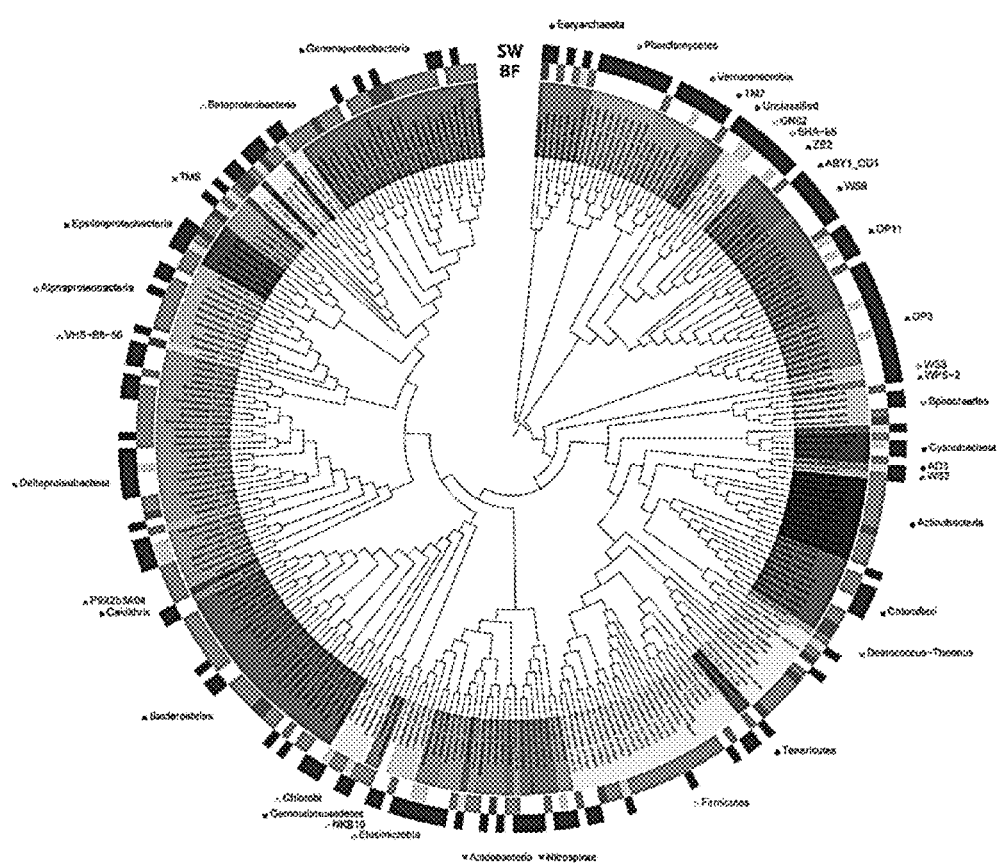
FIG. 10. Difference in microbial richness between the spring water and the biofilm: presence and absence of subfamilies in spring water (SW) and biofilm samples (BF), Color intensities (red) of the biofilm samples reflect the number of times the subfamily was called present in one of the three replicates. As the SW sample was not replicated, heatmap reflects presence (blue label) or absence only. The Neighbor Joining tree was constructed with one representative OTU per subfamily (branch length is ignored), Leaf IDs give the classification on family level and the accession number of the representative OTU. Only those subfamilies that occurred in the water sample or in at least ⅔ of the biofilm replicates are shown.

In the spring water and biofilm microbiome, in total 4444 OTUs in 869 different subfamilies were detected by PhyloChip analyses with 10 OTUs (in 10 subfamilies) belonging to the archaeal domain in addition to the SM1 Euryarchaeon. The overall distribution of the microbial taxa on subfamily level ranged from 14% for Firmicutes to 0.1%, for example, for Aquificales. Only 36% of the subfamilies detected in the water were also present in at least one of the three biofilm replicates (FIG. 10).

Figure 19B:
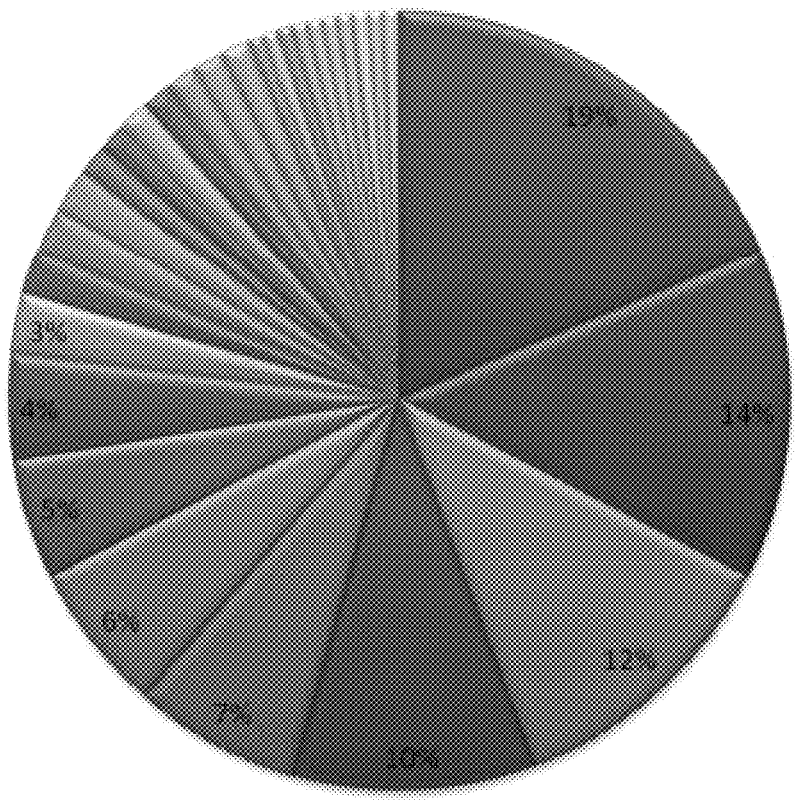
FIG. 19B shows the distribution of subfamilies in higher taxa detected by PhyloChip G3 in biofilm samples. Only those subfamilies were considered if called present in at least ⅔ of the samples.

The diversity of the spring water was dominated by Deltaproteobacteria (14%); however, signatures of Methanomicrobia and Thermoplasmata of the archaeal domain were also retrieved (distribution of spring water diversity in FIG. 19A). The diversity of Firmicutes, Gammaproteobacteria and Bacteroidetes increased in the biofilm, whereas members of the OP11-group and the Planctomycetes were less diverse than in the spring water. Considering the diversity of subfamilies that occurred in at least ⅔ of the biofilm samples, Firmicutes were again the most diverse taxon, followed by Gammaproteobacteria and Bacteroidetes (FIG. 19B).

Core Microbiome of the Biofilm.

Figure 20A:
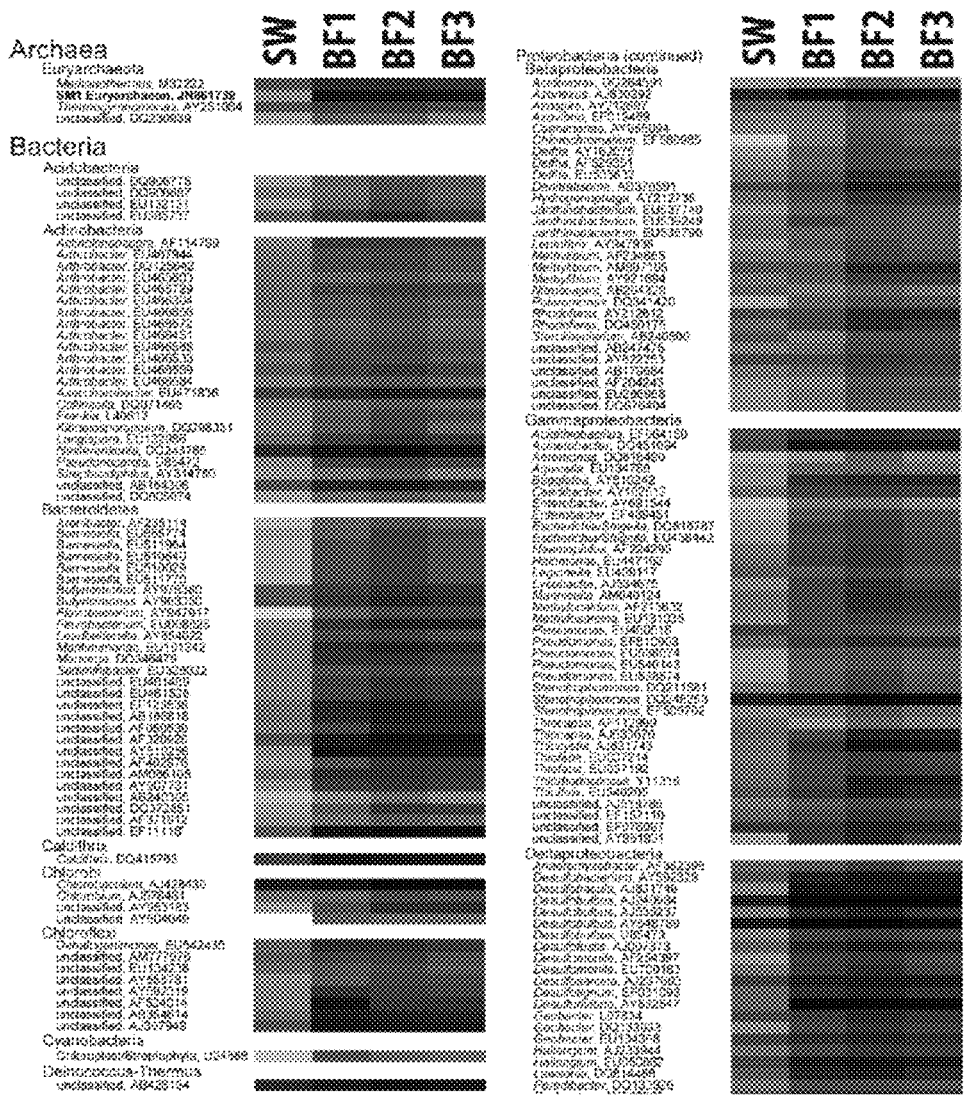
FIGS. 20A and 20B. Core microbiome of the SM1 Euryarchaeon biofilm. Heatmap displaying all OTUs that occurred in at least ⅔ of the biofilm samples and that had a coefficient of variation less than 10% among replicates. OTUs were classified on genus level and their phyla are given in alphabetical order. The heatmap shows abundance values of each OTU per sample (SW spring water and BF1/2/3 biofilm replicate 1/2/3). Spearman correlation of abundances OTUs was [0.87:0.97] among biofilm replicates and only [0.63:0.64] for biofilm samples in comparison with the spring water sample. This showed that there is a high correlation among biofilm replicates concerning decline and increase of single OTUs but less correlation between spring water and biofilm microbiome was observed, which reflect the microbial shift detected in subfamily analysis (see Result section). More than 10% of the core microbiome was previously reported from sulfur, aquatic or biofilm related habitats. Many of the detected genetic signatures belonged to bacteria possibly involved in sulfur metabolism (22%), such as Thiotrichales, Helico-bacteraceae, Desulfovibrionales, and Desulfobacterales. However, a large diversity of potentially sulfate-reducing bacteria (SRB) could be identified among these (33%).
Figure 20B:
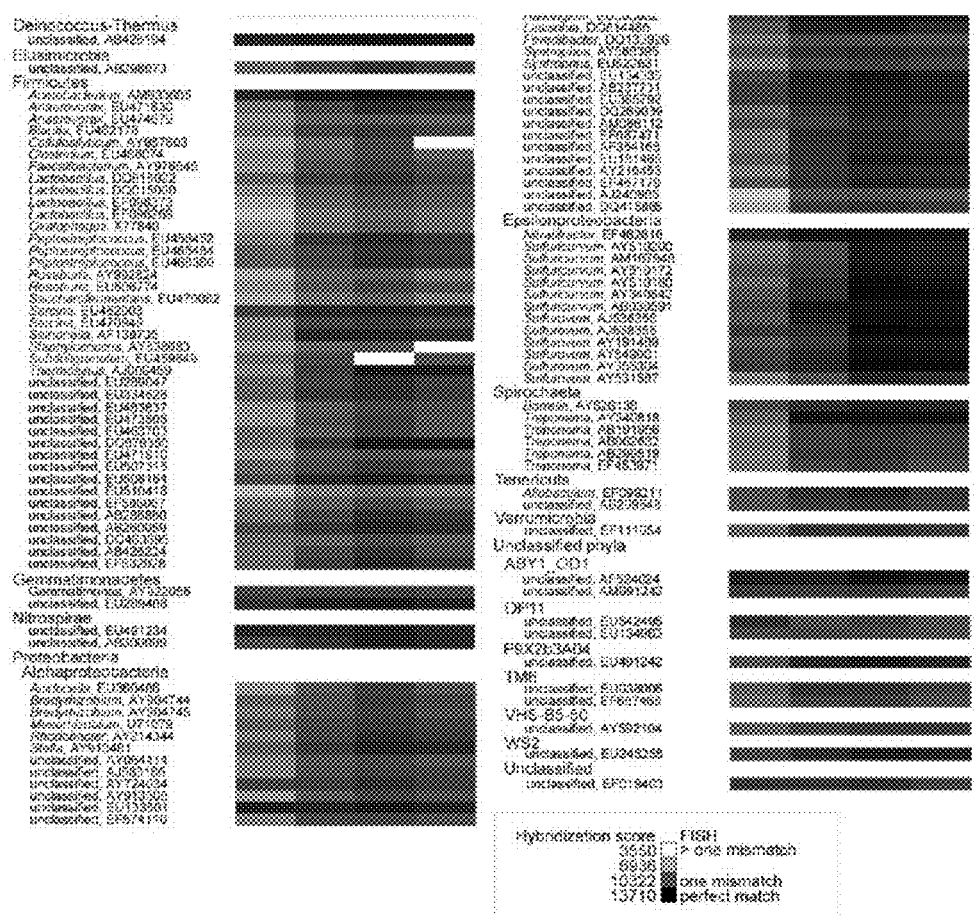
Figure 21A:
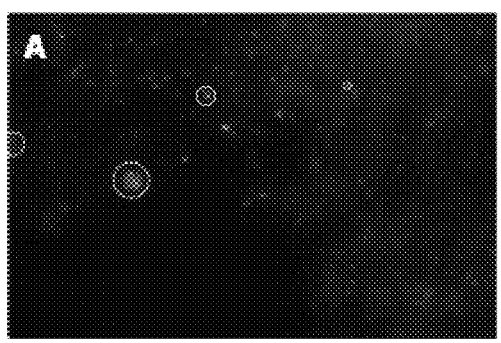
FIG. 21A-D. Combination of CTC-staining, FISH in suspension (Delta495 probe mix RG-labeled, please see Material and Methods for details on the probes), and DAPI to detect metabolic activity of sulfate-reducing bacteria in biofilm samples.
Figure 21C:
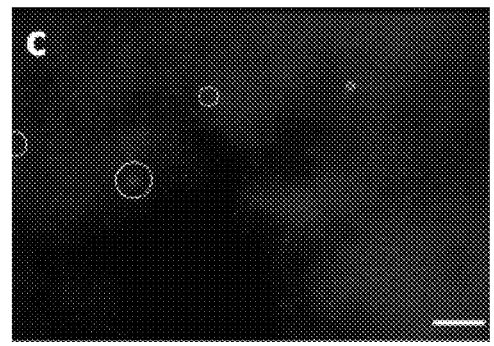
Figure 21B:
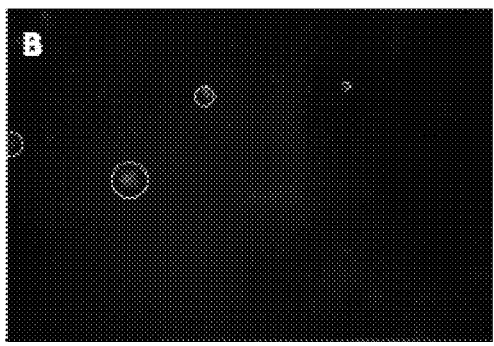
Figure 21D:
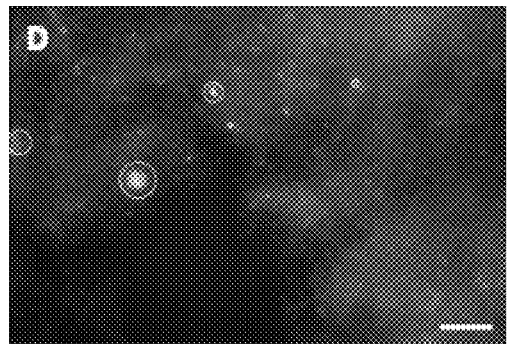
Figure 22A:
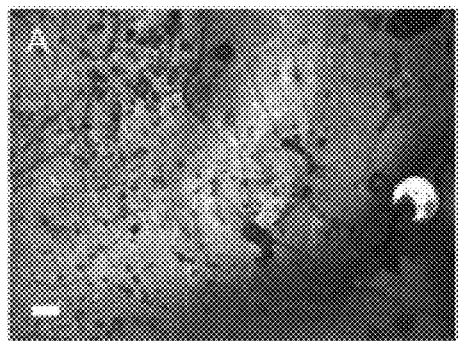
FIG. 22A-D. Typical visible light microscope images of the biofilms in this study.
Figure 22B:
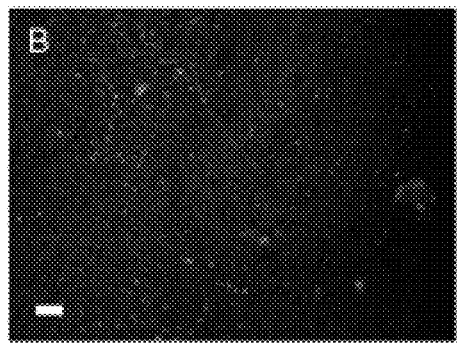
Figure 22C:
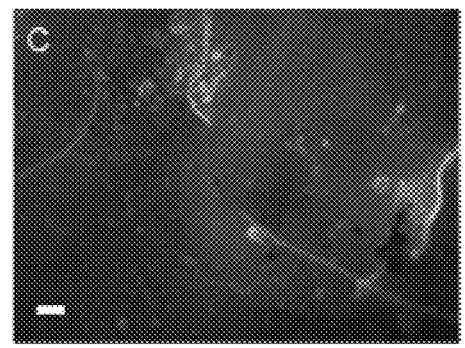
Figure 22D:

Biofilm subfamilies detectable in ⅔ replicates were then analyzed in depth at the OTU level. If the coefficient of variation of the abundance values of a single OTU was <10% among biofilm replicates, the OTU was assumed to be non-fluctuating, and thus a constant member (potential key species) of the biofilm. Abundance values and a detailed description of these constant OTUs (263, including the SM1 Euryarchaeon) are presented in FIGS. 20A and 20B. This community is considered to represent the core microbiome of the biofilm.

As OTUs such as Thiothrix clone sipK4 (AJ307941) and the *Sulfuricurvum* clone IMB1 (AJ307940) were found to fluctuate, they were not considered as representatives of the core microbiome. However, both of these OTUs have been identified as key species in the string-of-pearls communities at various sampling sites (Rudolph et al., 2001; Moissl et al., 2002). Eleven other string-of-pearls community related OTUs, which had been reported but not as key species, were also identified and found to be mostly fluctuating (FIG. 19).

Significantly enriched OTUs in the biofilm compared with the string-of-pearls community.

PhyloChip G3 analyses revealed 2139 OTUs that increased in abundance in the biofilm samples compared with the reference sample set (string-of-pearls community, data not shown). Eighty-three OTUs met the requirement of being highly significantly enriched (adjusted P-value 0.002), which were grouped into 44 subfamilies and are displayed in FIG. 4. The OTU with the greatest increase in abundance (accession number of representative sequence AJ831749; increase in abundance: 4559) was also the OTU with the most significant P-value of 4.60E-06. The representative sequence grouped this OTU in the Deltaproteobacteria, genus *Desulfobacula*. However, also OTUs of other phyla and genera were detected as significantly enriched, among those many Chloroflexi and Spirochetes.

Detection of SRB Via FISH and Correlation with PhyloChip Data.

The presence and amount of (potentially) SRB in the biofilm was further confirmed by FISH with two different (sets of) probes targeting bacterial sulfate reducers: bacterial sulfate-reducer probe SRB385 and Delta495 probe mix. Each approach was backed up by probes directed for Bacteria (Eub 338/I, Texas Red) or Archaea (ArchMix, RG), and DAPI staining or combinations thereof. The specificity of FISH experiments was confirmed by using appropriate controls and a nonsense probe (NONEUB338), which showed no signal when applied to biofilm samples.

Figure 12A:
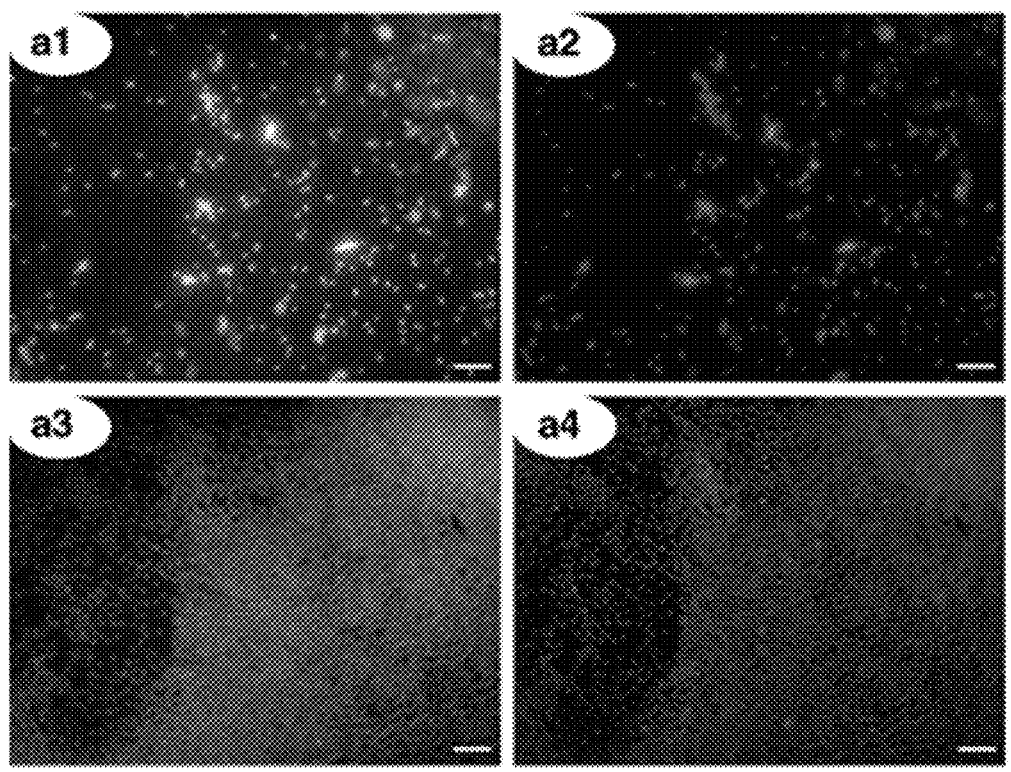
FIG. 12A shows ternary FISH analysis of the subsurface biofilm with SRB-, Bacteria and Archaea-specific probes. Analysis reveals dominance of archaeal cocci (SM1 Euryarchaeon) and of SRB-385-stained bacteria in the bacterial minority: ~85% of the detected Bacteria revealed a signal with the sulfate-reducer specific probe. Scale bars=10 μm. a1: biofilm, FISH-stained with probe SRB385 CY3 (targeting SRB, yellow). a2: same detail, stained with probe EUB 338/I Texas Red (targeting Bacteria, red), a3: same detail, stained with probe mixture ArchMix RG (targeting Archaea, green). a4: same detail, reference-stained with DAPI (blue).
Figure 12B:
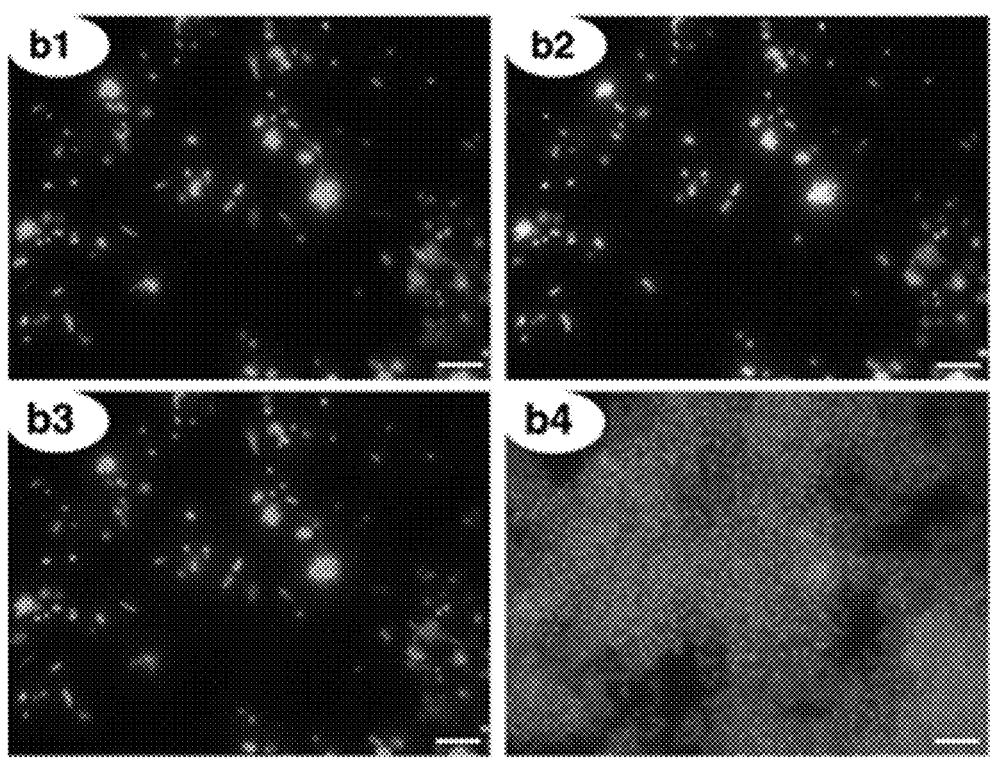
FIG. 12B biofilm sample FISH-stained with SRB-directed Delta495 probe mix. The overwhelming majority of bacteria in the biofilm showed signals with the Delta495 probe mix (89.2%). Scale bars=10 μm. b1: probe 338/I RG (targeting Bacteria, green). b2: same detail, stained with probe mix Delta495 (targeting SRB, yellow). b3: overlay of details 1 and 2. b4: same detail, reference-stained with DAPI (blue).

The morphology of the bacteria in the biofilm was diverse, ranging from single cocci to aggregates, filaments, oval-, rod- and helix-shaped. The percentage of bacteria was estimated at 5%, confirming results from qPCR and previous studies (Henneberger et al., 2006). Interestingly, 85.4% (±4.7% s.d.; 15 biofilm samples analyzed) of cells stained with the bacterial probe also exhibited signals for the SRB385 probe (FIG. 12A). This percentage of SRB was confirmed by the usage of the Delta495 probe mix, which revealed an amount of 89.2% (±0.9% standard deviation; four biofilm samples analyzed) SRB (FIG. 12B).

Figure 11:
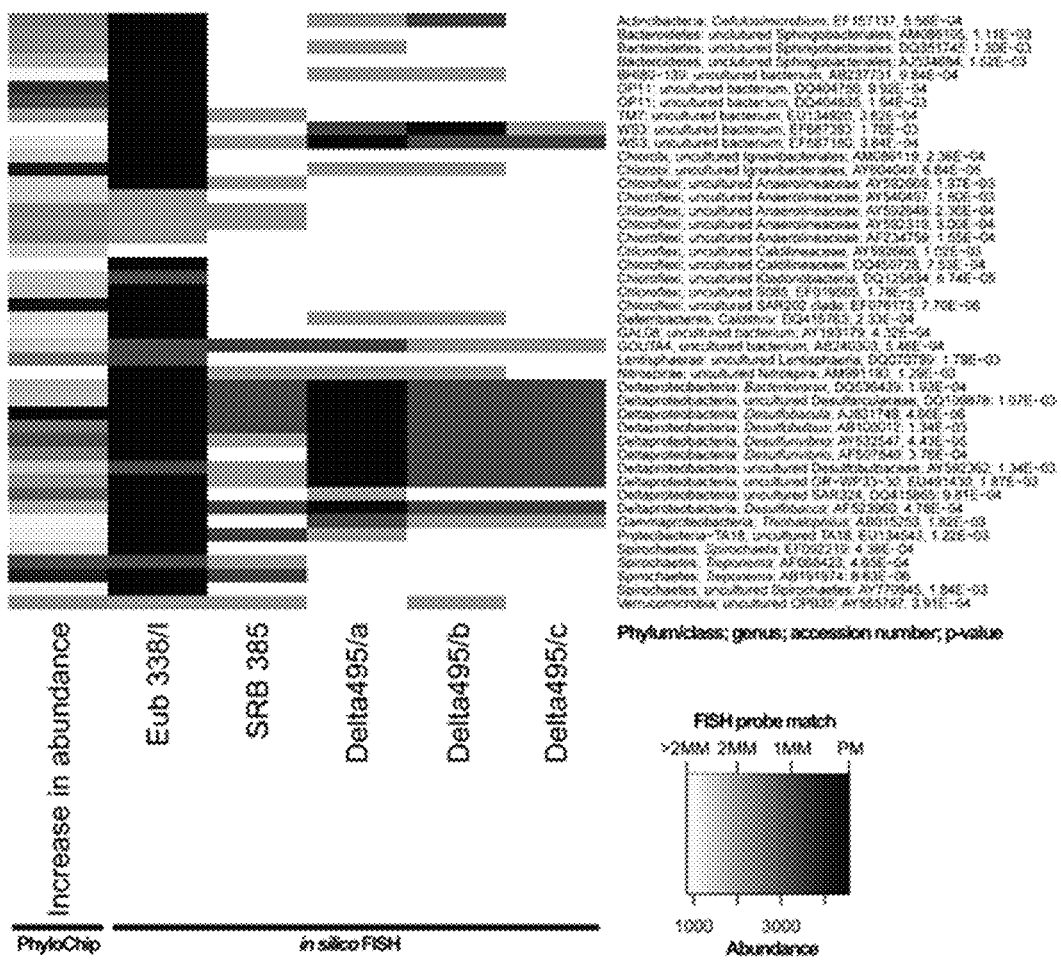
FIG. 11. Significantly enriched OTUs (one representative of each subfamily) in the SM1 Euryarchaeon biofilm and in silico FISH-probe match. Heatmap of OTUs that increased highly significantly (P<0.002) in biofilm compared with string-of-pearls community samples and were called present in at least one of the samples (first column), Probes used for FISH experiments in this study were in silico matched to representative sequences of the enriched OTUs using the ARB software package. The theoretical coverage of the FISH probes is displayed in columns 2-5; the decreasing heatmap intensity reflects the number of mismatches of each probe per OTU (MM=mismatch, PM=perfect match).

In order to correlate FISH data with enriched OTUs detected by PhyloChip analysis, the theoretical coverage of the Bacteria- and sulfate-reducer directed FISH probes was analyzed in silico (FIG. 11). All probes (SRB385, Delta495 probe mix and EUB 338/I) showed theoretical coverage of the target group (SRB), and therefore confirmed our FISH results. Interestingly, 29.4% of all bacterial cells that did not stain with the Delta495 probe mix exhibited a typical Spirochaeta-like morphology. This genus was also found to be highly enriched in the biofilm, but whose 16S rRNA reveals >2 mismatches for the Delta495 probe mix (FIG. 11).

Based on the high percentage of the SRB385 probe and the Delta495 probe mix stained bacteria, the PhyloChip and in silicon FISH analysis it can be concluded that the major part of bacteria in the biofilm can be affiliated to members of the Deltaproteobacteria, most likely to one specific, enriched OTU (genus *Desulfobacula* AJ831749). Cultivated members within the genus *Desulfobacula* were described as oval-shaped; bacteria with this morphology were positively stained with SRB and Delta495 probes and formed aggregates in the biofilm. (FIG. 12B).

Detection of dsrB Genes in Biofilm Samples.

In order to further prove the presence of SRB and their metabolic capability, qPCR with dsrB-directed primers was performed. We were able to specifically detect the presence of genes encoding dsrB and to quantify their amount (FIG. 9). The abundance of detectable dsrB genes in biofilm samples allowed the conclusion that these signatures were derived from bacteria and not from the dominant SM1 Euryarchaeon (three-log difference in archaeal 16S rRNA and dsrB gene abundance). Moreover, the one-log difference of bacterial 16S rRNA and dsrB genes can be attributed to the fact that ribosomal genes can have up to 15 copies per genome (Klappenhach et al., 2001; Lee et at, 2009), whereas dsrBgenes generally appear once (Heidelberg et al., 2004).

A clone library generated from the dsrB amplicons showed four different OTUs of dsrB genes belonging to the Deltaproteobacteria cluster, whereas one OTU was dominant (Accession no. JX515394: 33 clones; Accession no. JX515395; 11 clones; Accession no. JX515396; 3 clones, Accession no. JX515397; 1 clone). The coverage of the library was determined as 98%.

Metabolic Activity of SRB in the Biofilm.

A combination of CTC staining and FISH analysis showed an overlap of signals from CTC and SRB-directed FISH probes (Delta495 probe mix) in biofilm samples that were incubated in spring water anaerobically (FIG. 21A-D). The formation of CTC-formazan precipitates can be attributed to biological redox reactions, for example, respiratory electron transport, and thus provide evidence for the metabolic activity (Stellmach, 1984; Stellmach and Severin, 1986; Yoshida and Hiraishi, 2004).

SR-FTIR Measurements of Bacteria, Archaea, and Metabolic Intermediates Distributions in Biofilms.

Figure 13A:
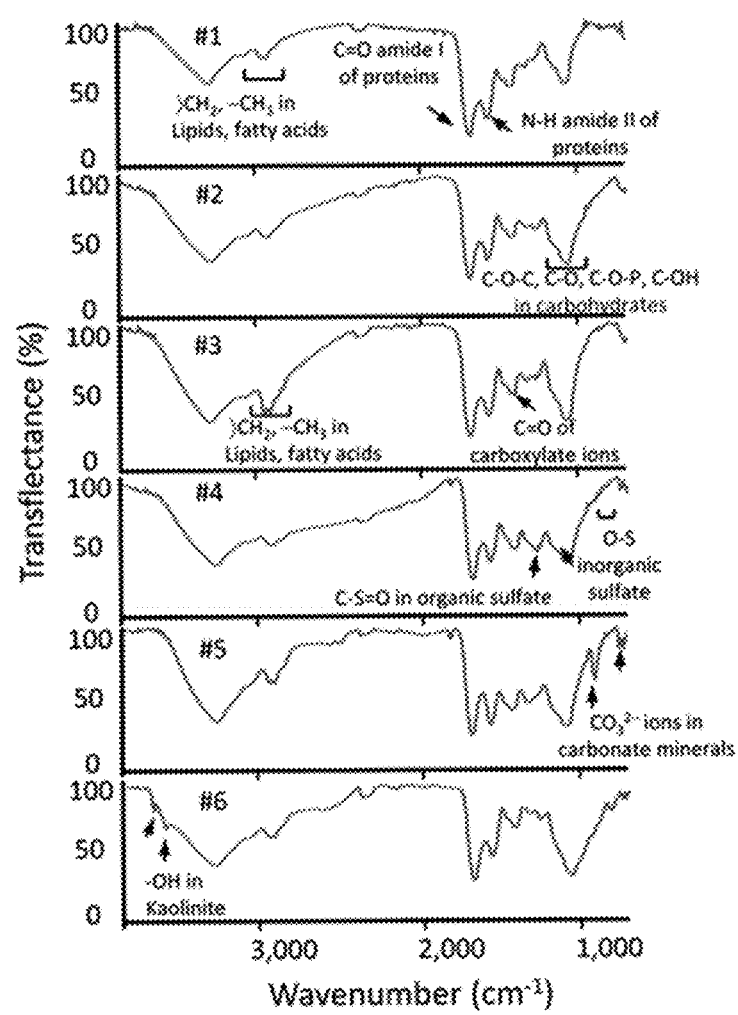
Figure 13B:
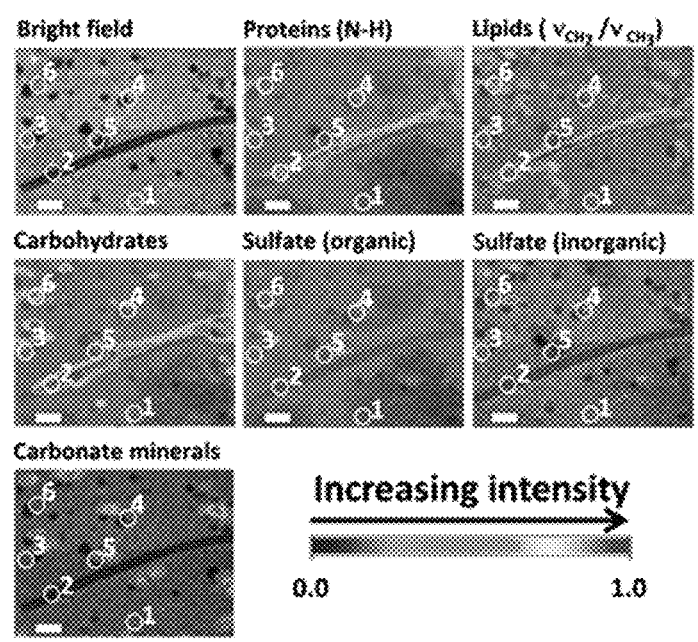
Figures 13D, 14:
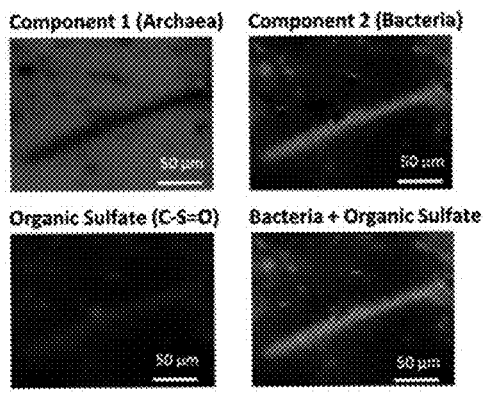

The high brightness of SR-FTIR spectromicroscopy enabled us to identify the presence of Bacteria, Archaea and a number of metabolic intermediates at a spatial resolution between 2 and 10 µm. Biofilm samples were first examined with crossed polarized microscopy and fluorescence microscopy because the biofilm fraction often exhibits visually interesting biogeochemical structures (FIG. 22). Then the spatial distribution of molecular composition and possible metabolites in the biofilm were analyzed by SR-FTIR spectromicroscopy. FIG. 13A shows examples of a range of typical SR-FTIR spectra collected on the biofilm samples (FIG. 13B, white circles in bright field). A striking feature was that these spectra, although obtained at locations merely several tens of micrometer apart (see circles in FIG. 13B), contained distinctly different signatures known to be associated with organic and inorganic markers typical of biogeochemical systems (FIG. 14). Spatial distributions of the infrared absorption intensities (from univariate analysis) of these molecular markers are shown in FIG. 13B. Notice that the infrared absorption intensity ratio of CH2 to CH3 was ~30% higher in the biofilm regions occupied by large, filamentous-shaped, Beggiatoa-like bacteria, compared with the surrounding Archaea-dominated area.

Figure 1A:
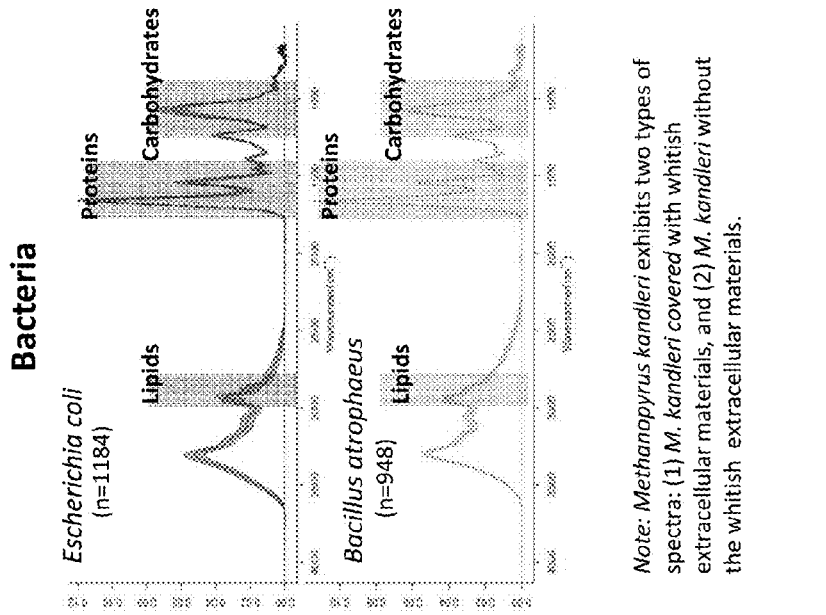
FIG. 1A-B. Comparison of vibrational spectra of the reference archaea and bacteria in the lipid region (2800-3100 $cm^{-1}$), the carbohydrate region (1000-1280 $cm^{-1}$), and the molecular fingerprint region (1480-650 $cm^{-1}$). SR-FTIR validation experiments: comparison of reference archaea (FIG. 1A) and bacteria (FIG. 1B). Comparison of SR-FTIR spectra of reference archaea and bacteria in the 4000-650 cm–1 region reflecting individual membrane lipids and cell envelope compositional characteristics (see Materials and methods section). All spectra are mean±standard deviation (colored area).
Figure 1B:
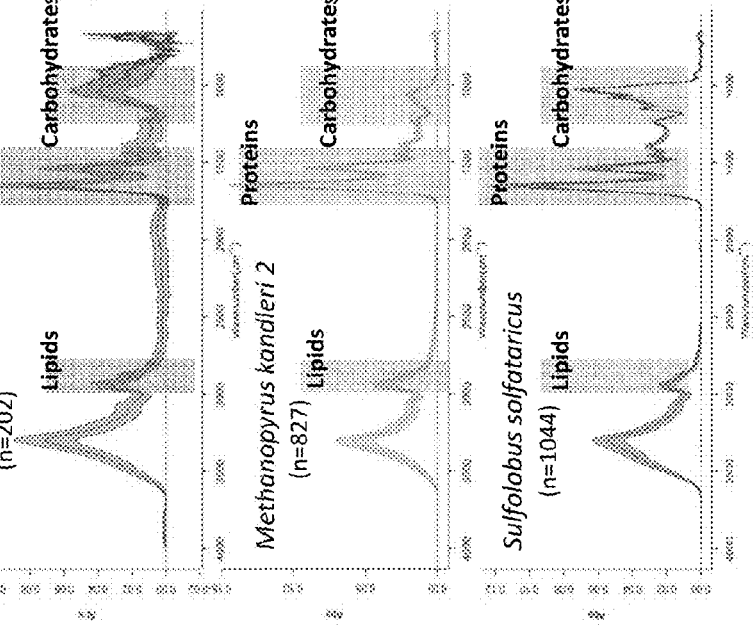
Figure 2A:
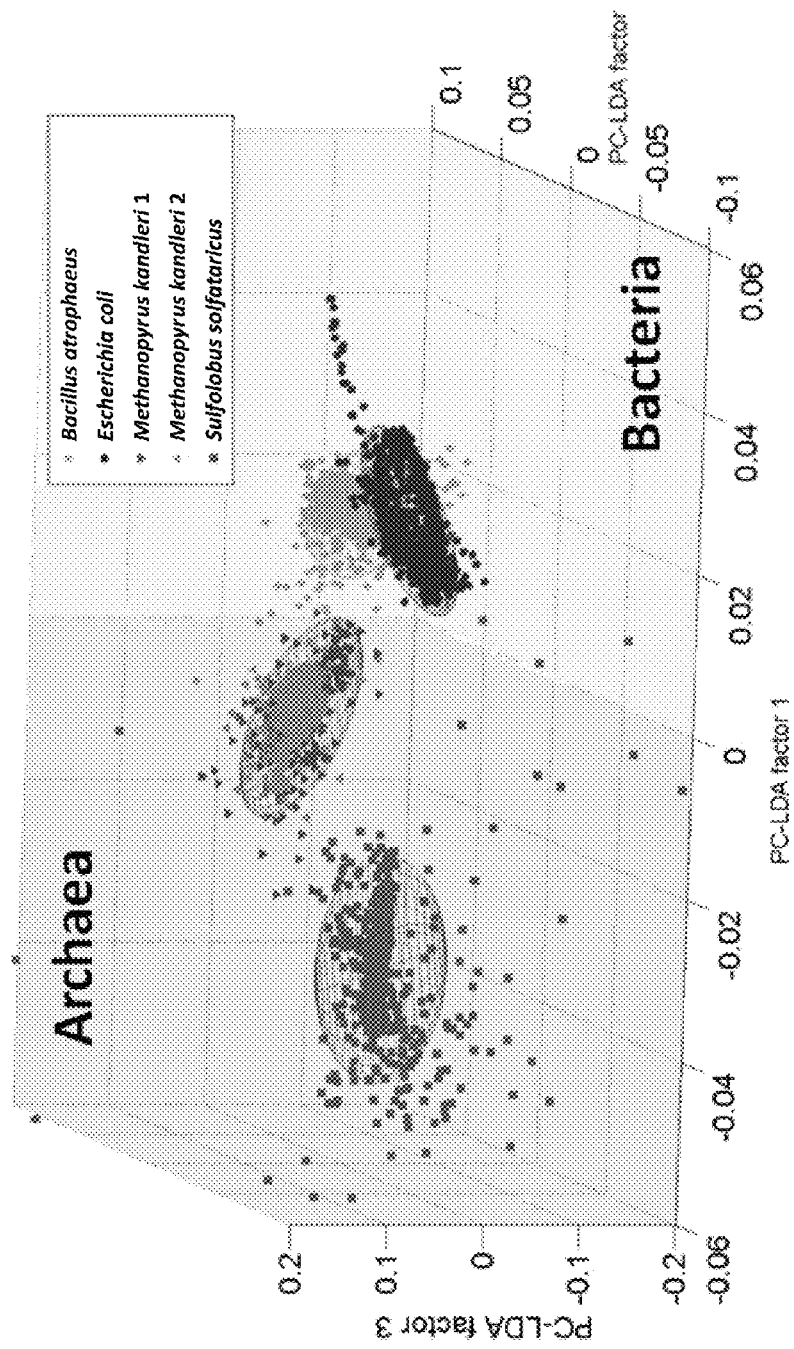
FIG. 2A shows Principal component-linear discriminant analysis (PC-LDA) of the reference bacterial and archaeal spectra in the CH vibration region (3100-2800 $cm^{-1}$). Three-dimensional PC-LDA score plots reveal an excellent separation of archaea and bacteria along the first PC-LDA factor, each ellipse covers an area of 95% confidence level. The three components explain 92.7% of the variance.
Figure 2B:
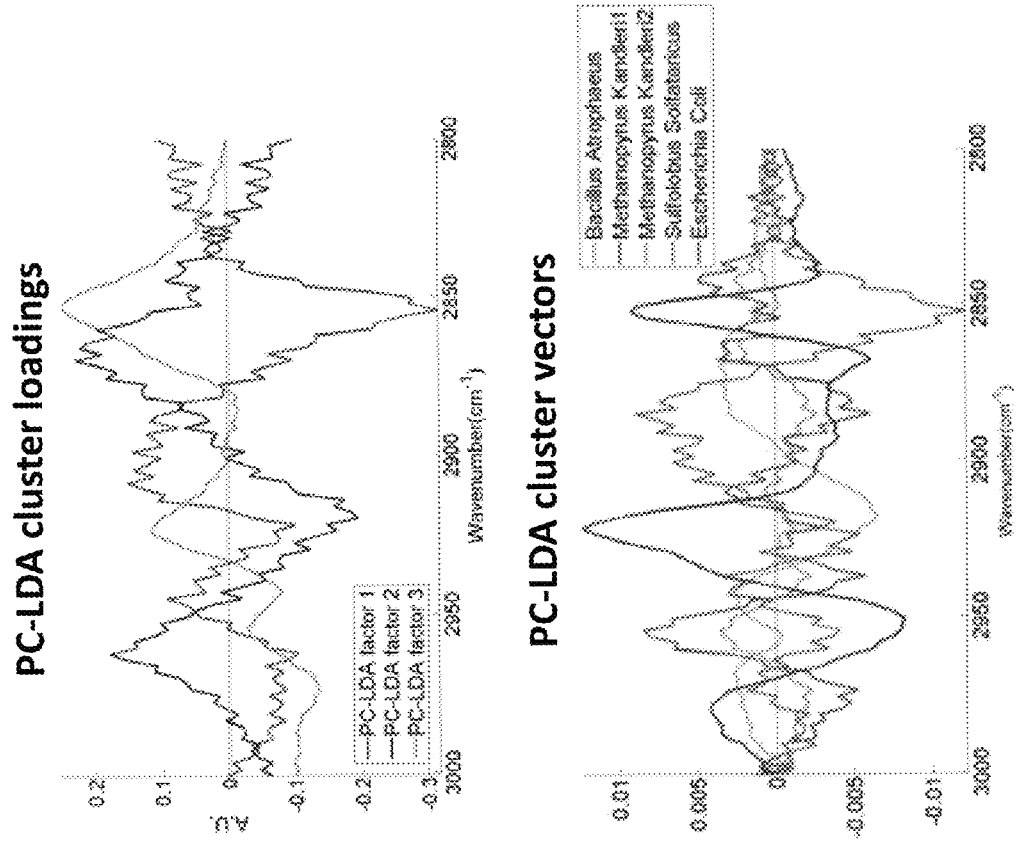
FIG. 2B shows the first PC-LDA loading spectrum has two distinct peaks at 2920 $cm^{-1}$ and 2850 $cm^{-1}$ (see arrows) which are associated with CH2 bond stretching. The corresponding cluster vector spectra reveal more specific membrane lipids composition and organization variations among the reference strains.
Figure 23A:
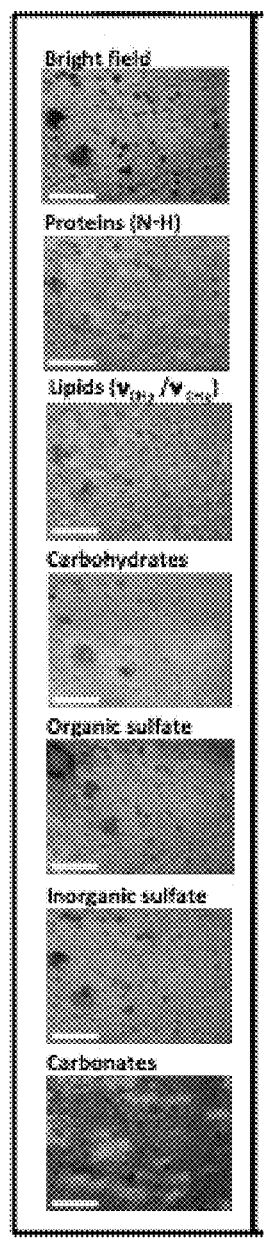
Figure 23B:
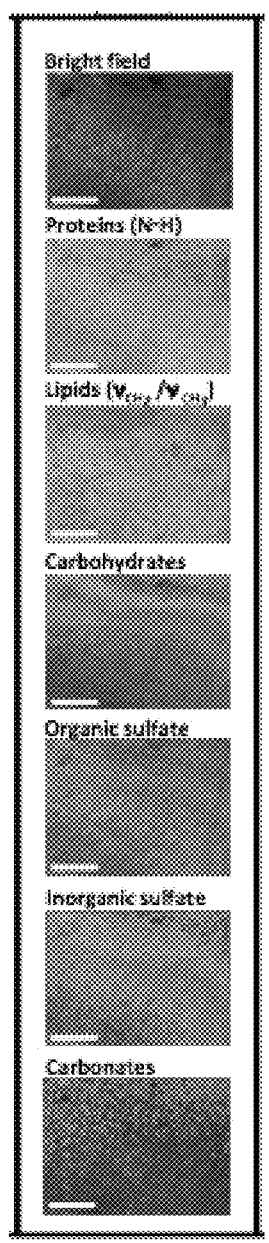
Figure 23C:
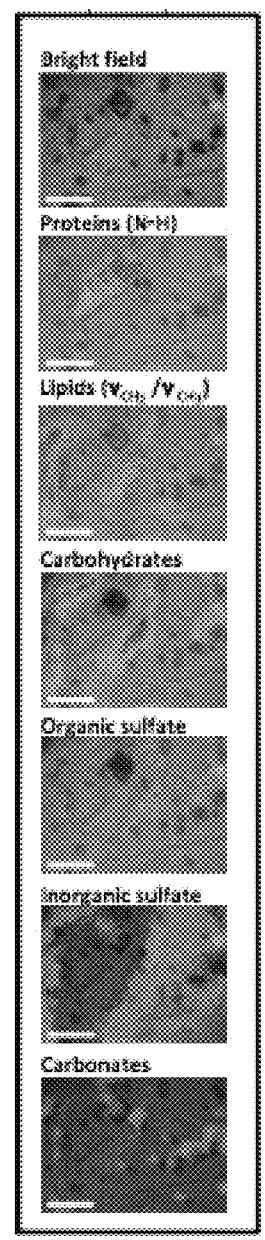
Figure 24A:
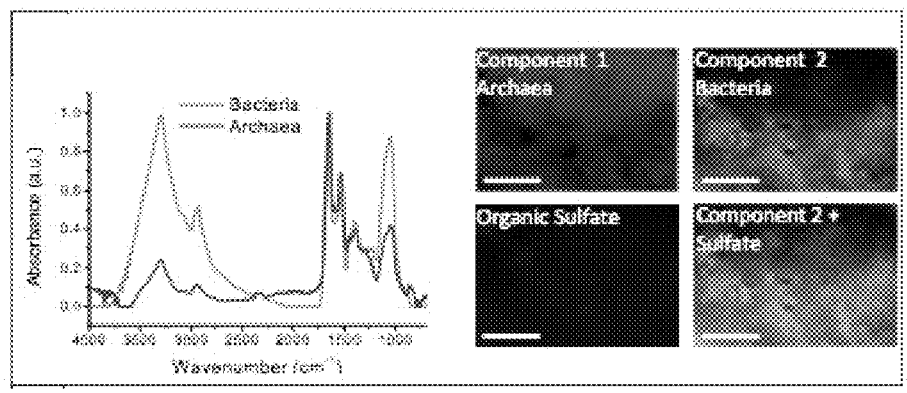
FIG. 24A-C. Multivariate curve resolution (MCR) SR-FTIR and univariate SR-FTIR images (~220 µm by ~180 µm) of three biofilms collected from the sulfidic spring Muehlbacher Schwefelquelle. The MCR recovered component spectra are in the upper left panels, the corresponding relative concentration images are in the two upper right panels. Chemical distribution map of organic sulfate (univariate map of R—S=O moiety) is in the two lower left panels. The merging of MCR component 2 and the organic sulfate compound is in the lower right panel. Samples FIGS. 24A, 24B, and 24C correspond to samples A, B, and C in FIG. 48, respectively. Scale bars=50 µm.
Figure 24B:
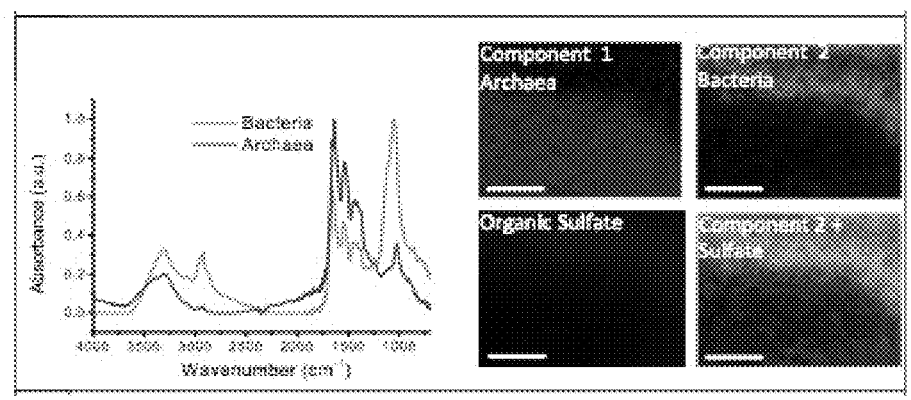
Figure 24C:
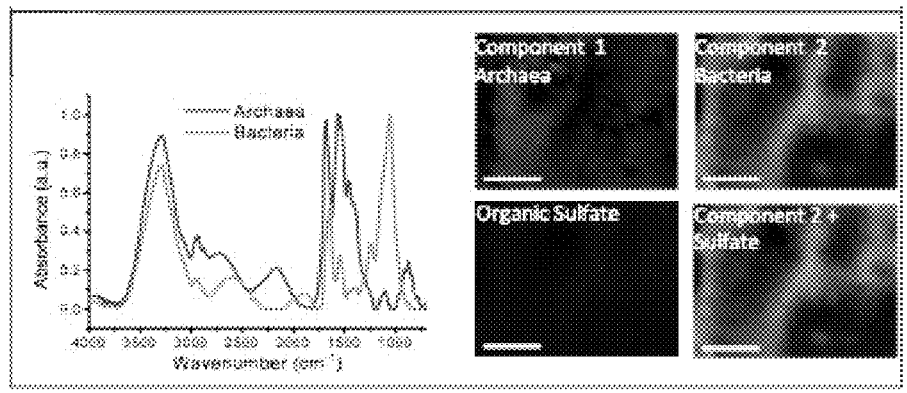

MCR analysis confirmed that Bacteria can be distinguished from Archaea by their spectral features (FIG. 13C versus FIGS. 1A and 2A and 2B; FIG. 13D versus FIG. 17, FIGS. 16A-D versus FIGS. 2A and 2B). Furthermore, specific metabolites as well as biogeochemical materials were found associated with these prokaryotic groups (FIGS. 13C and 13D). For example, in FIG. 13D, a combined univariate and MCR SR-FTIR analysis revealed strikingly overlapping infrared signals of organic sulfate products (R—S=O) and carbonate minerals with Bacteria-rich areas. Similar results were observed in other samples collected during this field experimental period (FIG. 23 and FIG. 24). This implies the presence of microscale mixtures of bacteria that are involved in subsurface sulfur and carbon turnover.

Discussion.

Life in the subsurface is highly diverse and comprises an enormous fraction of Earth's biomass. However, the microbial community living in this extreme environment remains largely mysterious, as subsurface biotopes are hardly accessible, which makes it also difficult to understand ongoing geochemical processes in these environments (Onstott et al., 2009). The Muehlbacher Schwefelquelle, however, provides an extraordinary window to the subsurface and allowed the discovery of a highly unusual, Archaea-dominated microbial community (the SM1 euryarchaeal biofilm), which is continuously being washed up from the subsurface and can be harvested from the spring water. As the dominant SM1 Euryarchaeon still resists efforts to be cultivated and metabolically understood, this study focused on the bacterial minority thriving in this type of biofilms. Using a combined approach of molecular techniques and SR-FTIR spectromicroscopy, we demonstrated that the interplay between the underrepresented bacterial fraction and geologically important chemicals could be analyzed in order to obtain insights into a possible ecological role of this extraordinary microbial community.

The dominance of one specific archaeon, the SM1 Euryarchaeon, was revisited and confirmed in this study by qPCR techniques and FISH, proving the constancy of this subsurface system over several years (Henneberger et al., 2006). The sensitive PhyloChip technology also confirmed the abundance of the SM1 Euryarchaeon, but additionally identified the presence of other archaea disproving the initial statement of an 'archaeal monospecies biofilm' (Henneberger et al., 2006). Nevertheless, because none of these alternate archaea was visualized either in FISH or in the archaeal clone library, it can be assumed that they represent only a very minor fraction of the biofilm.

We demonstrated that the spectral features of membrane lipids can be used to distinguish Archaea from Bacteria even in complex samples without using either a MS- or a nucleic acid-based approach (Sprott, 1992; Exert et al., 2000; Sturt et al., 2004). Furthermore, we also could use SR-FTIR to map the distribution of biogeochemical compounds, and to relate this molecular information to certain dominant ecological functions of even underrepresented microbial groups.

Raman microspectroscopy has often been used to characterize spatial distribution and molecular composition of biological samples (Wagner, 2009; Beier et al., 2010; Hall et al., 2011; Li et al., 2012). However, to date, Raman microscopy has often been used together with FISH (Raman-FISH) to differentiate microbial populations such as Bacteria and Archaea (Huang et al., 2007). On the contrary, SR-FTIR does not require cell labeling. SR-FTIR is also non-destructive, and therefore allows additional in situ studies of chemical composition changes in microbes on the same sample (Holman et al., 2010). As demonstrated in this study SR-FTIR spectromicroscopy imaging could associate the distribution of Archaea and Bacteria with biogeochemical compounds, giving us the opportunity to gain a more in-depth insight of the underpinning biogeochemical processes. In FIG. 13A-13D, for example, large, filamentous bacterial cells were observed along with increases in organic sulfate intensities, which suggests that these bacteria could belong to an sulfur-accumulating and -oxidizing bacterium such as Beggiatoa (Larkin and Strohl, 1983), a genus also identified in the biofilm core microbiome.

In other biofilm samples, such as those presented in FIG. 23 and FIG. 24, a majority of the areas that exhibited infrared spectral signatures of bacterial cells coincides with signals that are indicative of an accumulation of organic sulfate. The increasing sulfate signals could imply the presence of compounds such as adenosine-5'-phosphosulfate), 3'phosphoadenosine-5'phosphosulfate or sulfolipids (Goren, 1970). However, adenosine-5'-phosphosulfate is a typical intermediate of metabolically active either assimilatory or dissimilarity SRB and sulfur-oxidizing bacteria.

qPCR assays were able to detect a high amount of dsrB genes of Deltaproteobacteria, which were also identified by the PhyloChip G3 technology to be highly enriched in the biofilm. In FISH analyses of multiple biofilms a vast majority of the bacteria showed a positive signal after hybridization with two different (sets of) SRB-directed probes (the 385 probe and the Delta495a/b/c probe mix). This observation was supported by the CTC-FISH assay, which showed metabolic activity of bacteria stained with the Delta495 probe mix (see FIG. 21). These investigations confirmed that the bacterial microbiome of the SM1 Euryarchaeon biofilm is comprised mostly of Deltaproteobacteria, involved in sulfate reduction.

The fact that little sulfate signals were detected in the Archaea-rich regions implies two possible scenarios for the samples taken. In the first scenario, the supposed sulfate-reducing SM1 Euryarchaeon might be alive but metabolically inactive, having already reduced most of the sulfate compounds in its direct vicinity of the biofilm. In the second scenario, the SM1 Euryarchaeon might not be capable of sulfate reduction, a conclusion which is in stark contrast to the previous hypothesis (Moissl et al., 2002).

A number of metabolic pathways of SRB-associated archaea have already been reported in literature. For instance, in the AMO consortium SRB have a key role for archaeal, anaerobic methane oxidation (Orphan et al., 2001). However, it still remains unclear if the SM1 Euryarchaeon is capable of methane-oxidation or methanogenesis, or if it performs a completely different metabolism. Nevertheless it can be speculated, that a classical methanogen would quickly be outcompeted by SRB for hydrogen or organic substrates in sulfate-rich, anoxic environments such as the Muehlbacher Schwefelquelle (Lovley and Klug, 1983). Previous investigations have failed to detect F420, a key co-enzyme for methanogenesis, showing no positive amplification of the according gene, nor a positive chemical detection based on chromatography (Moissl et al., 2003).

Possible metabolic functions of the SM1 Euryarchaeon remain speculative but may be responsible for the environmental success of this organism. As the SM1 Euryarchaeon is currently the only known archaeon to absolutely predominate one specific biotope, combined with its appearance in hot spots in Europe and maybe even beyond (Rudolph et al., 2004), a larger (ecological) role can be assumed, which is currently still mysterious. However, a metagenomic study of the biofilm is currently performed, for which the knowledge about the microbial diversity is an important and very helpful prerequisite. This approach may reveal the metabolic capabilities of the SM1 Euryarchaeon in the biofilm.

Although a broad diversity of microbes is detectable in the Muehlbacher Schwefelquelle biotope, the accumulation of SRB, which represent the overwhelming majority of the minor bacterial part, appears to not be an accident; rather it is clear that these bacteria provide a valuable function within the biofilm as their presence in the biofilm was monitored as its discovery more than 8 years ago. However, the open question is if and how the SM1 Euryarchaeon influences the (bacterial) diversity in the biofilm. Does it—as it seems to be obvious for living together with (selected) filamentous sulfide-oxidizers in surface waters—actively recruit SRB to the biofilm, or is this phenomenon a passive enrichment? How and why does the SM1 Euryarchaeon switch from biofilm to string-of-pearls community status and are transition states detectable? These and many more questions will have to be answered in future studies and promise astonishing insights into this fascinating natural archaeal system.

REFERENCES 1

Adler H H, Kerr P F. (1965). Variations in infrared spectra, molecular symmetry and site symmetry of sulfate minerals. Am Mineralogist 50: 132-147.

Altschul S F. Gish W, Miller W, Myers E W, Lipman D J. (1990). Basic local alignment search tool. J Mol Biol 215: 403-410.

Amann R I, Binder B J, Olson R J, Chisholm S W, Devereux R, Stahl D A. (1990a). Combination of 16S rRNA-targeted oligonucleotide probes with flow cytometry for analyzing mixed microbial populations. Appl Environ Microbic 56: 1919-1925.

Amann R I, Krumholz L, Stahl D A. (1990b). Fluorescent-oligonucleotide probing of whole cells for determinative, phylogenetic, and environmental studies in microbiology. J Bacteriol 172: 762-770.

Ashelford K E, Chuzhanova N A, Fry J C, Jones A J, Weightman A J. (2005). At least 1 in 20 16S rRNA sequence records currently held in public repositories is estimated to contain substantial anomalies. Appl Environ Microbiol 71: 7724-7736.

Asker M M S, Mohamed S F, Ali F M, El-Sayed O H. (2007). Chemical structure and antiviral activity of water-soluble sulfated polysaccharides from Surgassum latifolium. J Appl Sci Res 3: 1178-1185.

Beier B D, Quivey R G, Berger A J. (2010). Identification of different bacterial species in biofilms using confocal Raman microscopy. J Biomed Opt 15: 06001-1-06001-5.

Beniash E, Aizenberg J, Addadi L, Weiner S. (1997). Amorphous calcium carbonate transforms into calcite during sea-urchin larval spicule growth. Proc R Soc Lond B: 461-465.

Budevska B O, Sum S T, Jones T J. (2003). Application of multivariate curve resolution for analysis of FT-IR microspectroscopic images of in situ plant tissue. Appl Spectrosc 57: 124-131.

Burggraf S, Olsen G I, Stetter K O, Woese C R. (1992). A phylogenetic analysis of Aquifex pyrophilus. Syst Appl Microbiol 15: 352-356.

Carr G L, Reffner J A, Williams G P. (1995). Performance of an Infrared Microspectrometer at the Nsls. Rev Sci Instrum 66: 1490-1492.

Cole J R, Wang Q, Cardenas E, Fish J, Chai B, Farris R J et al (2009). The Ribosomal Database Project: improved alignments and new tools for rRNA analysis. Nucleic Acids Res 37: D141-D145.

Dekas A E, Poretsky R S, Orphan V J. (2009). Deep-sea archaea fix and share nitrogen in methane-consuming microbial consortia. Science 326: 422-426.

DeLong E R (1998). Everything in moderation: archaea as 'non-extretnophiles'. Curr Opin Genet Dev 8: 649-654.

DeSantis T Z, Hugenholtz P, Larsen N, Rojas M, Brodie E L, Keller K. et al (2006). Greengenes, a chimera-checked 16S rRNA gene database and workbench compatible with ARB. Appl Environ Microhiol 72: 5069-5072.

Dumas P, Miller L M, Tobin M J. (2009). Challenges in biology and medicine with synchrotron infrared light. Acta Phys Pol A 115: 446-454.

Elvert M, Suess E, Greinert J, Whiticar M J. (2000). Archaea mediating anaerobic methane oxidation in deep-sea sediments at cold seeps of the eastern Aleutian subduction zone. Org Geochem 31: 1175-1187.

Engel A S, Lee N, Porter M L, Stern L A, Bennett P C, Wagner M. (2003). Filamentous "Epsilonproteobacteria" dominate microbial mats from sulfidic cave springs. Appl Environ Microbiol 69: 5503-5511.

Engel A S, Porter M L, Stern L A, Quinlan S, Bennett P C. (2004). Bacterial diversity and ecosystem function of filamentous microbial mats from aphotic (cave) suifidic springs dominated by chemolithoautotrophic "Epsilonproteobacteria". FEMS Microbiol Ecol 51: 31-53.

Frois S, Ajon M, Wagner M, Teichmann D, Zolghadr B, Folea M et al (2008). UV-inducible cellular aggregation of the hyperthermophilic archaeon Sulfolobus solfataricus is mediated by pili formation. Mol Microbiol 70: 938-952.

Geets J, Borremans B, Diels L, Springael D, Vangronsveld J, van der Lelie D et al (2006). DsrB gene-based DGGE for community and diversity surveys of sulfate reducing bacteria. J Microbiol Methods 66: 194-205.

Good I J. (1953), The population frequencies of species and the estimation of population parameters. Biometrika 40: 237-264.

Goren M B. (1970). Sulfolipid I of *Mycobarterium tuberculosis*, strain H37Rv II, Structural studies, Biochem Biophys Acta 210: 127-138.

Hall E K, Singer G A, Pölzl M, Hammerle I, Schwarz C, H et al (2011). Looking inside the box: using Raman microspectroscopy to deconstruct microbial biomass stoichiometry one cell at a time. ISME J 5: 196-208.

Hatzenpichler R, Lebedeva E V, Spieck E, Stoecker K, Richter A, Daims H et al (2008). A moderately thermophilic ammonia-oxidizing crenarchaeote from a hot spring. Proc Natl Acad Sci USA 105: 2134-2139.

Hazen T C., Dubinsky E A, DeSantis T Z, Andersen G L, Piceno Y M, Singh N et al (2010). Deep-sea oil plume enriches indigenous oil-degrading bacteria, Science 330: 204-208.

Heidelberg J F, Seshadri R, Haveman S A, Hemme C L, Paulsen I T, Kolonay I F et al (2004). The genome sequence of the anaerobic, sulfate-reducing bacterium *Desulfovibrio vulgaris* Hildenborough. Nat Biotechnol 22: 554-559.

Henneberger R, Moissl C, Amann T, Rudolph C, Huber R. (2006). New insights into the lifestyle of the cold-loving SM1 euryarchaeon: natural growth as a monospecies biofilm in the subsurface. Appl Environ Microbiol 72: 192-199.

Holman H Y, Bechtel H A, Hao Z, Martin M C. (2010). Synchrotron IR spectromicroscopy: chemistry of living cells. Anal Chem 82: 8757-8765.

Holman H Y, Wozei E, Lin Z, Comolli L R, Ball D A, Borglin S et al (2009). Real-time molecular monitoring of chemical environment in obligate anaerobes during oxygen adaptive response. Proc Natl Acad. Sci USA 106: 12599-12604.

Huang C K, Kerr P F. (1960). Infrared study of the carbonate minerals. The American Mineralogist 45: 311-324.

Huang W E, Stoecker K, Griffiths R, Newbold L, Daims H, Whiteley A S et al (2007). Raman-FISH: combining stable-isotope Raritan spectroscopy and fluorescence in situ hybridization for the single cell analysis of identity and function. Environ Microbiol 9: 1878-1889.

Kamer M B, DeLong F E, Karl D M. (2001). Archaeal dominance in the mesopelagic zone of the Pacific Ocean. Nature 409: 507-510.

Klappenbach J A, Saxman P R, Cole J R, Schmidt T M. (2001). rrndb: the ribosomal RNA operon copy number database. Nucleic Acids Res 29: 181-184.

Kodama Y, Watanabe K. (2004). *Sulfuricurvum kujiense* gen, *nov*., sp. *nov*., a facultatively anaerobic, chemolithoautotrophic, sulfur-oxidizing bacterium isolated from an underground crude-oil storage cavity. Int J Syst Evol Microbiol 54: 2297-2300.

Lane D. I. (1991). 1.6S/23S rRNA sequencing. In: Stackebrandt E, Goodfellow M (eds) Nucleic Acid Techniques in Bacterial Systematics. John Wiley & Sons: Chichester, pp. 115-175.

Lapaglia C, Hartzell P L. (1997). Stress-induced production of biofilm in the hyperthermophile *Archaeoglobus fulgidus*. Appl Environ Microbiol 63: 3158-3163.

Larkin J M, Strobl W R. (1983). Beggiatoa, Thiothrix, and Thioploca, Annu Rev Microbiol 37: 341-367.

Ledoux R L, White J L. (1964). Infrared study of the OH groups in expanded kaoline. Science 143: 244-246.

Lee Z M, Bussema C, Schmidt T M. (2009). rrnDB: documenting the number of rRNA and tRNA genes in bacteria and archaea, Nucleic Acids Res 37: D489-D493.

Letunic I, Bork P. (2007). Interactive Tree Of Life (iTOL): an online tool for phylogenetic tree display and annotation, Bioinformatics 23: 127-128.

Li M, Canniffe D P, Jackson P J, Davison P A, FitzGerald S, Dickman M J et al (2012). Rapid resonance Raman microspectroscopy to probe carbon dioxide fixation by single cells in microbial communities, ISME J 6: 875-885.

Lovley D R, Klug M J. (1983). Sulfate reducers can outcompete methanogens at freshwater sulfate concentrations. Appl Environ Microbiol 45: 187-192.

Loy A, Lehner A, Lee N, Adamczyk J, Meier H, Ernst J et al (2002). Oligonucleotide microarray for 16S rRNA gene-based detection of all recognized lineages of sulfate-reducing prokaryotes in the environment. Appl Environ Microbiol 68: 5064-5081.

Ludwig W, Strunk O, Westram R, Richter L, Yadhukumar Meier H et al (2004). ARB: a software environment for sequence data. Nucleic Acids Res32: 1363-1371.

Mancuso C A, Nichols P D, White D C. (1986). A method for the separation and characterization of archaebacterial signature ether lipids. J Lipid Res 27: 49-56.

Manders E E M, Verbeek F J, Aten J A. (1993). Measurement of co-localization of objects in dual-colour confocal images, Microsc 169: 375-382.

Mayers G L, Pausada M, Haines T H. 0969). Microbial Sulfolipids III. The dislfate of (+)-1,14-Docosanediol in *Ochromonas danica*. Biochemistry 8: 2981-2986.

Moissl C, Rachel R, Brie gel A, Engelhardt H, Huber R. (2005). The unique structure of archaeal 'hami', highly complex cell appendages with nano-grappling hooks, Mol Microhiol 56: 361-370.

Moissl C, Rudolph C, Huber R. (2002). Natural communities of novel archaea and bacteria with a string-of-pearls-like morphology: molecular analysis of the bacterial partners. Appl Environ Microbiol 68: 933-937.

Moissl C, Rudolph C, Rachel R, Koch M, Huber R. (2003). In situ growth of the novel SM1 euryarchaeon from a string-of-pearls-like microbial community in its cold biotope, its physical separation and insights into its structure and physiology. Arch Microbiol 180: 211-217.

Moissl-Eichinger C. (2011). Archaea in artificial environments: their presence in global spacecraft clean rooms and impact on planetary protection.

Moissl-Eichinger C, Huber H. (2011). Archaeal symbionts and parasites. Curr Opin Microbiol 14: 364-370.

Nauman D. (2000) Infrared Spectroscopy in Microbiology. John Wiley & Sons, Ltd.: Chichester.

Onstott T C, Colwell F S, Kieft T L, Murdoch L, Phelps T J. (2009). New horizons for deep subsurface microbiology. Microbe 4: 499-505.

Orphan V J, House C H, Hinrichs K U, McKeegan K D, DeLong E R (2001). Methane-consuming archaea revealed by directly coupled isotopic and phylogenetic analysis. Science 293: 484-487.

Palmer A N. (1991). Origin and morphology of limestone caves. Geol Sac Am Bull 103: 1-21.

Parker F S. (1983) Applications of Infrared, Raman, and Resonance Raman Spectroscopy in Biochemistry. Plenum Press: New York, 550 pp.

Peak D, Ford R G, Sparks D L. (1999). An in situ ATR-FTIR investigation of sulfate bonding mechanisms on goethite. J Colloid Interface Sci 218: 289-299.

Percival E, Wold J K. (1963). The acid polysaccharide from the green seaweed *Ulva lactuca*. Part II. The site of the ester sulphate. J Chem Soc, 5459-5468.

Pruesse E, Quast C, Knittel K, Fuchs B M, Ludwig W, Peplies J et al (2007). SILVA: a comprehensive online resource for quality checked and aligned ribosomal RNA sequence data compatible with ARB. Nucleic Acids Res 35: 7188-7196.

Rudolph C. (2003), Molekularbiologische Untersuchungen zur Verbreitung, and Physiologic neuartiger, unkultivierter Archaeen in kalten Schwefelquellen. Dissertation, University of Regensburg, Rudolph C, Moissl C, Henneberger R, Huber R. (2004). Ecology and microbial structures of archaeal/bacterial strings-of-pearls communities and archaeal relatives thriving in cold sulfidic springs. FEMS Microbiol Eco 150: 1-11.

Rudolph C, Wanner G, Huber R. (2001). Natural communities of novel archaea and bacteria growing in cold sulfurous springs with a string-of-pearls-like morphology. Appl Environ Microbiol 67: 2336-2344.

Schloss P D, Westcott S L, Ryabin I, Hall J R, Hartmann M, Hollister E B et al (2009). Introducing mother: open-source, platform-independent, community-supported software for describing and comparing microbial communities. Appl Environ Microbiol 75: 7537-7541.

Sinclair R G, McKay A F, Myers G S. Norman Jones R. (1952). The infrared absorption spectra of unsaturaed fatty acids and esters. J Am Chem Soc74: 2578-2585.

Smith B. (1999) Infrared Spectral Interpretation A Systematic Approach. CRC Press: Washington, D.C.

Sprott G D. (1992). Structures of archaebacterial membrane lipids. J Bioenerg Biomembr 24: 555-566.

Stellmach J. (1984). Fluorescent redox dyes 1. Production of fluorescent formazan by unstimulated and phorbal esteror digitonin-stimulated Ehrlich ascites tumor cells. Histochemistry 80: 137-143.

Stellmach J, Severin. E. (1986). A fluorescent redox dye. Influence of several substrates and electron carriers on the tetrazolium salt-formazan reaction of Ehrlich ascites tumor cells. Histochem J 19: 21-26.

Sturt H F, Summons R E, Smith K, Elven M, Hinrichs K U. (2004). Intact polar membrane lipids in prokaryotes and sediments deciphered by high-performance liquid chromatography/electrospray ionization multistage mass spectrometry—new biomarkers for biogeochemistry and microbial ecology. Rapid Commun Mass Spectrum 18: 617-628.

Takano B. (1985). Geochemical implications of sulfate in sedimentary carbonates. Chem Geo 49: 393-403.

Tamura K, Dudley J, Nei M, Kumar S. (2007). MEGA4: molecular evolutionary genetics analysis (MEGA) software version 4.0. Mol Biol Evol 24: 1596-1599.

Tillett D, Neilan B A. (2000). Xanthogenate nucleic acid isolation from cultured and environmental cyanobacteria. J Phycol 36: 251-258.

Tourna M, Stieglmeier M, Spang A, Konneke M, Schintimeister A, Urich T et al (2011). Nitrososphaera viennensis, an ammonia oxidizing archaeon from soil. Prov Nati Acad Sci USA 108: 8420-8425.

Tyson G W, Chapman J, Hugenholtz P, Allen E E, Ram R J, Richardson P M et al (2004). Community structure and metabolism through reconstruction of microbial genomes from the environment. Nature 428: 37-43.

Vaneechoutte M, Rossau R, De Vos P, Gillis M, Janssens D, Paepe N et al (1992). Rapid identification of bacteria of the Comamonadaceae with amplified ribosomal DNA-restriction analysis (ARDRA). FEMS Microbiol Lett 72: 227-233.

Wagner M. (2009). Single-cell ecophysiology of microbes as revealed by raman microspectroscopy or secondary ion mass spectrometry imaging. Annu Rev Microbiol 63: 411-429.

Wagner M, Roger A J, Flax J L, Brusseau G A, Stahl D A. (1998). Phylogeny of dissimilarity sulfite reductases supports an early origin of sulfate respiration. J Bacteriol 180: 2975-2982.

Walker C B, de la Torre J R, Klotz M G, Urakawa H, Pinel N, Arp D J et al (2010). *Nitrosopumilus maritimus* genome reveals unique mechanisms for nitrification and autotrophy in globally distributed marine crenarchaea. Proc Natl Acad Sci USA 107: 8818-8823.

Waliner G, Amann R, Beisker W. (1993), Optimizing fluorescent in situ hybridization with rRNA-targeted oligonucleotide probes for flow cytometric identification of microorganisms. Cytometry 14: 16-143.

White W B. (1974) The Carbonated Minerals. Mineralogical Society: London.

Whittaker P, Mossoha M M, Al-Khaldi S, Fry F S, Dunkel V C, Tall B D et al (2003). Identification of foodborne bacteria by infrared spectroscopy using cellular fatty acid methyl esters. J Microbiol Methods 55: 709-716.

Yoshida N, Hiraishi A. (2004). An improved redox dye-staining method using 5-cyano-2,3-ditoryl tetrazolium chloride for detection of metabolically active bacteria in activated sludge. Microbes Environ 19: 61-70.

REFERENCES 2

Abele G (1950). Die Heil-und Mineralquellen Südbayerns. Suppenau bei Saal an der Donau. Geologica Bavarica 2: 94-95.

Amann R I, Binder B J, Olson R J, Chisholm S W, Devereux R, Stahl D A (1990a). Combination of 16S rRNA-targeted oligonucleotide probes with flow cytometry for analyzing mixed microbial populations. Appl Environ Microbiol 56: 1919-1925.

Amann R I, Krumholz L, Stahl D A (1990b). Fluorescent-oligonucleotide probing of whole cells for determinative, phylogenetic, and environmental studies in microbiology. J Bacteriol 172: 762-770.

Andres G, Frisch H (1981). Hydrogeologie und Hydraulik im Malmkarst des Molassebeckens und der angrenzenden Fränkischen-Schwäbischen Alb. Schriftenreihe Bayer Landesamt f Wasserwirtschaft 15: 108-117.

Baumann M (1981). Hydrogeologische, hydrochemische und erschlieBungstechnische Verhältnisse der Schwefelquellen. Schriftenreihe Bayer Landesat f Wasserwirtschaft 15: 4-13.

Brodie E L, DeSantis T Z, Parker J P, Zubietta I X, Piceno Y M, Andersen G L (2007). Urban aerosols harbor diverse and dynamic bacterial populations. Proc Natl Acad Sci USA 104: 299-304.

Burggraf S, Olsen G J, Stetter K O, Woese C R (1992). A phylogenetic analysis of Aquifex pyrophilus. Syst Appl Microbiol 15: 352-356.

Castelle C J, Hug L A, Wrighton K C, Thomas B C, Williams K H, Wu D et al (2013). Extraordinary phylogenetic diversity and metabolic versatility in aquifer sediment. Nat Commun 4: 2120.

Cooper M, La Duc M T, Probst A, Vaishampayan P, Stam C, Benardini J N et al (2011). Comparison of innovative molecular approaches and standard spore assays for assessment of surface cleanliness. Appl Environ Microbiol 77: 5438-5444.

De Rosa M, Gambacorta A (1988). The lipids of archaebacteria. Prog Lipid Res 27: 153-175.

DeSantis T Z, Hugenholtz P, Larsen N, Rojas M, Brodie E L, Keller K et al (2006). Greengenes, a chimera-checked 16S rRNA gene database and workbench compatible with ARB. Appl Environ Microbiol 72: 5069-5072.

DeSantis T Z, Brodie E L, Moberg J P, Zubieta I X, Piceno Y M, Andersen G L (2007). High-density universal 16S rRNA microarray analysis reveals broader diversity than typical clone library when sampling the environment. Microb Ecol 53: 371-383.

Engel A S, Lee N, Porter M L, Stern L A, Bennett P C, Wagner M (2003). Filamentous "Epsilonproteobacteria" dominate microbial mats from sulfidic cave springs. Appl Environ Microbiol 69: 5503-5511.

Engel A S, Porter M L, Stern L A, Quinlan S, Bennett P C (2004). Bacterial diversity and ecosystem function of filamentous microbial mats from aphotic (cave) sulfidic springs dominated by chemolithoautotrophic "Epsilonproteobacteria". FEMS Microbiol Ecol 51: 31-53.

Hazen T C, Dubinsky E A, DeSantis T Z, Andersen G L, Piceno Y M, Singh N et al (2010). Deep-sea oil plume enriches indigenous oil-degrading bacteria. Science 330: 204-208.

Henneberger R, Moissl C, Amann T, Rudolph C, Huber R (2006). New insights into the lifestyle of the cold-loving SM1 euryarchaeon: natural growth as a monospecies biofilm in the subsurface. Appl Environ Microbiol 72: 192-199.

Holman H Y, Bechtel H A, Hao Z, Martin M C (2010). Synchrotron IR Spectromicroscopy: Chemistry of Living Cells. Anal Chem.

Koch M, Rudolph C, Moissl C, Huber R (2006). A cold-loving crenarchaeon is a substantial part of a novel microbial community in cold sulphidic marsh water. FEMS Microbiol Ecol 57: 55-66.

La Duc M T, Osman S, Vaishampayan P, Piceno Y, Andersen G, Spry J A et al (2009). Comprehensive census of bacteria in clean rooms by using DNA microarray and cloning methods. Appl Environ Microbiol 75: 6559-6567.

Lemcke K (1976). Übertiefe Grundgewässer im Süddeutschen Alpenvorland. BuU Ver Schweiz Petroleum-Geol u-Ing 42: 9-18.

Lane D J (1991). 16S/23S rRNA sequencing. Nucleic Acid Techniques in Bacterial Systematics.

Lovley D R, Chapelle F H (1995). Deep subsurface microbial processes. Reviews of Geophysics 33: 365-381.

Lovley D R, Coates J D (2000). Novel forms of anaerobic respiration of environmental relevance. Curr Opin Microbiol 3: 252-256.

Loy A, Lehner A, Lee N, Adamczyk J, Meier H, Ernst J et al (2002). Oligonucleotide microarray for 16S rRNA gene-based detection of all recognized lineages of sulfate-reducing prokaryotes in the environment. Appl Environ Microbiol 68: 5064-5081.

Lozupone C, Knight R (2005). UniFrac: a new phylogenetic method for comparing microbial communities. Appl Environ Microbiol 71: 8228-8235.

Lozupone C, Lladser M E, Knights D, Stombaugh J, Knight R (2011). UniFrac: an effective distance metric for microbial community comparison. ISME J 5: 169-172.

Mantsch H H, Chapman D (1996). Infrared Spectroscopy of Biomolecules. Wiley-Liss, Inc: New York.

McDonald D, Price M N, Goodrich J, Nawrocki E P, DeSantis T Z, Probst A et al (2012). An improved Greengenes taxonomy with explicit ranks for ecological and evolutionary analyses of bacteria and archaea. ISME J 6: 610-618.

Mendes R, Kruijt M, de Bruijn I, Dekkers E, van der Voort M, Schneider J H et al (2011). Deciphering the rhizosphere microbiome for disease-suppressive bacteria. Science 332: 1097-1100.

Miezeiewski M, Schnaufer T, Muraysky M, Wang S, Caro-Aguilar I, Secore S et al (2013). An in virto culture model to study the dynamics of colonic microbiota in syrian golden hamster and their susceptibility to infection with *Clostridium difficile*. Submitted to ISME J.

Moissl C, Rudolph C, Huber R (2002). Natural communities of novel archaea and bacteria with a string-of-pearls-like morphology: molecular analysis of the bacterial partners. Appl Environ Microbiol 68: 933-937.

Moissl C, Rudolph C, Rachel R, Koch M, Huber R (2003). In situ growth of the novel SM1 euryarchaeon from a string-of-pearls-like microbial community in its cold biotope, its physical separation and insights into its structure and physiology. Arch Microbiol 180: 211-217.

Moissl C, Rachel R, Briegel A, Engelhardt H, Huber R (2005). The unique structure of archaeal 'hami', highly complex cell appendages with nano-grappling hooks. Mol Microbiol 56: 361-370.

Moissl-Eichinger C (2011). Archaea in artificial environments: their presence in global spacecraft clean rooms and impact on planetary protection. ISME J 5: 209-219.

Morris B E, Henneberger R, Huber H, Moissl-Eichinger C (2013). Microbial syntrophy: interaction for the common good. FEMS Microbiol Rev 37: 384-406.

Nielsen H (1981). Schwefelisotope and ihre Aussage zur Entstehung der Schwefelquellen. Schriftenreihe Bayer Landesamt f Wasserwirtschaft 15: 99-107.

Ortiz M, Legatzki A, Neilson J W, Fryslie B, Nelson W M, Wing R A et al (2013). Making a living while starving in the dark: metagenomic insights into the energy dynamics of a carbonate cave. ISME J.

Pamler A N (1991). Origin and morphology of limestone caves. Geol Soc Am Bull 103: 1-21.

Probst A J, Holman H Y, DeSantis T Z, Andersen G L, Birarda G, Bechtel H A et al (2013). Tackling the minority: sulfate-reducing bacteria in an archaea-dominated subsurface biofilm. ISME J 7: 635-651.

Rudolph C, Wanner G, Huber R (2001). Natural communities of novel archaea and bacteria growing in cold sulfurous springs with a string-of-pearls-like morphology. Appl Environ Microbiol 67: 2336-2344.

Rudolph C, Moissl C, Henneberger R, Huber R (2004). Ecology and microbial structures of archaeal/bacterial strings-of-pearls communities and archaeal relatives thriving in cold sulfidic springs. FEMS Microbiol Ecol 50: 1-11.

Socrates G (2004). Infrared and Raman Characteristic Group Frequencies: Tables and Charts. Wiley.

Sprott G D (1992). Structures of archaebacterial membrane lipids. J Bioenerg Biomembr 24: 555-566.

Thirkell D, Gray E M (1974). Variation in the lipid and fatty acid composition in purified membrane fractions from Sarcina aurantiaca in relation to growth phase. Antonie van Leeuwenhoek 40: 71-78.

Ulrich G A, Martino D, Burger K, Routh J, Grossman E L, Ammerman J W et al (1998). Sulfur Cycling in the Terrestrial Subsurface: Commensal Interactions, Spatial Scales, and Microbial Heterogeneity. Microb Ecol 36: 141-151.

Ulrih N P, Gmajner D, Raspor P (2009). Structural and physicochemical properties of polar lipids from thermophilic archaea. Appl Microbiol Biotechnol 84: 249-260.

Vaishampayan P, Probst A J, La Duc M T, Bargoma E, Benardini J N, Andersen G L et al (2013). New perspectives on viable microbial communities in low-biomass cleanroom environments. ISME J 7: 312-324.

Whitman W B, Coleman D C, Wiebe W J (1998). Prokaryotes: the unseen majority. Proc Natl Acad Sci USA 95: 6578-6583.

Wrighton K C, Thomas B C, Sharon I, Miller C S, Castelle C J, VerBerkmoes N C et al (2012). Fermentation, hydrogen, and sulfur metabolism in multiple uncultivated bacterial phyla. Science 337: 1661-1665.

Example 2: Archaea-Dominated Subsurface Biofilms at Two Vicinal Springs Naturally Diverge from Microbiome to Strain-Level Earth harbors an enormous portion of subsurface microbial life, which remains mainly unexplored due to the difficult access to samples. The unique hydrogeological conditions of vicinal, sulfidic springs in southeast Germany provide accessible windows into the microbial and molecular diversity of subsurface biofilms dominated by the uncultivated SM1 Euryarchaeon. Although both springs are fed by one deep groundwater current and have similar physical and chemical parameters, our multidisciplinary approach revealed that site-specific hydrogeological conditions altered the microbiome at various levels, from the corn unity profile down to the strain level and could even create different ecological niches for the biofilm-forming archaea. The analyses of infrared imaging spectra demonstrated great variations in archaeal membrane composition, suggesting different SM1 euryarchaeal strains at both aquifer outlets. This observation is supported by ultrastructural and metagenomic analyses of the archaeal biofilms. However, on the microbiome level, PhyloChip G3 DNA microarray detected similar biofilm immunities for archaea, but not for bacteria. Although the biofilms showed an enrichment of different deltaproteobacteria, their function in sulfate-reduction appeared to be congruent. Consequently, the biofilms revealed striking differences due to hydrogeological variations despite their appearance at similar locations and dominance by the same archaeal species. The results of this communication provide deep insight into the dynamics of subsurface microbial life and warrant its future investigation with regard to metabolic and genomic analyses.

The subsurface biosphere harbors an enormous portion of the Earth's microbiome. It is estimated, that up to $2.9 \times 10^{29}$ and $2.2 \times 10^{30}$ prokaryotic cells reside below the surface layer in marine habitats and terrestrial sediments, respectively (Kallmeyer et al 2012, Whitman et al 1998). Sampling, and thus exploration of the subsurface microbiomes by deep drilling is difficult, since each sample is subject to a possible contamination by surface microorganisms (Whitman et al 1998). Currently, the subsurface biotope remains poorly understood as microbial and biogeochemical "dark matter", yet having a substantial contribution to carbon, nitrogen and sulfur cycling seems obvious (Ulrich et al 1998, Whitman et al 1998, Wrighton et al 2012). However, important windows to the subsurface are provided by aquifers and their natural and artificial springs (Castelle et al 2013, Wrighton et al 2012), delivering possibly $10^3$-$10^6$ prokaryotic cells/ml to the surface (Whitman et al 1998). Although sulfidic springs are rather rare (10% of all terrestrial aquifers; Pamler 1991)), they contain excellent energy sources for subsurface and also surface life: Once mixed with oxygen as terminal electron acceptor nutrients from sulfidic subsurface aquifers can lead to high amounts of biomass in the outflow region (Engel et al 2003, Engel et al 2004, Koch et al 2006, Moissl et al 2002, Moissl et al 2003, Rudolph et al 2001, Rudolph et al 2004). These biomasses, which are mostly complex microbial communities such as bacterial or archaeal/bacterial biofilms, have been the focus of many studies, yet the oxygen-free subsurface environment of sulfidic springs is lacking information concerning its biodiversity and variation over geographical location (Probst et al 2013).

In southeast Germany near Regensburg, sulfur springs rise out of the subsurface karst system in the Jurassic carbonate settings. Due to the hydro geological conditions, atmospheric oxygen mixed with the cold (~10° C.), anoxic sulfidic groundwater leads to a sudden increase in biomass, including the so-called "string-of-pearls community". In the "pearls", the uncultivated, phylogenetically deep-branching SM1 Euryarchaeon resides, surrounded by sulfur-oxidizing bacteria (*Thiothrix* sp., site "Sippenauer Moor", (Moissl et al 2002, Rudolph et al 2001)). In the subsurface of one of these springs these archaea were found to form an almost pure biofilm (site "Mülbacher Schwefelquelle" (Henneberger et al 2006)). There, the archaea are associated with a minor bacteriome, dominated by sulfate-reducing bacteria (Probst et al 2013). The constant predominance of the SM1 Euryarchaeon (>95%) in the biofilm was demonstrated by different methods and in hundreds of samples taken between 2005 and 2013 from the Mühlbacher Schwefelquelle (Henneberger et al 2006, Probst et al 2013). Minor investigations also included samples from the Sippenauer Moor, where the appearance of these biofilms was also observed but not further documented (Henneberger et al 2006). Although the SM1 Euryarchaeon is unusual in many ways (it forms pure biofilms, predominates within these environments and has extraordinary structural and biochemical traits; Moissl et al 2005, Rudolph et al 2001), it is considered a remarkable model system for cold archaea and subsurface research (Probst et al 2013).

In this study, we explored archived information on the hydrogeology of the two sulfidic springs that appeared to be supplied by the same deep waterflow. We consequently investigated microbial differences of subsurface biofilm samples from both sampling sites and specifically focused on the variation in the microbial composition, biochemical properties, the surface ultrastructure and fingerprinting of hamus (unique cell surface appendage, pl. hami) gene occurrence (Moissl et al 2005). Empirically determined operational taxonomic units (eOTUs) derived from PhyloChip G3 data were used for microbial community profiling on 16S rRNA gene level. To add an extra dimension to the knowledge of the biochemistry of the SM1 Euryarchaeon biofilms, we applied multivariate statistics to the chemical imaging data acquired by means of synchrotron radiation-based Fourier transform (SR-FTIR) spectromicroscopy.

Materials and Methods.

Site Description and Sampling.

The first sampling site was in the Sippenauer Moor (Bavaria, Germany; N48°52.111'E11°57.379'), a marsh region, where various springs form one streamlet before entering a small lake (Rudolph et al 2001, Rudolph et al 2004). Samples were collected by placing polyethylene nets directly at a spring outlet and at 0.65 m to 0.80 m distance to harvest milky, slimy biofilms and string-of-pearls community samples, respectively. These included three Sippenauer Moor biofilm (SM-BF) samples taken directly from a spring outflow where the oxygen and $H_2S$ concentrations were 0.02 mg/l and 0.85 mg/l, respectively, and six string-of-pearl community (SOPC) samples taken at a location where the outflows of three springs mix (oxygen concentrations were 0.89 and 1.10 mg/l respectively; sulfide concentration at mixing area: 0.5 mg/l.

The second sampling location was the Mühlbacher Schwefelquelle nearby Isling (MSI; linear distance 20 km to Sippenauer Moor; N48°59.140' E12°07.631'; Rudolph et al 2004, Henneberger et al 2006; FIG. 40). Three MSI biofilm (MSI-BF) samples were harvested in a similar manner, but under oxygen-free conditions (samples from Probst et al 2013); here, the $H_2S$ concentration was 0.85 mg/l and the oxygen concentration was below detection limit (details see: Probst et al 2013). The water composition of the two springs was documented earlier and showed high similarity (Rudolph et al 2004).

Sample Preparation.

Biofilm samples were removed from the polyethylene nets with syringes/pipettes and transported to the laboratory on ice. Samples for DNA extraction were stored at −20° C., and samples for SR-FTIR analyses were air-dried on gold-coated grids after removing the liquid (Probst et al 2013). Samples for whole-cell fluorescence in situ hybridization (FISH) were prepared as described earlier (Rudolph et al 2001).

DNA Extraction and Amplicon Generation (Probst et al 2013).

DNA was extracted from samples using the XS-buffer protocol (Moissl-Eichinger 2011) and used as template for amplicon-based 16S rRNA gene profiling. Here, bacterial 16S rRNA genes were amplified with primer pair 27F and 1492R (Hazen et al 2010), whereas archaeal 16S rRNA gene with 345af and 1406ur (Burggraf et al 1992, Lane 1991). Amplicons were pooled and purified by agarose-gel electrophoresis as described (Probst et al 2013). Bacterial and archaeal 16S rRNA genes as well as dsrB (dissimilarity sulfite-reductase) genes were quantified by qPCR (quantitative PCR, triplicate reactions) as described previously (Moissl-Eichinger 2011, Probst et al 2013).

PhyloChip G3 Data Acquisition.

The PhyloChip G3™ Assay (Second Genome, South San Francisco, Calif.) and analysis were carried out as described (Hazen et al 2010). Briefly, bacterial (500 ng) and archaeal (100 ng) 16S rRNA gene amplicons were combined, spiked with a known amount of non-16S rRNA genes for standardization, fragmented and biotin labeled. After hybridization on DNA microarrays, images were scanned, background and noise was determined, and fluorescence intensity was scaled to the spike-in internal controls (Hazen et al 2010).

Empirical OTU (eOTU) Discovery from PhyloChip Data (Miezeiewski et al 2013).

The 25-mer 16S probes were compared to their mismatch controls and 24154 were found to be responsive (Hazen et al 2010) in at least 3 samples. Taxonomically related probes were clustered into probe-sets where pair-wise correlations >=0.85 between $\log_2$ transformed fluorescence intensities (FI) were discovered as described by Miezeiewski and co-workers. A total of 1381 probe-sets were found and the empirical operational taxonomic units (eOTU) tracked by each probe-set were taxonomically annotated against the 2012 taxonomy using a Naïve Bayesian scoring and >80% bootstrapped confidence cutoff (DeSantis et al 2006, McDonald et al 2012). The mean $\log_2$ FI among the multiple probes for each eOTU was calculated for each sample. These values are referred to as the hybridization score (HybScore) used in PhyloChip abundance-based analysis. eOTUs detected in the DNA extraction blank were removed from further analyses. For details please see supplementary information.

Statistical Analysis of Microarray Data.

Second Genome's Microbial Profiling Analysis Pipeline (PhyCA-Stats™) was used for univariate and multivariate statistics of abundance scores (hybridization scores) of all eOTUs that were called present in at least one of the samples. The analyses included hierarchical clustering (average neighbor), NMDS (non-metric multidimensional scaling) and Adonis testing based on weighted UniFrac distance measure (Lozupone and Knight 2005, Lozupone et al 2011).

We identified eOTUs that were significantly enriched in a sample category by applying a Welch-test on eOTU trajectories. The same test was applied for microbiome changes at family level, where abundances of each eOTU were summarized per family prior to significance testing.

Performance of Microarray Data for Improved OTU Calling.

In this study, we used the well-established PhyloChip G3 DNA microarray for deciphering community relationships (Cooper et al 2011, DeSantis et al 2007, Hazen et al 2010, Mendes et al 2011, Vaishampayan et al 2013). Although microarray technology designed on the basis of a reference dataset of 16S rRNA genes does not allow the detection of precluded/unknown 16S rRNA genes (Brodie et al 2007, La Duc et al 2009), the approach used herein (Miezeiewski et al 2013) identified an eOTU affiliated to the SM1 Euryarchaeon (bootstrap 70%), which has not been included in the original probe design of the array (method for classification of concatenated, interrupted probe sets identical to method described in supplementary information). Consequently, this approach allowed inclusion of 16S rRNA genes not included in the chip design for microbial community relationship calculations.

SR-FTIR Spectromicroscopy and Data Analysis.

SR-FTIR spectromicroscopy using photon energy in the mid-infrared region (4000 to 650 $cm^{-1}$, Holman et al 2010) was used to obtain chemical information of the biofilm samples. Band assignment and spectra interpretation was done as described earlier (Mantsch and Chapman 1996). More than 70,000 SR-FTIR spectra were collected for all biofilms at the infrared beamline (http://infrared.als.lbl.gov/) as described in Probst et al 2013. For each spectrum, the membrane methyl (—$CH_3$) to the methylene (—$CH_2$) absorbance ratio was computed, and a threshold value of 0.75 was used to designate the spectrum to be archaeal ($\geq 0.75$) or bacterial ($<0.75$; Probst et al 2013)). Univariate analysis was used to obtain semi-quantitative information on sample biogeochemical composition (see supplementary information). Principal Component-Linear Discriminant Analysis (PC-LDA) was performed in the Matlab (The MathWorks, Inc., Massachusetts USA) environment using lipid spectral window (2800-3100 $cm^{-1}$) for archaeal communities, and lipids, plus carbohydrates (1280-900 $cm^{-1}$) for bacterial communities. Both datasets were vector normalized by the Amide II (1550±10 $cm^{-1}$) absorption intensity.

Fluorescence In Situ Hybridization (FISH).

Whole-cell hybridization was carried out as described in Rudolph et al. 2001 with following probes (Rhodamine Green (RG) or CY3 labeled): EUB338/I (Bacteria; Amann et al 1990b), ARCH344 (Archaea; Moissl et al 2003), SMARCH714 (SM1 Euryarchaeon, Moissl et al 2003), SRB385 (sulfate-reducing bacteria (SRB); Amann et al 1990a) and Delta495a/b/c probe mix (SRB; Loy et al 2002). Bacterial positive controls (strain *Escherichia coli* K12, DSM 30083) and negative controls (non-sense probe NONEUB338) were used to validate the experiments. Thereafter the samples were analyzed as described (Probst et al 2013).

Scanning electron microscopy (SEM) and transmission electron microscopy (TEM).

For SEM, drops of fixed samples (0.1% glutardialdehyde; w/v) were placed onto glass slides, covered with a coverslip, and rapidly frozen with liquid nitrogen. The coverslip was removed with a razor blade and the glass slide was immediately fixed with 2.5% (w/v) glutardialdehyde in fixative buffer, washed, postfixed with 1.0% osmium tetroxide, washed with buffer, followed by deionized water, dehydrated in a graded series of acetone solutions, and critical-point dried after transfer to liquid $CO_2$. Specimens were mounted on stubs, coated with 3 nm of platinum using a magnetron sputter coater, and examined with a Zeiss Auriga scanning electron microscope operated at 1 kV. For TEM, fresh, unfixed biofilm pieces were deposited on a carbon-coated copper grid and negatively stained with 2% (w/v) uranyl acetate, pH 4.5 or 2.0% (w/v) phosphotungstic acid (PTA), pH 7.0. Samples were examined using a CM12 transmission electron microscope (Philips) operated at 120 keV.

Results

The Hydrogeology of Sippenauer Moor (SM) and Mühlbacher Schwefelquelle (MSI).

The sulfur springs at the Sippenauer Moor (SM) near Kelheim (Lower Bavaria) rise out of the subsurface karst system developed in the Jurassic carbonate setting (Malm; Abele 1950). To the contrary, the Mühlbacher Schwefelquelle at Isling (MSI) near Regensburg (Upper Palatonia) is not a natural spring (map in FIG. 40). It is a well drilled to a depth of 36.5 m in the year 1925, but has never been used because of a strong sulfur odor (information provided by REWAG Regensburger Energie- and Wasserversorgung AG & Co KG, the electricity and water supply institute at Regensburg, Germany). The MSI site is situated in the transition area of a river terrace of the Danube from pre-Eemian times (Riss glaciation), covered with Wuermian Loess and Loess Loam. The drill log from 1925 notes the 2.6 m thick Loess layer, the interlayering fluvial sediments and the Quaternary base, which overlies the top of the sedimentary Cretaceous bedrock ("Regensburger Grünsandstein"). At a depth of 23.45 m, the well reached an artesian groundwater table (aquifer) with strong discharge and sulfuric odor. It has to be assumed that the well reached the stratigraphic boundary between Cretaceous and Jurassic sediments (Malm), which are both described as (calciferous) sandstones.

The springs at both locations are connected to the deep water flow within the pre-alpine Tertiary Molasse basin (Lemcke 1976). The deep aquifer is developed in the karst and fracture system of the underlying Jurassic sediments. Stable isotope geochemistry at comparable sites within the region (Lower Bavaria) point out the constant drainage of pore water from the hanging Molasse and Cretaceous layers into the underlying karstified Jurassic layers (Andres and Frisch 1981). Isotope mixing ratios that have remained unchanged for decades and one radiocarbon age ($^{14}C$) of 30,000 years (uncalibrated) revealed the long term runoff of water within the deep Malm karst system within the Molasse basin towards the Danube valley downstream of Regensburg (Andres and Frisch 1981).

Even though the sources for hydrogen sulfide of sulfur springs elsewhere in Lower and Upper Bavaria are bituminous Mesozoic sediments, pyrite rich Jurassic sediments (Lias) or Tertiary brown coal deposits (Baumann 1981, Nielsen 1981), the sulfide at SM and MSI comes from microbial sulfate reduction. Due to the cold temperature inorganic reduction processes can be excluded (Nielsen 1981). The sulfates are set free out of salinar formations (Zechstein) located at the alpine rim of the Molasse basin. The sulfidic sulfur develops from the sulfate reduction of substances set free out of salinar formations (Zechstein) located at the alpine rim of the Molasse basin (Nielsen, 1981). Consequently, the reduction must be triggered by microorganisms. Anorganic reduction processes can be excluded because of the lack of higher temperatures (Nielsen 1981). Even though other sources for hydrogen sulfide like bituminous Mesozoic sediments, pyrite rich Jurassic sediments (Lias) or Tertiary brown coal deposits exist (Baumann 1981, Nielsen 1981), being the reason for sulfur springs elsewhere in Lower and Upper Bavaria, the sulfate bound is the only explanation approach for the origin of the hydrogen sulfide in the deep underground waters at both sites, Sippenauer Moor (SM) and Isling (MSI).

Dominance of Archaea in Subsurface Biofilms Confirmed by Molecular Approaches.

PhyloChip G3, qPCR and FISH revealed the dominance of Archaea in the subsurface MSI-BF and SM-BF samples (Table 1). QPCR showed that >97% of all 16S rRNA genes in MSI-BF and SM-BF were archaeal, but only 26% in the surface SOPC community. Cell counting after FISH staining showed 93% and 86% archaea in MSI-BF and SM-BF, respectively. These abundances were confirmed via SR-FTIR image analysis, which typically showed that archaea occupied >97% of the areas in MSI-BF and SM-BF, but only ~38% in SOPC (FIG. 27).

Site-Specific Microbiomes.

PhyloChip G3 DNA microarray technology identified a total of 1300 bacterial and 37 archaeal eOTUs. Hierarchical analyses based on weighted UniFrac dissimilarities revealed clusters of samples based on their geographical regions (SM versus MSI; FIG. 27), which is supported by a highly significant Adonis p-value (0.008). The macroscopic appearance of samples (BF vs. SOPC) was also identified to have a significant influence on the observed microbiome relationships (p-value=0.003) for biofilm samples from both locations. Considering samples from SM only, the microbiome differences between SM-BF and SOPC were insignificant (p-value=0.058) indicating a site-specific microbiome.

Spatial Dynamics of Archaeome and Bacteriome Relationships.

Aiming to analyze the microbial community relationships in detail, NMDS were performed on PhyloChip G3 derived 16S rRNA gene profiles of Bacteria and Archaea separately. For Archaea, the NMDS plot (FIG. 28A, upper panel) separated MSI-BF and SM-BF from SM-SOPC along the NMDS1 axis. This implies a greater similarity in the archaeal community relationship among samples from the anoxic subsurface (biofilms) than among samples from same hydrogeological regions but of different oxygen content (SM-BF versus SOPC). For Bacteria, however, the NMDS plot (FIG. 28A, lower panel) separated the MSI-BF samples from the SM-BF and the SM-SOPC samples, suggesting that the bacterial community relationship was affected more strongly by the hydrogeology (additional information in Table 2). Although there was a strong increase in oxygen content, the bacterial characteristics of the SM-BF tended to be maintained in the short travel distance to the SOPC (FIG. S2).

Both Biofilms Carried Sulfate-Reducing Bacteria (SRB) with Different Taxonomic Affiliation.

290 of 1337 eOTUs were significantly different in their relative abundance when comparing MSI-BF samples with SM-BF samples (FIG. S3A, S4; p-values <0.05) resulting in separated microbiomes (FIG. S3B). We observed that eOTUs of certain phyla like Verrucomicrobia or Spirochaeta and two eOTUs classified as Desulfobacteraceae belonging to the twelve most significant eOTUs (FIG. S5) were significantly enriched in MSI-BF vs. SM-BF samples. Other members of this family of SRB were also significantly enriched in the SM-BF samples but with higher p-values [0.003:0.050]. Notably, SOPC samples clustered with SM-BF samples in hierarchal dendrograms (FIG. 42B) reflecting the similarity of these populations observed in other multivariate statistics mentioned earlier (FIG. 27, Table 2).

Figure 28B:
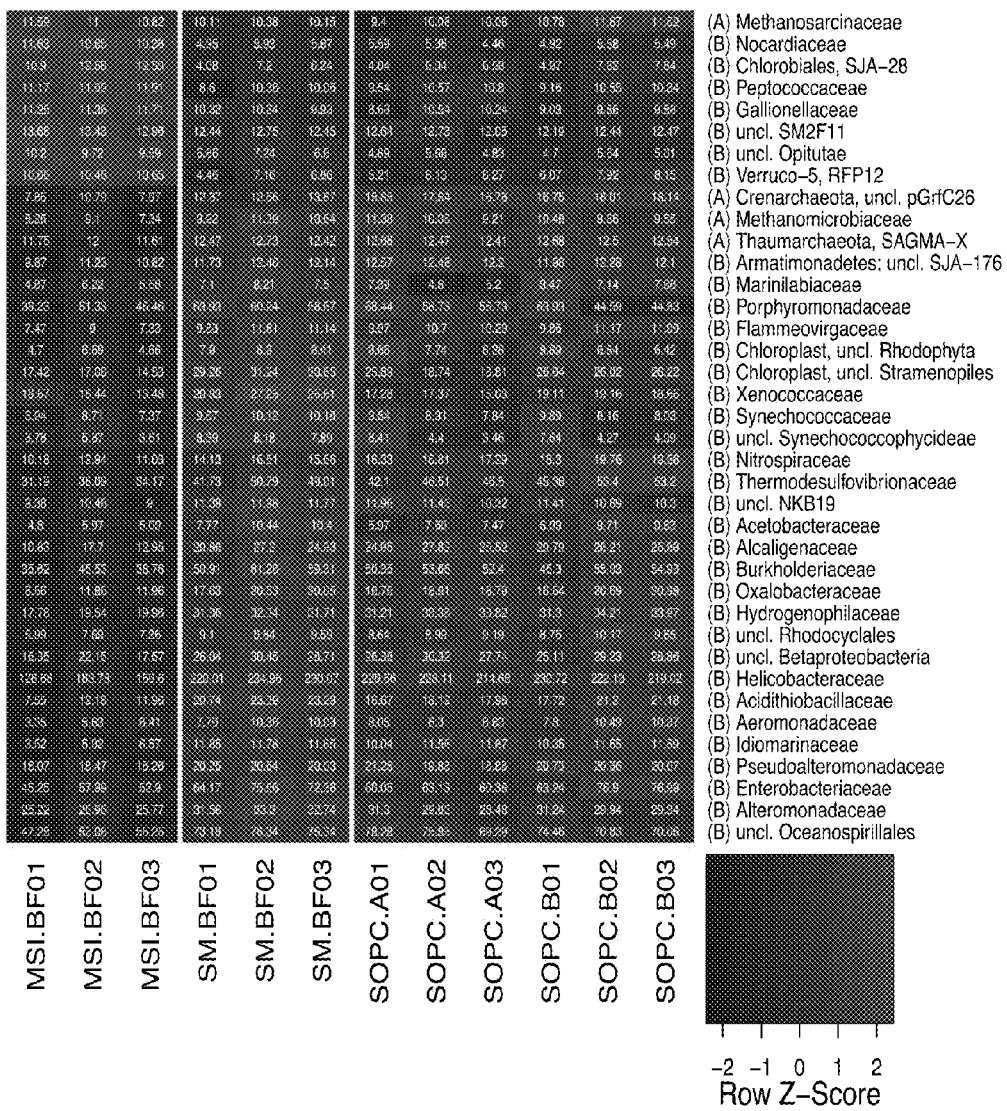

Considering summarized hybScores at family level, 38 of 227 families had significant changes across aggregated trajectories between biofilm categories (FIG. 28B, FIG. 45). While the signatures of the designated SRB families like Desulfobacteraceae, Desulfobulbaceae, Desulfovibrionaceae did not show a significant variation between the MSI-BF and SM-BF (p-values were 0.37, 0.30, and 0.36, respectively). However, the abundance of Desulfobacteraceae displayed a significant difference between the two biofilms, MSI-BF/SM-BF, and the SOPC samples (p-value=0.01). The eOTU and family level analysis allowed the conclusion that SM1 Euryarchaeon biofilms support an enrichment of diverse members of SRB. These data are in accordance with microscopic FISH data, and quantitative PCR of dsrB genes, which showed an increase of one order of magnitude in copy numbers for biofilm samples compared to SOPC samples (Table 1).

Similarity and Variations of Archaeal Lipid Signatures in Biofilms.

Figure 28C:
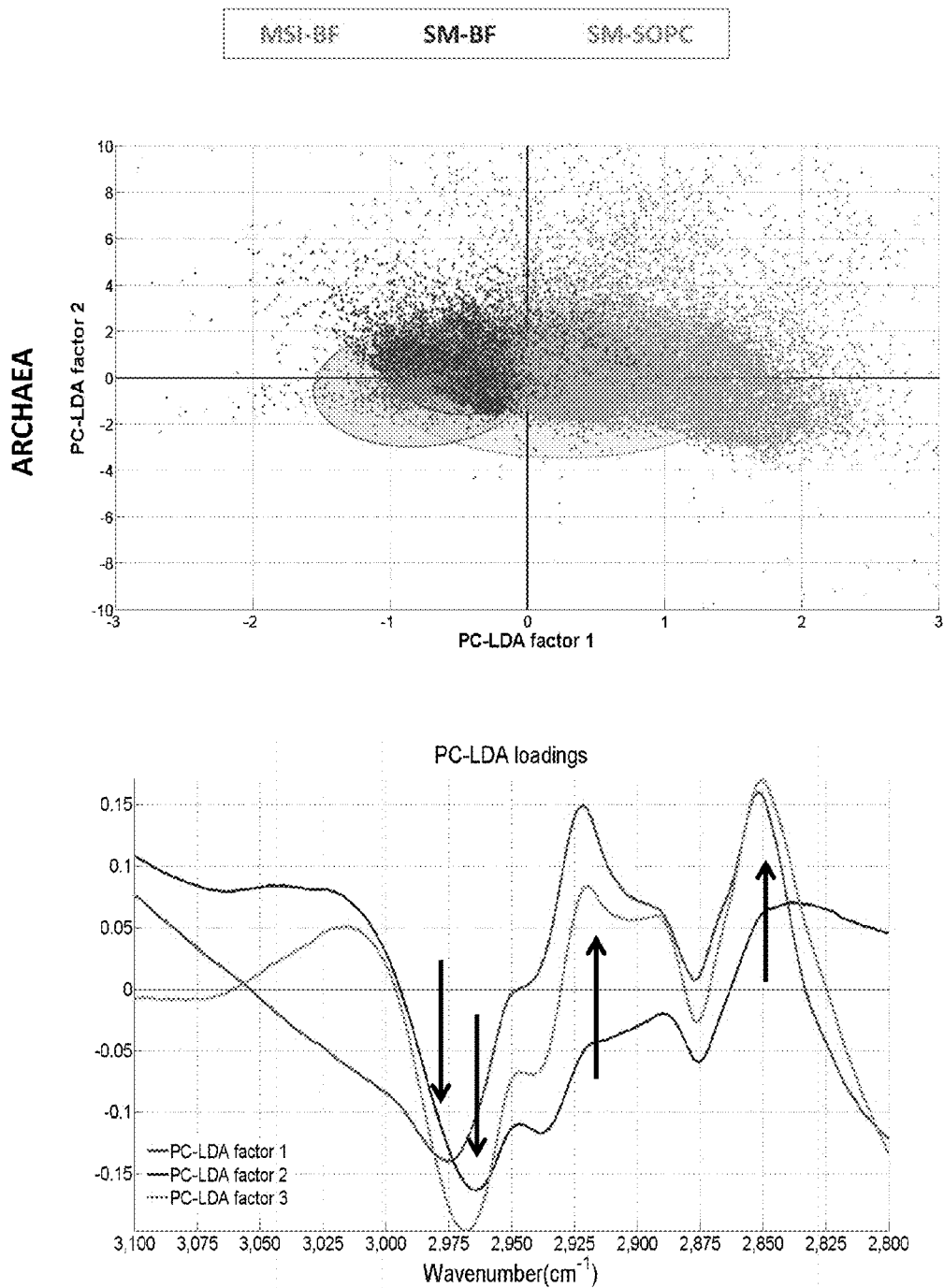
Figure 28D:
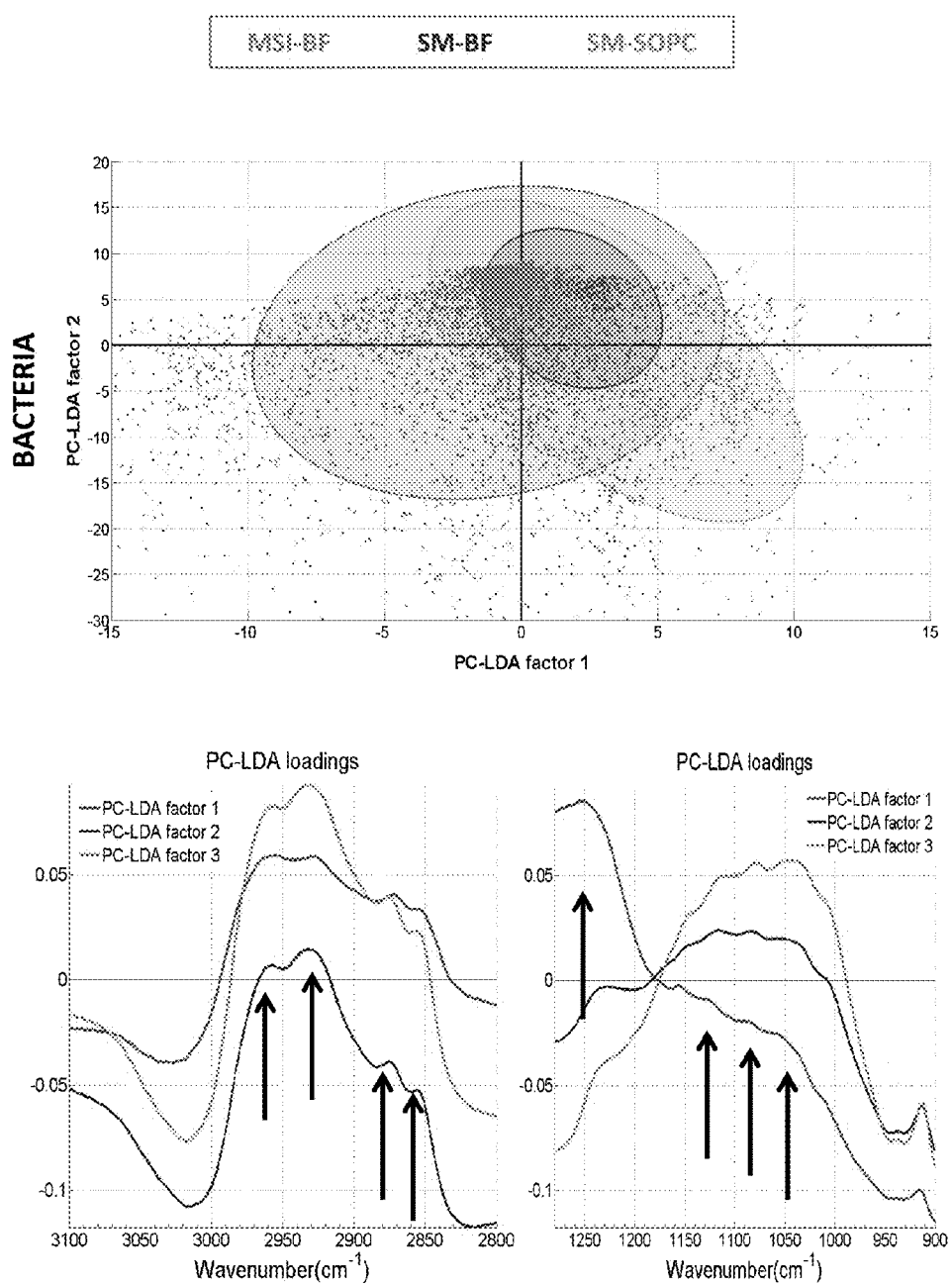

We applied PC-LDA analysis to the SR-FTIR spectra previously categorized as archaeal or bacterial (Table 1) to gain insight into the biochemical differences in the composition at a functional group level of each microbiome. For the archaeal spectra, the two-dimensional PC-LDA score plot revealed that the first PC-LDA factor separated archaea in SM-BF and SM-SOPC samples from the majority (~70%) of the archaea in the MSI-BF samples (FIG. 28C, left panel). The first loading vector (the red trace in FIG. 28C, right panel) showed that positive features near 2924 $cm^{-1}$ and 2850 $cm^{-1}$ were responsible for this separation. These frequencies correspond to the infrared absorption signals of the asymmetric and symmetric vibrations of $CH_2$ in fatty acid chains of the membrane amphiphiles. Additional peaks at 2975-2965 $cm^{-1}$ are associated to the methoxy CH stretching of —$OCH_3$ and —$OCH_2$ ethers (Socrates 2004). Therefore, the PC-LDA loadings plot suggested that the SM-BF and SM-SOPC archaea shared a similar membrane lipid composition, but differed from over 70% of the MSI-BF archaea. This could be explained by differences in the alkyl chain branching and in the polar heads (Ulrih et al 2009). Meanwhile, the two-dimensional PC-LDA score plot of the bacterial spectra in both the lipid and the overall fingerprint region, were similar to microbiome relationships as revealed by PhyloChip analysis (see above).

Ultrastructural Differences Exhibited in SM1-Euryarchaeon Biofilms and Hami Appearance.

A univariate analysis of the infrared absorption bands of the biomacromolecules (FIG. 46) confirmed that MSI-BF and SM-BF had the highest protein and lipid contents, whereas SM-SOPC the highest carbohydrate content. Consequently, samples from both biofilms were analyzed further using SEM and TEM to look into the ultrastructural differences.

SM1 archaeal cells appeared as single or dividing cocci (FIG. 29), connected via a network of cell appendages and extracellular matrices. Considering one layer of SM1 Euryarchaea (FIG. 29A,B), most cells revealed regular distances to six neighbors in a hexagonal manner. Cells in the MSI biofilms were significantly larger than those in the SM biofilms (average diameter of 0.72 µm versus 0.60 homoscedastic student's t-test of 40 cells each: p-value<1.0E-07). Additionally, cell surfaces were napped and connections were smoother in MSI biofilms (FIG. 29C), whereas cell surfaces in the SM biofilms appeared fluffy with more connections between cells (FIG. 29D).

Cells in both biofilms carried hami with distal hooks that appeared correctly folded (FIG. 29E-F). Nevertheless, SM1 Euryarchaea in the MSI biofilm revealed only a low percentage of such correctly folded hami structures with respect to the 'prickle region' (Moissl et al 2005). Prickle regions seemed absent in most MSI hami (FIG. 29E), whereas such "bare" hami were sparsely observed for SM biofilm cells (FIG. 29F). Another difference between the biofilms was the higher occurrence of filamentous bacteria in the SM biofilm, which were in some cases completely cocooned by the SM1 hami (FIG. 30, FIG. 41).

Two SM1 Euryarchaeon Strains Dominated the Two Biofilms.

It was believed that the SM1 Euryarchaeota from SM and MSI were identical based on analysis at the 16S rRNA gene level (Henneberger et al 2006). Yet both showed such strong variations in the membrane lipid composition (FIG. 28C) and ultrastructure (FIG. 29), implicating possible differences between the two archaeal populations at genomic level. Under this observation a comparative Southern blot analysis of biofilm DNA (MSI versus SM) with probes specifically designed to target the hamus gene, that encodes for the major protein of the unique cell surface appendages, was performed (Moissl et al 2005). Using different restriction enzymes (HindII and KpnI) hybridization signals of several distinct bands were retrieved (FIG. 47). This result indicated at least the presence of more than one hamus gene in both samples. Moreover, there is a reliable difference in the restriction pattern between the metagenomic DNA from both biofilm types. Notably, SM1 cells purified from the SM-SOPC (Moissl et al 2003) produced the same pattern as SM-BF. Additionally, sequencing of 96 clones of intergenic spacer regions (between 16S rRNA gene and 23S rRNA gene), without pre-selection of the clones via RFLP (Henneberger et al 2006), showed that six single nucleotide polymorphisms existed between the two dominant sequences from the MSI-BF and SM-BF (FIG. 48), while the 16S rRNA gene sequences were identical providing evidence for different dominant strains of SM1 Euryarchaeota at the two sampling sites.

Discussion.

Subsurface microbial life exists in an environment that is challenging in many ways: lack of sunlight, mostly cold temperatures, low nutrient levels and often anoxic conditions demand alternative ways of carbon assimilation and energy production. This includes the usage of other electron receptors than oxygen, resulting in anaerobic respiration or fermentation (Lovley and Chapelle 1995, Lovley and Coates 2000). To date, information on subsurface life is very limited. This is either due to the restricted accessibility of subsurface biotopes or due to the detection of many unexplored microbial taxa therein, which remain uncultivated and thus largely not understood (Castelle et al 2013, Ortiz et al 2013, Wrighton et al 2012). In this regard, the two vicinal sulfidic springs studied here provide a stable and well accessible window to the subsurface and allow the exploration and comparison of archaeal biofilms delivered to the surface. While microbiome profiling on 16S rRNA gene sequences revealed similar archaeomes, the SR-FTIR approach uncovered striking differences in archaeal lipid signatures at a molecular level. These variations were either caused by the presence of different organisms (at strain level) or altered gene expression of the same organism, most likely reflecting adaptive responses to different environmental conditions. In contrast, PhyloChip data of the two biofilms revealed the enrichment of designated SRB of different taxonomic affiliation at OTU but not at family level, which, however, seemed to share widely diverse lipid composition as revealed by SR-FTIR ordination.

The constant co-appearance and bacterial predominance of such actively sulfate-reducing deltaproteobacteria within both SM1 biofilms suggests a possible syntrophic relationship (Morris et al 2013, Probst et al 2013). Even more, the presence of sulfate-reducers could also reflect environmental conditions prevailing in the biofilms' original biotopes and thus the growth conditions of the SM1 Euryarchaeon.

Generally, SRB's sulfate-reducing activity is linked to the oxidation of organic compounds or molecular hydrogen and to the formation of $H_2S$, an important biogenic compound found in considerable amount (0.85 mg/l) in both spring waters. As a requirement for the SRB catalyzed reactions, the biotope, or respective environment, needs to fulfill at least the following criteria: a) anoxic conditions, b) sulfate as an electron acceptor, and c) an electron donor, most likely either organic molecules or hydrogen. It could therefore be hypothesized, that the SM1 Euryarchaeon thrives under these conditions or even provides such an environment, creating a convenient biotope for SRB.

When biofilm pieces are washed up into oxygen-mixed areas of the surface spring water and attach to rigid material, the entire community is transformed into a string-of-pearls-like macroscopic appearance. The archaeal diversity increased, as shown for instance by the detection of Thaumarchaeota, and the bacteria originally being part of the biofilm, are absorbed into the string-of-pearls community. This process is completed by the most likely intentional settling of filamentous, sulfide-oxidzing bacteria (Thiothrix, *Sulfuricurvum*), which cover the archaeal microcolony and become an equal partner of the SM1 Euryarchaeon (Moissl et al 2002, Rudolph et al 2004). Supporting evidence for this hypothesis comes from the fact that filamentous bacteria were cocooned by cell surface appendages of SM1 Euryarchaeota in biofilm samples and similar bacteriomes were found for the biofilm and the SOPC at the Sippenauer Moor. The biofilms can therefore be considered precursors of the string-of-pearls community (FIG. 41).

Based on hydrogeology we can exclude a direct exchange of biomaterial between both aquifer outlets with respect to the subsurface water current (both aquifers are artesian). Additionally, even though both wells are fed by the same deep groundwater flow within the pre-alpine Tertiary Molasse basin, based on our studies, we can exclude a parallel transport of microbial communities from these regions to both springs, Sippenauer Moor and Mühlbacher Schwefelquelle: If delivered simultaneously to both biotopes from the same origin, one would expect similar patterns in (bio-) geochemical profiles and microbial diversity, since the biofilms analyzed were sampled in parallel (within one day). It appears that the local hydrogeology and geochemistry in the subsurface of the individual springs is responsible for creating different biotopes and causing differences in the observed microbiome structure.

Although a number of details with respect to archaeal 16S rRNA gene sequences, prevalence of SRB and general biofilm-structure are in agreement, the communities from both locations, and also the archaea themselves, reveal severe differences at various levels. For instance, SR-FTIR detected location dependent shifts in lipid profiles of biofilm associated archaea. In general, lipid variations can be growth phase dependent (Thirkell and Gray 1974), point to a specific biotope-adaptation (De Rosa and Gambacorta 1988, Sprott 1992) and thus reflect influences from environmental parameters in both biotopes—or simply minor strain-specific properties. The latter possibility is supported by detectable differences in fingerprint experiments with metagenomic DNA and within the archaeal SM and MSI 16S-23S rRNA gene intergenic spacer regions. Consequently, Southern-blotting and intergenic spacer analysis, together with the above-mentioned SR-FTIR analysis, and ultrastructural analyses suggested that two different SM1 euryarchaeal populations dominate the biofilms that can be found at the Mühlbacher Schwefelquelle and at the Sippenauer Moor. To our knowledge, this is the first report of a natural divergence of one archaeal species in nature.

Studying these archaeal communities, which still remain dark matter with regard to biochemical cycling, provided insight into the hydrogeological impact on microbiome variation and into potential microbial niche differentiation. Our multifarious results, based on the commingling of established and novel methods, have added another piece to the puzzle in order to understand the dynamics of subsurface microbial life in such a great, dark and little explored environment.

References for Example 2

Abele G (1950). Die Heil-und Mineralquellen Südbayerns. Suppenau bei Saal an der Donau. Geologica Bavarica 2: 94-95.

Amann R I, Binder B J, Olson R J, Chisholm S W, Devereux R, Stahl D A (1990a). Combination of 16S rRNA-targeted oligonucleotide probes with flow cytometry for analyzing mixed microbial populations. Appl Environ Microbiol 56: 1919-1925.

Amann R I, Krumholz L, Stahl D A (1990b). Fluorescent-oligonucleotide probing of whole cells for determinative, phylogenetic, and environmental studies in microbiology. J Bacteriol 172: 762-770.

Andres G, Frisch H (1981). Hydrogeologie und Hydraulik im Malmkarst des Molassebeckens und der angrenzenden Fränkischen-Schwäbischen Alb. Schriftenreihe Bayer Landesamt f Wasserwirtschaft 15: 108-117.

Baumann M (1981). Hydrogeologische, hydrochemische und erschließungstechnische Verhältnis se der Schwefelquellen. Schriftenreihe Bayer Landesat f Wasserwirtschaft 15: 4-13.

Brodie E L, DeSantis T Z, Parker J P, Zubietta I X, Piceno Y M, Andersen G L (2007). Urban aerosols harbor diverse and dynamic bacterial populations. Proc Natl Acad Sci USA 104: 299-304.

Burggraf S, Olsen G J, Stetter K O, Woese C R (1992). A phylogenetic analysis of Aquifex pyrophilus. Syst Appl Microbiol 15: 352-356.

Castelle C J, Hug L A, Wrighton K C, Thomas B C, Williams K H, Wu D et al (2013). Extraordinary phylogenetic diversity and metabolic versatility in aquifer sediment. Nat Commun 4: 2120.

Cooper M, La Duc M T, Probst A, Vaishampayan P, Stam C, Benardini J N et al (2011). Comparison of innovative molecular approaches and standard spore assays for assessment of surface cleanliness. Appl Environ Microbiol 77: 5438-5444.

De Rosa M, Gambacorta A (1988). The lipids of archaebacteria. Prog Lipid Res 27: 153-175.

DeSantis T Z, Brodie E L, Moberg J P, Zubieta I X, Piceno Y M, Andersen G L (2007). High-density universal 16S rRNA microarray analysis reveals broader diversity than typical clone library when sampling the environment. Microb Ecol 53: 371-383.

Engel A S, Lee N, Porter M L, Stern L A, Bennett P C, Wagner M (2003). Filamentous "Epsilonproteobacteria" dominate microbial mats from sulfidic cave springs. Appl Environ Microbiol 69: 5503-5511.

Engel A S, Porter M L, Stern L A, Quinlan S, Bennett P C (2004). Bacterial diversity and ecosystem function of filamentous microbial mats from aphotic (cave) sulfidic springs dominated by chemolithoautotrophic "Epsilonproteobacteria". FEMS Microbiol Ecol 51: 31-53.

Hazen T C, Dubinsky E A, DeSantis T Z, Andersen G L, Piceno Y M, Singh N et al (2010). Deep-sea oil plume enriches indigenous oil-degrading bacteria. Science 330: 204-208.

Henneberger R, Moissl C, Amann T, Rudolph C, Huber R (2006). New insights into the lifestyle of the cold-loving SM1 euryarchaeon: natural growth as a monospecies biofilm in the subsurface. Appl Environ Microbiol 72: 192-199.

Holman H Y, Bechtel H A, Hao Z, Martin M C (2010). Synchrotron IR Spectromicroscopy: Chemistry of Living Cells. Anal Chem.

Koch M, Rudolph C, Moissl C, Huber R (2006). A cold-loving crenarchaeon is a substantial part of a novel microbial community in cold sulphidic marsh water. FEMS Microbiol Ecol 57: 55-66.

Kristjansson J K, Stetter K O (1992). Thermophilic bacteria. CRC Press, Inc.: London.

La Duc M T, Osman S, Vaishampayan P, Piceno Y, Andersen G, Spry J A et al (2009). Comprehensive census of bacteria in clean rooms by using DNA microarray and cloning methods. Appl Environ Microbiol 75: 6559-6567.

Lamcke K (1976). Übertiefe Grundgewasser im Süddeutschen Alpenvorland. BuU Ver Schweiz Petroleum-Geol u-Ing 42: 9-18.

Lane D J (1991). 16S/23S rRNA sequencing. Nucleic Acid Techniques in Bacterial Systematics.

Lovley D R, Chapelle F H (1995). Deep subsurface microbial processes. Reviews of Geophysics 33: 365-381.

Lovley D R, Coates J D (2000). Novel forms of anaerobic respiration of environmental relevance. Curr Opin Microbiol 3: 252-256.

Loy A, Lehner A, Lee N, Adamczyk J, Meier H, Ernst J et al (2002). Oligonucleotide microarray for 16S rRNA gene-based detection of all recognized lineages of sulfate-reducing prokaryotes in the environment. Appl Environ Microbiol 68: 5064-5081.

Lozupone C, Knight R (2005). UniFrac: a new phylogenetic method for comparing microbial communities. Appl Environ Microbiol 71: 8228-8235.

Lozupone C, Lladser M E, Knights D, Stombaugh J, Knight R (2011). UniFrac: an effective distance metric for microbial community comparison. ISME J 5: 169-172.

Mantsch H H, Chapman D (1996). Infrared Spectroscopy of Biomolecules. Wiley-Liss, Inc: New York.

Mendes R, Kruijt M, de Bruijn I, Dekkers E, van der Voort M, Schneider J H et al (2011). Deciphering the rhizosphere microbiome for disease-suppressive bacteria. Science 332: 1097-1100.

Miezeiewski M, Schnaufer T, Muraysky M, Wang S, Caro-Aguilar I, Secore S et al (submitted). An in virto culture model to study the dynamics of colonic microbiota in syrian golden hamster and their susceptibility to infection with Clostridium difficile. ISME J.

Moissl C, Rudolph C, Huber R (2002). Natural communities of novel archaea and bacteria with a string-of-pearls-like morphology: molecular analysis of the bacterial partners. Appl Environ Microbiol 68: 933-937.

Moissl C, Rudolph C, Rachel R, Koch M, Huber R (2003). In situ growth of the novel SM1 euryarchaeon from a string-of-pearls-like microbial community in its cold biotope, its physical separation and insights into its structure and physiology. Arch Microbiol 180: 211-217.

Moissl C, Rachel R, Briegel A, Engelhardt H, Huber R (2005). The unique structure of archaeal 'hami', highly complex cell appendages with nano-grappling hooks. Mol Microbiol 56: 361-370.

Moissl-Eichinger C (2011). Archaea in artificial environments: their presence in global spacecraft clean rooms and impact on planetary protection. ISME J 5: 209-219.

Morris B E, Henneberger R, Huber H, Moissl-Eichinger C (2013). Microbial syntrophy: interaction for the common good. FEMS Microbiol Rev 37: 384-406.

Nielsen H (1981). Schwefelisotope and ihre Aus sage zur Entstehung der Schwefelquellen. Schriftenreihe Bayer Landesamt f Wasserwirtschaft 15: 99-107.

Ortiz M, Legatzki A, Neilson J W, Fryslie B, Nelson W M, Wing R A et al (2013). Making a living while starving in the dark: metagenomic insights into the energy dynamics of a carbonate cave. ISME J.

Pamler A N (1991). Origin and morphology of limestone caves. Geol Soc Am Bull 103: 1-21.

Probst A J, Holman H Y, DeSantis T Z, Andersen G L, Birarda G, Bechtel H A et al (2013). Tackling the minority: sulfate-reducing bacteria in an archaea-dominated subsurface biofilm. ISME J 7: 635-651.

Rudolph C, Wanner G, Huber R (2001). Natural communities of novel archaea and bacteria growing in cold sulfurous springs with a string-of-pearls-like morphology. Appl Environ Microbiol 67: 2336-2344.

Rudolph C, Moissl C, Henneberger R, Huber R (2004). Ecology and microbial structures of archaeal/bacterial strings-of-pearls communities and archaeal relatives thriving in cold sulfidic springs. FEMS Microbiol Ecol 50: 1-11.

Socrates G (2004). Infrared and Raman Characteristic Group Frequencies: Tables and Charts. Wiley.

Sprott G D (1992). Structures of archaebacterial membrane lipids. J Bioenerg Biomembr 24: 555-566.

Thirkell D, Gray E M (1974). Variation in the lipid and fatty acid composition in purified membrane fractions from Sarcina aurantiaca in relation to growth phase. Antonie van Leeuwenhoek 40: 71-78.

Ulrich G A, Martino D, Burger K, Routh J, Grossman E L, Ammerman J W et al (1998). Sulfur Cycling in the Terrestrial Subsurface: Commensal Interactions, Spatial Scales, and Microbial Heterogeneity. Microb Ecol 36: 141-151.

Ulrih N P, Gmajner D, Raspor P (2009). Structural and physicochemical properties of polar lipids from thermophilic archaea. Appl Microbiol Biotechnol 84: 249-260.

Vaishampayan P, Probst A J, La Duc M T, Bargoma E, Benardini J N, Andersen G L et al (2013). New perspectives on viable microbial communities in low-biomass cleanroom environments. ISME J 7: 312-324.

Whitman W B, Coleman D C, Wiebe W J (1998). Prokaryotes: the unseen majority. Proc Natl Acad Sci USA 95: 6578-6583.

Wrighton K C, Thomas B C, Sharon I, Miller C S, Castelle C J, VerBerkmoes N C et al (2012). Fermentation, hydrogen, and sulfur metabolism in multiple uncultivated bacterial phyla. Science 337: 1661-1665.

References of Supplementary Data that are not Listed in the Actual Manuscript

Burggraf S, Huber H, Stetter K O. (1997). Reclassification of the crenarchaeal orders and families in accordance with 16S ribosomal RNA sequence data. Int J Syst Bacteriol 47: 657-660.

Edgar R C. (2004). MUSCLE: multiple sequence alignment with high accuracy and high throughput. Nuc Acid Res 32: 1792-1797.

McDonald D, Price N, Goodrich J, Nawrocki E P, DeSantis T Z, Probst A, Andersen G L, Knight R, Hugenholtz P. (2012). An improved Greengenes taxonomy with explicit ranks for ecological and evolutionary analyses of bacteria and archaea. ISME J 6: 610-618.

Summit M, Baross J A. (2001). A novel microbial habitat in the mid-ocean ridge subseafloor. Proc Natl Acad Sci USA 98: 2158-2163

Schloss P D, Westcott S L, Ryabin T, Hall J R, Hartmann M, Hollister E B, Lesniewski R A, Oakley B B, Parks D H, Robinson C J, Sahl J W, Stres B, Thallinger G G, Van Horn D J, Weber C F. (2009). Introducing mothur: Open-source, Platform-Independent, Community-Supported Software for Describing and Comparing Microbial Communities. Appl Env Microbiol 75: 7537-7541.

Wang Q, Garrity G M, Tiedje J M, Cole J R. (2007). Naive Bayesian Classifier for Rapid Assignment of rRNA Sequences into the New Bacterial Taxonomy. Appl Env Microbiol 73: 5261-5267.

Example 3: Groundwater Microbial Community Analysis

Groundwater samples were taken prior to (GWA1) and following acetate amendment (GWB1). Acetate-amended groundwater was injected upgradient 3.5 and 5.5 m below the surface to achieve aquifer concentrations of 15 mM (acetate; Sigma-Aldrich, Saint Louis, Mo., USA) and 2 mM (bromide; Sigma-Aldrich). Prior to acetate amendment 140 L 7 days and 9 days after the start of acetate amendment, 100 L of groundwater were pumped and filtered sequentially through a 1.2 µm pore size pre-filter (293-mm diameter Supor-1200 hydrophilic polyethersulfone membrane disc filter; Pall Corporation, Ann Arbor, Mich., USA), with biomass retained on a 0.2 µm pore size (293-mm diameter Supor-200 hydrophilic polyethersulfone membrane disc; Pall Corporation) and a 0.1 µm pore size sample filter (142-mm diameter Supor-100 hydrophilic polyethersulfone membrane disk filter; Pall Corporation). Filters were immediately frozen in an ethanol-dry ice mix, stored at −80° C., and shipped overnight to University of California, Berkeley for DNA extraction. For cryo-TEM, 500 ml of 0.2 µm filtrate was concentrated with Vivaspins (cut-off 30 kDa; GE Healthcare, Pittsburgh, Pa., USA) to ~500 µL and cryo-plunged immediately.

Approximately 1 g of each filter was used for DNA extraction using the PowerMax® Soil DNA Isolation Kit (MoBio Laboratories, Inc., Carlsbad, Calif., USA, Cat#12988). Manufacturer's protocol was followed, with the exception of adding a freeze/thaw step and vortexing bead tubes for 3.5 minutes after addition of the SDS reagent, followed by 30 minutes at 65° C. with intermittent shaking. DNA in the 5 mL eluted volume was concentrated by sodium acetate/ethanol precipitation with glycogen followed by resuspension in provided elution buffer.

For cryo-TEM and Synchrotron infrared (SIR) spectromicroscopy (see below), 200 mesh lacey carbon coated formvar Cu-grids (Ted Pella Inc., Redding, Calif., USA) were used. For correlative FISH and TEM, a lacey or a continuous formvar support film was laid on TEM nickel finder grids (Maxtaform™ Finder Grid Style H7, 63 µm pitch 400 mesh) and grids were carbon coated. All TEM grids were treated by glow-discharge to improve sample deposition onto the grids. Ten and 250 nm colloidal gold particles (BBlnternational, Cardiff, UK) were put on TEM grids for cryo-TEM and SIR spectroscopy, and for correlative FISH and TEM respectively, and allowed to dry prior to sample addition. Aliquots of 5 µL 0.2 µm filtered groundwater sample were deposited onto the grids, manually blotted with filter paper and plunged into liquid propane at liquid nitrogen temperature using a portable cryo-plunge device on site. Grids were stored in liquid nitrogen until further analysis.

For correlative cryo-TEM and CARD-FISH two approaches were performed. (1) First frozen samples on Ni-Finder TEM grids were imaged and then the CARD-FISH protocol was applied[50]. (2) Frozen samples on Ni-Finder TEM grids were freeze-dried and embedded in low gelling point agarose (0.1% final concentration), dried at room temperature, then fixed in paraformaldehyde solution (2% final concentration), washed in sterile Milli-Q water, dehydrated in 50%, 80%, 90% and in 100% ethanol and air dried. Three different oligonucleotide probes targeting rRNA genes, were applied to cells on TEM grids. Hybridization was performed following a method previously described in Knierim B, et al. Correlative microscopy for phylogenetic and ultrastructural characterization of microbial communities. *Environ Microbiol Rep* 4, 36-41 (2011) hereby incorporated by reference, with a formamide concentration of 50%, incubation at 46° C. for 3 h and washing at 48° C. for 10 min. The subsequent amplification was performed at 46° C. for 10 min. Samples were counterstained with DAPI DNA stain (1 ug mL$^{-1}$ final concentration).

Confocal laser scanning microscopy (CLSM) was performed on a Carl Zeiss Inc. LSM 710 Zen 2010, Release Version 6.0 software (Carl Zeiss MicroImaging Inc., Thornwood, N.Y., USA), equipped with Argon (458 nm, 488 nm, 514 nm) and He—Ne (594 nm, 543 nm, 633 nm) lasers and a diode 45-30 (405 nm). The diode (405 nm) was used for DAPI signals (BP filter 410-585). Positively labelled cells (fluorochrome Alexa Fluor® 546) were detected by using the He—Ne 543 nm laser line (BP filter 548-680). A Plan-Apochromat 100×/1.4 oil DIC (Zeiss) lens was used.

Cryo-TEM images were acquired on a JEOL-3100-FFC electron microscope (JEOL Ltd, Akishima, Tokyo, Japan) equipped with a FEG electron source operating at 300 kV, an Omega energy filter (JEOL), cryo-transfer stage, and a Gatan 795 4K×4K CCD camera (Gatan Inc., Pleasanton, Calif., USA) mounted at the exit of an Electron Decelerator held at a voltage of 200 kV to 250 kV, See Downing K H, Mooney P E. A charge coupled device camera with electron decelerator for intermediate voltage electron microscopy. *Rev Sci Instrum* 79, 043702 (2008). The stage was cooled with liquid nitrogen to 80 K during acquisition of all data sets.

Over 100 two-dimensional (2D) images were recorded at different magnifications giving a pixel size of 0.375 nm, 0.28 nm or 0.22 nm at the specimen. Underfocus values ranged between 3.6 µm±0.25 µm to 12 µm±0.5 µm, and energy filter widths were typically around 30 eV. The survey of the grids and the selection of suitable targets were done in low dose defocused diffraction mode to minimize radiation damage.

Thirteen tomographic tilt series were acquired under low dose conditions, typically over an angular range between +65° and −65°, ±5° with increments of 2°. Between 61 and 66 images were recorded for each tilt series, acquired semi-automatically with the program Serial-EM (http://bio3d.colorado.edu/)[52] adapted to JEOL microscopes. For tilt series data sets, all images show a pixel size of 0.56 nm or 0.746 nm at the specimen. Underfocus values ranged between 3.6 µm±0.25 µm to 9 µm±0.5 µm, and energy filter widths were approximately 30 eV. The average dose used per complete tilt series was ~113 e$^-$ Å$^{-2}$. All tomographic reconstructions were obtained with the program Imod (http://bio3d.colorado.edu/)[52]. The software ImageJ 1.38× (NIH, ImageJ website) was used for analysis of the 2D image projections. All movies were created with the open source package ffmpeg (ffmpeg website). Adobe Photoshop CS5.1 was used to adjust contrast in the images and to insert calibrated scale bars into images.

For subtomographic averaged reconstructions, whole cell reconstructions were surveyed with Imod and the locations of 1,167 S-layer lattice units from three low defocus tomographic reconstructions (382, 410, 375) were manually chosen and stored in segmented models. Cubical subvolumes (64 voxels by side, 0.56 nm$^3$), with assigned normal pointing outwards from the cell surface, were cropped. The side of the cubical volume was about twice the lattice constant and contained a centred repeating unit. The centre of each repeating unit in the subvolume was aligned for averaging 3D S-layer lattices. This process allowed us to compute the centre of mass of each cropped sub-volume and to use a cell surface normal at each point for rotational alignment of all subvolumes. In whole cell data the normal defines the outside of the bacterium and allows the merging of data from different cryo-tomograms. A first model was obtained computing the iterative alignment and averaging of 382 subvolumes cropped from one data set acquired with defocus value of ~6 µm±0.25 µm. For the final refinement of the subtomographic averaged reconstructions shown here 785 subvolumes were used; these were cropped from data sets acquired using defocus value of ~4 µm±0.25 µm (target value 3.6 µm).

Alignment and classification of the boxed sub-volumes were computed with the various utilities within the "X-Window-based Microscopy Image Processing Package", or Xmipp package, available at the Xmipp website. Several clustering or classification strategies using different algorithms were used in order to validate the results across conceptually different methodologies.

Cryo-TEM grids were placed onto the BaF$_2$ infrared windows (International Crystal Laboratories, N.J., USA) under liquid nitrogen. They were then allowed to air dry at ambient temperature on the BaF$_2$ windows.

SIR spectromicroscopy was performed at the infrared beamline 1.4.3 (Advanced Light Source, http://infrared.als.lbl.gov/) on a Nic-Plan infrared microscope (32× objective, numerical aperture=0.65; released software OMNIC 7.0) equipped with a Nicolet Magna 760 infrared spectrometer (Thermo Scientific Inc., MA, USA) at the mid-infrared frequency range (2.5-15.5 µm wavelength, or 4000-650 cm$^{-1}$ wavenumber). The infrared signals (in absorbance) from the energy exchange between the infrared photons and biomolecules were sampled by dividing the TEM grid in 2-µm pixels, raster scanned and processed following a method previously described elsewhere (See Birarda G, et al. Synchrotron infrared imaging of advanced glycation endproducts (AGEs) in cardiac tissue from mice fed high glycemic diets. *Biomedical Spectroscopy and Imaging* 2, 301-315 (2013); and Probst A J, et al. Tackling the minority: sulfate-reducing bacteria in an archaea-dominated subsurface biofilm. *ISME J* 7, 635-651 (2013)). Cells were detected by using the absorption bands of protein amide I and of lipids methyl (—$CH_3$) and methylene (—$CH_2$—) groups.

Other analysis including FISH, Catalysed reporter deposition fluorescence in situ hybridization (CARD-FISH), and genome-wide sequencing was then performed on the samples.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

TABLE 2

Overview of multivariate statistics performed on the bacterial microbiome and on the archaeal microbiome. Entire Microbiome is used for finding significantly eOTUs between sample groups (Welch-test). "+" = positive, "−" negative

|  | Factor | Hydrogeological location | Appearance | Groups | SM | MSI-SOPC | Biofilms |
|---|---|---|---|---|---|---|---|
|  | Bins | MSI\|SM | BF\|SOPC | MSI-BF\|SM-BF\|SOPC | SM-BF\|SOPC | MSI-BF\|SOPC | MSI-BF\|SM-BF |
|  | Sample counts | 3\|9 | 6\|6 | 3\|3\|6 | 3\|6 | 3\|6 | 3\|3 |
| Bacterial microbiome | NMDS distinct | + | − | − | − | + | + |
|  | HC-AN distinct | + | − | − | − | + | + |
| Archaeal microbiome | NMDS distinct | − | + | − | + | + | − |
|  | HC-AN distinct | − | − | − | − | − | − |
| Enitre microbiome | Diff. eOTU count | 512 | 480 | 522 | 248 | 550 | 290 |

What is claimed is:

1. A method for microbial community screening and profiling (MCSP), said method comprising the steps
    (a) providing a biological sample on an infrared (IR) compatible substrate for sample image and spectral detection acquisition;
    (b) performing IR spectromicroscopy on a selected region of said sample using transmission or transflectance mode to generate infrared spectra from said sample;
    (c) detecting infrared spectra from said sample and acquiring micrometer resolution infrared vibrational spectral maps and digital images of said sample;
    (d) pre-processing vibrational spectral and digital data from the infrared map and image to correct the baseline and to remove measurement artifacts and result in processed spectral and digital data;
    (e) performing spectral analysis on said processed spectral and digital data in
        (1) a supervised manner to distinguish bacteria from archaea, wherein supervised parameters used for the spectral analysis are the spectral regions of interest (sROI) and the threshold for $CH_3/CH_2$ ratio, and
        (2) in an unsupervised manner to determine the distributions of archaea, bacteria and chemical variations in the sample;
    (f) conducting biological analyses on said sample, in parallel or sequentially with any of steps (d) through (e) to provide quantification of microorganism abundance within the microbial communities in the selected region of said sample, wherein the biological analyses is genomic sequencing, probe hybridization, phylogenetic analysis, or mass spectrometry.

2. The method of claim 1, wherein in step (e)(1) the spectral regions of interest (sROI) are the lipid region (2800-3100 $cm^{-1}$) and the carbohydrate region (1000-1280 $cm^{-1}$) or the molecular fingerprint region (1480-650 $cm^{-1}$).

3. The method of claim 1, wherein in step (e)(1), the threshold value of $CH_3/CH_2$ or $CH_2/CH_3$ selected to quantify the relative abundance of archaeal and bacterial communities inside said sample.

4. The method of claim 3, wherein in step (e)(1), the threshold value of is 0.72 to 0.8 for $CH_3/CH_2$, and 1.38 to 1.25 for $CH_2/CH_3$.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cagcatcaaa acaggcgggt gc                                    22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gttcctctga atttgtatac gg                                    22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cggggygcas caggcgcgaa                                       20

<210> SEQ ID NO 4
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(4)
<223> OTHER INFORMATION: n is a, c, g, or t

<400> SEQUENCE: 4

```
gccnrggctt atcgcagctt                                              20

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
acgggcggtg tgtrcaa                                                 17

<210> SEQ ID NO 6
<211> LENGTH: 25
<212> TYPE: DNA
<213> ORGANISM: Artificial Sequence
<220> FEATURE:
<223> OTHER INFORMATION: Probe

<400> SEQUENCE: 6
tgtgcaagga gcggggacat attca                                        25
```